US012565529B2

(12) United States Patent
Leon et al.

(10) Patent No.: US 12,565,529 B2
(45) Date of Patent: Mar. 3, 2026

(54) METHODS FOR TREATING TYPE 1 DIABETES

(71) Applicant: Provention Bio, Inc., Red Bank, NJ (US)

(72) Inventors: Francisco Leon, Bethesda, MD (US); Ralph Raymond, Red Bank, NJ (US)

(73) Assignee: Provention Bio, Inc., Red Bank, NJ (US)

( * ) Notice: Subject to any disclaimer, the term of this patent is extended or adjusted under 35 U.S.C. 154(b) by 0 days.

(21) Appl. No.: 17/752,660

(22) Filed: May 24, 2022

(65) Prior Publication Data

US 2022/0380465 A1 Dec. 1, 2022

Related U.S. Application Data

(60) Provisional application No. 63/192,402, filed on May 24, 2021.

(51) Int. Cl.
*C07K 16/28* (2006.01)
*A61K 39/00* (2006.01)
*A61P 3/10* (2006.01)

(52) U.S. Cl.
CPC ............ *C07K 16/2809* (2013.01); *A61P 3/10* (2018.01); *A61K 2039/505* (2013.01); *A61K 2039/545* (2013.01)

(58) Field of Classification Search
CPC ... C07K 16/2809; C07K 2317/24; A61P 3/10; A61K 2039/505; A61K 2039/545
See application file for complete search history.

(56) References Cited

U.S. PATENT DOCUMENTS

| | | | |
|---|---|---|---|
| 4,079,126 A | 3/1978 | Homma et al. | |
| 4,221,794 A | 9/1980 | Simon et al. | |
| 4,361,549 A | 11/1982 | Kung et al. | |
| 4,515,893 A | 5/1985 | Kung et al. | |
| 4,658,019 A | 4/1987 | Kung et al. | |
| 4,695,624 A | 9/1987 | Marburg et al. | |
| 4,830,852 A | 5/1989 | Marburg et al. | |
| 4,882,317 A | 11/1989 | Marburg et al. | |
| 4,882,424 A | 11/1989 | Schlossman et al. | |
| 5,078,998 A | 1/1992 | Bevan et al. | |
| 5,585,089 A | 12/1996 | Queen et al. | |
| 5,624,821 A | 4/1997 | Winter et al. | |
| 5,885,573 A | 3/1999 | Bluestone et al. | |
| 6,113,901 A | 9/2000 | Bluestone | |
| 6,143,297 A | 11/2000 | Bluestone | |
| 6,406,696 B1 | 6/2002 | Bluestone | |
| 6,491,916 B1 | 12/2002 | Bluestone et al. | |
| 6,723,538 B2 | 4/2004 | Mack et al. | |
| 6,905,685 B2 | 6/2005 | Kwon | |
| 6,956,041 B2 | 10/2005 | Blumenkopf et al. | |
| 7,041,289 B1 | 5/2006 | Bach et al. | |
| 7,091,208 B2 | 8/2006 | Blumenkopf et al. | |
| 7,235,641 B2 | 6/2007 | Kufer et al. | |

| | | |
|---|---|---|
| 7,262,276 B2 | 8/2007 | Huang et al. |
| 7,304,033 B2 | 12/2007 | Larsen et al. |
| 7,395,158 B2 | 7/2008 | Monfre et al. |
| 7,482,327 B2 | 1/2009 | Hagerty et al. |
| 7,563,869 B2 | 7/2009 | Honjo et al. |
| 7,569,569 B2 | 8/2009 | Blumenkopf et al. |
| 7,592,313 B2 | 9/2009 | Zheng et al. |
| 7,612,181 B2 | 11/2009 | Chengbin et al. |
| 7,635,472 B2 | 12/2009 | Kuler et al. |
| 7,714,103 B2 | 5/2010 | Levetan et al. |
| 7,728,114 B2 | 6/2010 | Mach et al. |
| 7,744,863 B1 | 6/2010 | Hall et al. |
| 7,820,166 B2 | 10/2010 | Lanzavecchia |
| 7,883,703 B2 | 2/2011 | Weiner et al. |
| 7,883,709 B2 | 2/2011 | Weiner et al. |
| 7,919,089 B2 | 4/2011 | Kufer et al. |
| 7,989,415 B2 | 8/2011 | Levetan et al. |
| 7,998,479 B2 | 8/2011 | Honjo et al. |
| 8,007,796 B2 | 8/2011 | Baeuerle et al. |
| 8,076,459 B2 | 12/2011 | Hofmeister et al. |
| 8,101,722 B2 | 1/2012 | Kufer et al. |
| 8,182,812 B2 | 5/2012 | Schuurman et al. |
| 8,211,430 B2 | 7/2012 | Levetan et al. |
| 8,211,440 B2 | 7/2012 | Chang et al. |
| 8,246,955 B2 | 8/2012 | Honjo et al. |
| 8,246,960 B2 | 8/2012 | Chang et al. |
| 8,258,268 B2 | 9/2012 | Wu et al. |

(Continued)

FOREIGN PATENT DOCUMENTS

| | | |
|---|---|---|
| EP | 0440373 A1 | 8/1991 |
| EP | 0497883 A1 | 8/1992 |

(Continued)

OTHER PUBLICATIONS

Kumar et al., "Novel Selective Thiadiazine DYRK1A Inhibitor Lead Scalfold with Human Pancreatic Beta-Cell Proliferation Activity", Eur. J. Med. Chem., vol. 157, pp. 1005-1016, Sep. 5, 2018.

Levy et al., "Simple Empirical Assessment of Beta-Cell Function by a Constant Infusion of Glucose Test in Normal and Type 2 (Non-Insulin-Dependent) Diabetic Subjects," Diabetologia, vol. 34, No. 7, pp. 488-499, Jul. 1991.

Redondo et al., "Index60 as an Additional Diagnostic Criterion for Type 1 Diabetes," Diabetologia, vol. 64, No. 4, pp. 836-844, Jan. 2021.

Schiavon et al., "Model-Based Assessment of C-Peptide Secretion and Kinetics in Post Gastric Pypass Individuals Experiencing Postprandial Hyperinsulinemic Hypoglycemia," Frontiers in Endocrinology, vol. 12, No. 611253, pp. 1-10, Mar. 15, 2021.

(Continued)

*Primary Examiner* — Janet L Andres
*Assistant Examiner* — Brian Hartnett
(74) *Attorney, Agent, or Firm* — STEPTOE LLP; Z. Ying Li; Debashree Chatterjee

(57) ABSTRACT

Provided herein are a method of treating type 1 diabetes (T1D). In some embodiments, such method can include administering to a subject in need thereof a 12-day course of teplizumab at a total dose of more than about 9000 μg/m².

66 Claims, 35 Drawing Sheets

Specification includes a Sequence Listing.

(56) References Cited

U.S. PATENT DOCUMENTS

| | | | |
|---|---|---|---|
| 8,383,578 | B2 | 2/2013 | Levetan et al. |
| 8,394,926 | B2 | 3/2013 | Lutterbuse et al. |
| 8,398,995 | B2 | 3/2013 | Rottiers et al. |
| 8,420,081 | B2 | 4/2013 | Fraunhofer et al. |
| 8,481,022 | B2 | 7/2013 | Lodie et al. |
| 8,530,629 | B2 | 9/2013 | Chang |
| 8,551,478 | B2 | 10/2013 | Mach et al. |
| 8,586,714 | B2 | 11/2013 | Ghayur et al. |
| 8,623,830 | B2 | 1/2014 | Flier et al. |
| 8,663,634 | B2 | 3/2014 | Koenig |
| 8,735,553 | B1 | 5/2014 | Li et al. |
| 8,785,400 | B2 | 7/2014 | Levetan et al. |
| 8,790,645 | B2 | 7/2014 | Kufer et al. |
| 8,808,689 | B1 | 8/2014 | Levetan |
| 8,816,047 | B2 | 8/2014 | Levetan et al. |
| 8,846,873 | B2 | 9/2014 | Xiao et al. |
| 8,883,146 | B2 | 11/2014 | Fraunhofer et al. |
| 8,932,586 | B2 | 1/2015 | Jones et al. |
| 8,951,518 | B2 | 2/2015 | Honjo et al. |
| 8,980,244 | B2 | 3/2015 | Mandelboim et al. |
| 8,987,425 | B2 | 3/2015 | Lee et al. |
| 9,056,906 | B2 * | 6/2015 | Koenig ..................... A61P 1/04 |
| 9,079,965 | B2 | 7/2015 | Zhou et al. |
| 9,085,619 | B2 | 7/2015 | Fraunhofer et al. |
| 9,089,531 | B2 | 7/2015 | Kaufman et al. |
| 9,102,736 | B2 | 8/2015 | Hofmeister et al. |
| 9,192,665 | B2 | 11/2015 | Zugmaier et al. |
| 9,217,034 | B2 | 12/2015 | Li et al. |
| 9,226,962 | B2 | 1/2016 | LeGall et al. |
| 9,249,211 | B2 | 2/2016 | Schellenberger et al. |
| 9,296,815 | B2 | 3/2016 | D'Angelo et al. |
| 9,308,257 | B2 | 4/2016 | Sharma et al. |
| 9,315,585 | B2 | 4/2016 | Cheung et al. |
| 9,321,812 | B2 | 4/2016 | Leveta |
| 9,371,517 | B2 | 6/2016 | Jones et al. |
| 9,382,329 | B2 | 7/2016 | Chang et al. |
| 9,447,387 | B2 | 9/2016 | Jones et al. |
| 9,447,431 | B2 | 9/2016 | Thess et al. |
| 9,453,052 | B2 | 9/2016 | Gruber et al. |
| 9,474,744 | B2 | 10/2016 | Cohen et al. |
| 9,493,563 | B2 | 11/2016 | Blein et al. |
| 9,511,110 | B2 | 12/2016 | Levetan |
| 9,562,110 | B2 | 2/2017 | Zhou et al. |
| 9,574,010 | B2 | 2/2017 | Spreter Von Kreudenstein et al. |
| 9,587,021 | B2 | 3/2017 | Huang et al. |
| 9,611,325 | B2 | 4/2017 | Zhou et al. |
| 9,616,105 | B2 | 4/2017 | Paulsen et al. |
| 9,670,286 | B2 | 6/2017 | Chang et al. |
| 9,682,143 | B2 | 6/2017 | Chang et al. |
| 9,688,772 | B2 | 6/2017 | Cheung et al. |
| 9,695,250 | B2 | 7/2017 | Lutterbuse et al. |
| 9,701,749 | B2 | 7/2017 | Shibayama et al. |
| 9,708,412 | B2 | 7/2017 | Baeuerle et al. |
| 9,777,073 | B2 | 10/2017 | Zhou et al. |
| 9,783,609 | B2 | 10/2017 | Honjo et al. |
| 9,802,995 | B2 | 10/2017 | Ahmed et al. |
| 9,820,955 | B2 | 11/2017 | Kaufman et al. |
| 9,850,304 | B2 | 12/2017 | Mach et al. |
| 9,879,088 | B2 | 1/2018 | Chang et al. |
| 9,982,063 | B2 | 5/2018 | Lutterbuse et al. |
| 9,987,356 | B2 | 6/2018 | Reimann et al. |
| 10,000,567 | B2 | 6/2018 | Ellis et al. |
| 10,000,574 | B2 | 6/2018 | Hofmeister et al. |
| 10,010,577 | B2 | 7/2018 | Levetan |
| 10,010,578 | B2 | 7/2018 | Levetan |
| 10,010,579 | B2 | 7/2018 | Levetan |
| 10,010,580 | B2 | 7/2018 | Levetan |
| 10,016,482 | B2 | 7/2018 | Levetan |
| 10,022,440 | B2 | 7/2018 | Wasserfall et al. |
| 10,023,639 | B2 | 7/2018 | Li et al. |
| 10,059,767 | B2 | 8/2018 | Protzer et al. |
| 10,081,809 | B2 | 9/2018 | Monteleone et al. |
| 10,086,046 | B2 | 10/2018 | Paulsen et al. |
| 10,093,736 | B2 | 10/2018 | Sahin et al. |
| 10,106,623 | B2 | 10/2018 | Uhlin et al. |
| 10,111,968 | B2 | 10/2018 | Thess et al. |
| 10,118,964 | B2 | 11/2018 | Zhou et al. |
| 10,130,638 | B2 | 11/2018 | Zugmaier et al. |
| 10,150,812 | B2 | 12/2018 | Huang et al. |
| 10,159,710 | B2 | 12/2018 | Gruber et al. |
| 10,167,341 | B2 | 1/2019 | Cheung et al. |
| 10,191,034 | B2 | 1/2019 | Nagorsen |
| 10,239,952 | B2 | 3/2019 | Scheinberg et al. |
| 10,251,934 | B2 | 4/2019 | Elliman |
| 10,266,608 | B2 | 4/2019 | Wu |
| 10,272,050 | B2 | 4/2019 | Farokhzad et al. |
| 10,280,425 | B2 | 5/2019 | Chen et al. |
| 10,287,365 | B2 | 5/2019 | Cheung et al. |
| 10,301,389 | B2 | 5/2019 | Ho et al. |
| 10,316,093 | B2 | 6/2019 | Cheung et al. |
| 10,329,314 | B2 | 6/2019 | Fan et al. |
| 10,329,350 | B2 | 6/2019 | Chou et al. |
| 10,369,114 | B2 | 8/2019 | Schentag et al. |
| 10,376,518 | B2 | 8/2019 | Ellis et al. |
| 10,378,055 | B2 | 8/2019 | Ferreri et al. |
| 10,413,605 | B2 | 9/2019 | Christen et al. |
| 10,434,078 | B2 | 10/2019 | Kaufman et al. |
| 10,443,056 | B2 | 10/2019 | Monteleone et al. |
| 10,449,170 | B2 | 10/2019 | Venn-Watson |
| 10,465,003 | B2 | 11/2019 | Hedrick et al. |
| 10,487,098 | B2 | 11/2019 | Fan et al. |
| 10,519,248 | B2 | 12/2019 | Cheung et al. |
| 10,548,929 | B2 | 2/2020 | Champion et al. |
| 10,556,964 | B2 | 2/2020 | Zhou et al. |
| 10,570,103 | B2 | 2/2020 | Beaton et al. |
| 10,584,180 | B2 | 3/2020 | Gruber |
| 10,590,182 | B2 | 3/2020 | Lim et al. |
| 10,633,440 | B2 | 4/2020 | Bonvini et al. |
| 10,640,576 | B2 | 5/2020 | Jang et al. |
| 10,647,768 | B2 | 5/2020 | Johnson et al. |
| 10,647,770 | B2 | 5/2020 | Shibayama et al. |
| 10,662,243 | B2 | 5/2020 | Nagorsen et al. |
| 10,662,252 | B2 | 5/2020 | Chang et al. |
| 10,688,186 | B2 | 6/2020 | Shalibhai |
| 10,696,744 | B2 | 6/2020 | Zugmaier et al. |
| 10,717,780 | B2 | 7/2020 | Sahin et al. |
| 10,730,880 | B2 | 8/2020 | Allen et al. |
| 10,730,943 | B2 | 8/2020 | Protzer et al. |
| 10,745,478 | B2 | 8/2020 | Sirianni et al. |
| 10,752,686 | B2 | 8/2020 | Ma et al. |
| 10,772,917 | B2 | 9/2020 | Kieffer et al. |
| 10,772,958 | B2 | 9/2020 | Yu et al. |
| 10,806,787 | B2 | 10/2020 | Kudo et al. |
| 10,849,945 | B2 | 12/2020 | Champion et al. |
| 10,858,663 | B2 | 12/2020 | Rottiers et al. |
| 10,865,230 | B2 | 12/2020 | Liu et al. |
| 10,882,909 | B2 | 1/2021 | Ho et al. |
| 10,905,727 | B2 | 2/2021 | Rottiers et al. |
| 10,925,972 | B2 | 2/2021 | Demetriou et al. |
| 10,940,151 | B2 | 3/2021 | Friedman et al. |
| 10,961,315 | B2 | 3/2021 | Liu |
| 10,973,889 | B2 | 4/2021 | Kjellman et al. |
| 10,975,112 | B2 | 4/2021 | Zhao |
| 10,980,890 | B2 | 4/2021 | Kim et al. |
| 11,008,601 | B2 | 5/2021 | Wang et al. |
| 11,026,994 | B2 | 6/2021 | Elliman |
| 11,029,317 | B2 | 6/2021 | Sarwal et al. |
| 11,046,745 | B2 | 6/2021 | Sahin et al. |
| 11,046,768 | B2 | 6/2021 | Cheung et al. |
| 11,052,052 | B2 | 7/2021 | Schentag et al. |
| 11,065,343 | B2 | 7/2021 | Park et al. |
| 11,066,476 | B2 | 7/2021 | Fang et al. |
| 11,084,876 | B2 | 8/2021 | Kufer et al. |
| 11,091,547 | B2 | 8/2021 | Ferrone et al. |
| 11,098,079 | B2 | 8/2021 | Hoang et al. |
| 11,098,115 | B2 | 8/2021 | Willemsen et al. |
| 11,123,438 | B2 | 9/2021 | Li et al. |
| 11,124,568 | B1 | 9/2021 | Ahmed et al. |
| 11,124,578 | B2 | 9/2021 | Heusser et al. |
| 11,147,886 | B2 | 10/2021 | Ng et al. |
| 11,154,617 | B2 | 10/2021 | Baeuerle et al. |
| 11,155,622 | B2 | 10/2021 | Brown et al. |
| 11,160,876 | B2 | 11/2021 | Markovic et al. |
| 11,161,906 | B2 | 11/2021 | Lowman et al. |

(56)                    References Cited

U.S. PATENT DOCUMENTS

| | | |
|---|---|---|
| 11,167,040 B2 | 11/2021 | Kim et al. |
| 11,173,214 B2 | 11/2021 | Kim et al. |
| 11,174,323 B2 | 11/2021 | Marasco et al. |
| 11,186,638 B2 | 11/2021 | Snell et al. |
| 11,193,155 B2 | 12/2021 | Wang et al. |
| 11,220,551 B2 | 1/2022 | Moffat et al. |
| 11,306,142 B2 | 4/2022 | Nathwani et al. |
| 11,311,631 B2 | 4/2022 | Markovic et al. |
| 11,332,544 B2 | 5/2022 | Davidson et al. |
| 11,338,036 B2 | 5/2022 | Zaghouani |
| 11,339,225 B2 | 5/2022 | Li et al. |
| 11,377,485 B2 | 7/2022 | Wong et al. |
| 11,396,547 B2 | 7/2022 | Bai et al. |
| 11,396,554 B2 | 7/2022 | Soliman |
| 11,413,353 B2 | 8/2022 | Kim et al. |
| 11,414,491 B2 | 8/2022 | Russell et al. |
| 11,419,933 B2 | 8/2022 | Kanapuram et al. |
| 11,427,644 B2 | 8/2022 | Stuhler |
| 11,433,141 B2 | 9/2022 | Akiyama et al. |
| 11,434,291 B2 | 9/2022 | Leon |
| 12,006,366 B2 | 6/2024 | Leon et al. |
| 2001/0044416 A1 | 11/2001 | McCluskie et al. |
| 2002/0006403 A1 | 1/2002 | Yu et al. |
| 2003/0017979 A1 | 1/2003 | Mack et al. |
| 2003/0083472 A1 | 5/2003 | Tamatani et al. |
| 2003/0108548 A1 | 6/2003 | Bluestone et al. |
| 2003/0194403 A1 | 10/2003 | van de Winkel et al. |
| 2003/0216551 A1 | 11/2003 | Delovitch |
| 2003/0235583 A1 | 12/2003 | Sturis et al. |
| 2004/0023885 A1 | 2/2004 | Brand et al. |
| 2004/0024208 A1 | 2/2004 | Das et al. |
| 2004/0037826 A1 | 2/2004 | Michelsen et al. |
| 2004/0054186 A1 | 3/2004 | Das et al. |
| 2004/0072749 A1 | 4/2004 | Zochoer et al. |
| 2004/0073026 A1 | 4/2004 | Das et al. |
| 2004/0077875 A1 | 4/2004 | Das et al. |
| 2004/0082664 A1 | 4/2004 | Won et al. |
| 2004/0170626 A1 | 9/2004 | Schuurman et al. |
| 2004/0175786 A1 | 9/2004 | Choi et al. |
| 2004/0204429 A1 | 10/2004 | Yuan |
| 2004/0209801 A1 | 10/2004 | Brand et al. |
| 2004/0229788 A1 | 11/2004 | Tamatani et al. |
| 2005/0009870 A1 | 1/2005 | Sher et al. |
| 2005/0014786 A1 | 1/2005 | Sun et al. |
| 2005/0037000 A1 | 2/2005 | Stavenhagen et al. |
| 2005/0043233 A1 | 2/2005 | Stefanic et al. |
| 2005/0054659 A1 | 3/2005 | Ellsworth et al. |
| 2005/0064514 A1 | 3/2005 | Stavenhagen et al. |
| 2005/0080087 A1 | 4/2005 | Pendri et al. |
| 2005/0119269 A1 | 6/2005 | Rao et al. |
| 2005/0143381 A1 | 6/2005 | Yu et al. |
| 2005/0147581 A1 | 7/2005 | Zamiri et al. |
| 2005/0171110 A1 | 8/2005 | Yu et al. |
| 2005/0176028 A1 | 8/2005 | Hofmeister et al. |
| 2005/0191702 A1 | 9/2005 | Mach et al. |
| 2005/0196395 A1 | 9/2005 | Weiner et al. |
| 2005/0250691 A1 | 11/2005 | Robertson et al. |
| 2006/0002933 A1 | 1/2006 | Bluestone et al. |
| 2006/0057620 A1 | 3/2006 | Krause |
| 2006/0058311 A1 | 3/2006 | Munzert et al. |
| 2006/0062780 A1 | 3/2006 | Zocher et al. |
| 2006/0078557 A1 | 4/2006 | Bluestone |
| 2006/0079563 A1 | 4/2006 | Das et al. |
| 2006/0177896 A1 | 8/2006 | Mach et al. |
| 2006/0183674 A1 | 8/2006 | Brand et al. |
| 2006/0188494 A1 | 8/2006 | Bach et al. |
| 2006/0194725 A1 | 8/2006 | Rasmussen et al. |
| 2006/0235201 A1 | 10/2006 | Kischel |
| 2006/0275292 A1 | 12/2006 | Delovitch |
| 2006/0292142 A1 | 12/2006 | Bluestone et al. |
| 2007/0053954 A1 | 3/2007 | Rowe et al. |
| 2007/0065437 A1 | 3/2007 | Higuchi et al. |
| 2007/0071675 A1 | 3/2007 | Wu et al. |
| 2007/0077246 A1 | 4/2007 | Koenig et al. |
| 2007/0082841 A1 | 4/2007 | Higuchi et al. |
| 2007/0086942 A1 | 4/2007 | Chang et al. |
| 2007/0087971 A1 | 4/2007 | Levetan et al. |
| 2007/0190045 A1 | 8/2007 | Herold et al. |
| 2007/0190052 A1 | 8/2007 | Herold et al. |
| 2007/0249529 A1 | 10/2007 | Hofmeister et al. |
| 2007/0264229 A1 | 11/2007 | Strominger |
| 2007/0292416 A1 | 12/2007 | Rother et al. |
| 2007/0292430 A1 | 12/2007 | Blumenkopf et al. |
| 2008/0009537 A1 | 1/2008 | Sakai |
| 2008/0026378 A1 | 1/2008 | Bottazzo et al. |
| 2008/0044413 A1 | 2/2008 | Hammond et al. |
| 2008/0095766 A1 | 4/2008 | Koenig et al. |
| 2008/0138339 A1 | 6/2008 | Huang et al. |
| 2008/0171014 A1 | 7/2008 | Wu et al. |
| 2008/0171049 A1 | 7/2008 | Yuan |
| 2008/0207594 A1 | 8/2008 | Mussmann et al. |
| 2008/0213288 A1 | 9/2008 | Michelsen et al. |
| 2008/0248055 A1 | 10/2008 | Robertson et al. |
| 2008/0253991 A1 | 10/2008 | Jevnikar et al. |
| 2008/0254040 A1 | 10/2008 | Stefanic et al. |
| 2008/0287423 A1 | 11/2008 | Mussmann et al. |
| 2009/0041769 A1 | 2/2009 | Peach et al. |
| 2009/0117102 A1 | 5/2009 | Cruz |
| 2009/0142338 A1 | 6/2009 | Levetan |
| 2009/0148389 A1 | 6/2009 | Rottiers et al. |
| 2009/0258001 A1 | 10/2009 | Ponath et al. |
| 2009/0269337 A1 | 10/2009 | Brand et al. |
| 2009/0297524 A1 | 12/2009 | Grant et al. |
| 2009/0324609 A1 | 12/2009 | Lodie et al. |
| 2010/0008929 A1 | 1/2010 | van de Winkel et al. |
| 2010/0008932 A1 | 1/2010 | Bensussan et al. |
| 2010/0015142 A1 | 1/2010 | Koenig |
| 2010/0041602 A1 | 2/2010 | Hagerty et al. |
| 2010/0041632 A1 | 2/2010 | Zhang et al. |
| 2010/0047239 A1 | 2/2010 | Wu et al. |
| 2010/0061984 A1 | 3/2010 | Greene et al. |
| 2010/0076178 A1 | 3/2010 | Ghayur et al. |
| 2010/0129357 A1 | 5/2010 | Garcia-Martinez et al. |
| 2010/0129361 A1 | 5/2010 | Ho et al. |
| 2010/0150829 A1 | 6/2010 | Garcia-Martinez et al. |
| 2010/0183554 A1 | 7/2010 | Mach et al. |
| 2010/0183612 A1 | 7/2010 | Peach et al. |
| 2010/0189773 A1 | 7/2010 | Mortimore et al. |
| 2010/0209437 A1 | 8/2010 | Nelson et al. |
| 2010/0247555 A1 | 9/2010 | Self et al. |
| 2010/0260668 A1 | 10/2010 | Ghayur et al. |
| 2011/0002939 A1 | 1/2011 | Melarkode et al. |
| 2011/0020269 A1 | 1/2011 | Strom et al. |
| 2011/0091372 A1 | 4/2011 | Ghayur et al. |
| 2011/0142761 A1 | 6/2011 | Wu et al. |
| 2011/0165066 A1 | 7/2011 | Wu et al. |
| 2011/0165161 A1 | 7/2011 | Lin et al. |
| 2011/0217302 A1 | 9/2011 | Odegard et al. |
| 2011/0250130 A1 | 10/2011 | Benatuil et al. |
| 2011/0256130 A1 | 10/2011 | Schultz et al. |
| 2011/0262440 A1 | 10/2011 | Zugmaier |
| 2011/0263827 A1 | 10/2011 | Ghayur et al. |
| 2011/0280800 A1 | 11/2011 | Wu et al. |
| 2011/0287533 A1 | 11/2011 | Chang |
| 2011/0300142 A1 | 12/2011 | Salford et al. |
| 2012/0014957 A1 | 1/2012 | Ghayur et al. |
| 2012/0045435 A1 | 2/2012 | Deisher |
| 2012/0052065 A1 | 3/2012 | Peach et al. |
| 2012/0076727 A1 | 3/2012 | McBride et al. |
| 2012/0076753 A1 | 3/2012 | Mandelboim et al. |
| 2012/0088678 A1 | 4/2012 | Albani |
| 2012/0195900 A1 | 8/2012 | Ghayur et al. |
| 2012/0201746 A1 | 8/2012 | Liu et al. |
| 2012/0201781 A1 | 8/2012 | Kamath |
| 2012/0230911 A1 | 9/2012 | Hsieh et al. |
| 2012/0237472 A1 | 9/2012 | Kaplin et al. |
| 2012/0258040 A1 | 10/2012 | Exley et al. |
| 2012/0263722 A1 | 10/2012 | Ghayur et al. |
| 2012/0269826 A1 | 10/2012 | McKee et al. |
| 2012/0321623 A1 | 12/2012 | Suciu-Foca et al. |
| 2013/0004416 A1 | 1/2013 | Wu et al. |
| 2013/0039861 A1 | 2/2013 | Regino et al. |
| 2013/0078238 A1 | 3/2013 | Ilan et al. |
| 2013/0095103 A1 | 4/2013 | Baeuerle et al. |

(56)          References Cited

U.S. PATENT DOCUMENTS

| | | |
|---|---|---|
| 2013/0095121 A1 | 4/2013 | Brennan et al. |
| 2013/0115207 A1 | 5/2013 | Faustman |
| 2013/0129723 A1 | 5/2013 | Blankenship et al. |
| 2013/0171142 A1 | 7/2013 | Brennan et al. |
| 2013/0190233 A1 | 7/2013 | Levetan et al. |
| 2013/0225427 A1 | 8/2013 | Albani |
| 2013/0251671 A1 | 9/2013 | Kaufman |
| 2013/0323247 A1 | 12/2013 | Zugmaier et al. |
| 2014/0066600 A1 | 3/2014 | Chang |
| 2014/0088295 A1 | 3/2014 | Smith et al. |
| 2014/0099313 A1 | 4/2014 | Wu et al. |
| 2014/0099318 A1 | 4/2014 | Huang et al. |
| 2014/0112898 A1 | 4/2014 | Mathis |
| 2014/0120097 A1 | 5/2014 | Levetan |
| 2014/0134171 A1 | 5/2014 | Ghayur et al. |
| 2014/0141020 A1 | 5/2014 | Pages et al. |
| 2014/0147413 A1 | 5/2014 | Chen et al. |
| 2014/0193399 A1 | 7/2014 | Mach et al. |
| 2014/0212425 A1 | 7/2014 | Chang et al. |
| 2014/0220020 A1 | 8/2014 | Wu et al. |
| 2014/0220029 A1 | 8/2014 | Michelsen |
| 2014/0234405 A1 | 8/2014 | Levetan |
| 2014/0235552 A1 | 8/2014 | Levetan |
| 2014/0242077 A1 | 8/2014 | Choi et al. |
| 2014/0242081 A1 | 8/2014 | Hammond et al. |
| 2014/0255956 A1 | 9/2014 | Lipes et al. |
| 2014/0271464 A1 | 9/2014 | Garcia-Martinez et al. |
| 2015/0004167 A1 | 1/2015 | Wu et al. |
| 2015/0010508 A1 | 1/2015 | Levetan et al. |
| 2015/0018360 A1 | 1/2015 | Halse et al. |
| 2015/0023977 A1 | 1/2015 | Fraunhofer et al. |
| 2015/0044212 A1 | 2/2015 | Xiao et al. |
| 2015/0050238 A1 | 2/2015 | Kamath |
| 2015/0056167 A1 | 2/2015 | Levetan et al. |
| 2015/0079088 A1 | 3/2015 | Lowman et al. |
| 2015/0079093 A1 | 3/2015 | Stuhler |
| 2015/0086548 A1 | 3/2015 | Levetan |
| 2015/0104452 A1 | 4/2015 | Ghayur et al. |
| 2015/0118252 A1 | 4/2015 | Ho et al. |
| 2015/0125443 A1 | 5/2015 | Crispin et al. |
| 2015/0140007 A1 | 5/2015 | Wang et al. |
| 2015/0141438 A1 | 5/2015 | Kendall |
| 2015/0166661 A1 | 6/2015 | Chen et al. |
| 2015/0174111 A1 | 6/2015 | Levetan |
| 2015/0175699 A1 | 6/2015 | Ellis et al. |
| 2015/0183875 A1 | 7/2015 | Cobbold et al. |
| 2015/0231241 A1 | 8/2015 | Chang et al. |
| 2015/0252110 A1 | 9/2015 | Hansen et al. |
| 2015/0274844 A1 | 10/2015 | Blankenship et al. |
| 2015/0297598 A1 | 10/2015 | Friedman et al. |
| 2015/0299320 A1 | 10/2015 | Exley et al. |
| 2015/0361170 A1 | 12/2015 | Fraunhofer et al. |
| 2016/0039942 A1 | 2/2016 | Cobbold et al. |
| 2016/0046714 A1 | 2/2016 | Koenig et al. |
| 2016/0046730 A1 | 2/2016 | Ghayur et al. |
| 2016/0090416 A1 | 3/2016 | Gunde et al. |
| 2016/0106710 A1 | 4/2016 | Sun et al. |
| 2016/0122436 A1 | 5/2016 | Kufer et al. |
| 2016/0159921 A1 | 6/2016 | D'Angelo et al. |
| 2016/0206682 A1 | 7/2016 | Levetan |
| 2016/0206683 A1 | 7/2016 | Levetan |
| 2016/0213740 A1 | 7/2016 | Levetan |
| 2016/0213741 A1 | 7/2016 | Levetan |
| 2016/0213746 A1 | 7/2016 | Levetan |
| 2016/0215051 A1 | 7/2016 | Sharma et al. |
| 2016/0272703 A1 | 9/2016 | Hsieh et al. |
| 2016/0287622 A1 | 10/2016 | Chang et al. |
| 2016/0289341 A1 | 10/2016 | Wu |
| 2016/0296632 A1 | 10/2016 | Chipman |
| 2016/0311915 A1 | 10/2016 | Pule et al. |
| 2016/0311919 A1 | 10/2016 | Xiao et al. |
| 2016/0317654 A1 | 11/2016 | Noelle et al. |
| 2016/0324798 A1 | 11/2016 | Han et al. |
| 2016/0347850 A1 | 12/2016 | Benatuil et al. |
| 2016/0361360 A1 | 12/2016 | Chang et al. |
| 2017/0015758 A1 | 1/2017 | Hammond et al. |
| 2017/0021017 A1 | 1/2017 | Chang et al. |
| 2017/0022274 A1 | 1/2017 | Chang et al. |
| 2017/0058027 A1 | 3/2017 | Wu et al. |
| 2017/0058043 A1 | 3/2017 | Solman |
| 2017/0073415 A1 | 3/2017 | Urech et al. |
| 2017/0128493 A1 | 5/2017 | Deisher |
| 2017/0137519 A1 | 5/2017 | Huang et al. |
| 2017/0145115 A1 | 5/2017 | Blein et al. |
| 2017/0173117 A1 | 6/2017 | Paulsen et al. |
| 2017/0216218 A1 | 8/2017 | Farokhzad et al. |
| 2017/0218091 A1 | 8/2017 | Ambrosi |
| 2017/0266199 A1 | 9/2017 | Berger et al. |
| 2017/0283446 A1 | 10/2017 | Fan et al. |
| 2017/0304213 A1 | 10/2017 | Shi et al. |
| 2017/0342151 A1 | 11/2017 | Ferrone et al. |
| 2017/0342160 A1 | 11/2017 | Mertens et al. |
| 2017/0362240 A1 | 12/2017 | Allen et al. |
| 2017/0362299 A1 | 12/2017 | Li et al. |
| 2018/0036285 A1 | 2/2018 | Tunac et al. |
| 2018/0057593 A1 | 3/2018 | Dennis |
| 2018/0117152 A1 | 5/2018 | Lee et al. |
| 2018/0134804 A1 | 5/2018 | Scheinberg et al. |
| 2018/0177880 A1 | 6/2018 | Shalibhai |
| 2018/0193477 A1 | 7/2018 | Ng |
| 2018/0237522 A1 | 8/2018 | Snell et al. |
| 2018/0244778 A1 | 8/2018 | Ellis et al. |
| 2018/0251503 A1 | 9/2018 | Ahmed et al. |
| 2018/0273623 A1 | 9/2018 | Cheung et al. |
| 2018/0280507 A1 | 10/2018 | Yu et al. |
| 2018/0291114 A1 | 10/2018 | Ostrand-Rosenberg et al. |
| 2018/0296699 A1 | 10/2018 | Xie |
| 2018/0318230 A1 | 11/2018 | Chopra et al. |
| 2018/0344845 A1 | 12/2018 | Reimann et al. |
| 2018/0346591 A1 | 12/2018 | Soliman |
| 2018/0355064 A1 | 12/2018 | Blein et al. |
| 2019/0004064 A1 | 1/2019 | Chen et al. |
| 2019/0010242 A1 | 1/2019 | Eckelman et al. |
| 2019/0022154 A1 | 1/2019 | Rottiers et al. |
| 2019/0022205 A1 | 1/2019 | Salih et al. |
| 2019/0038733 A1 | 2/2019 | Campana et al. |
| 2019/0046571 A1 | 2/2019 | Campana et al. |
| 2019/0062284 A1 | 2/2019 | Hulme et al. |
| 2019/0070248 A1 | 3/2019 | Sahin et al. |
| 2019/0077856 A1 | 3/2019 | Scheinberg et al. |
| 2019/0135894 A1 | 5/2019 | Ma et al. |
| 2019/0135918 A1 | 5/2019 | Ollier et al. |
| 2019/0153471 A1 | 5/2019 | Paul et al. |
| 2019/0169296 A1 | 6/2019 | Russell et al. |
| 2019/0170752 A1 | 6/2019 | Luo et al. |
| 2019/0184026 A1 | 6/2019 | Li et al. |
| 2019/0185511 A1 | 6/2019 | Kanne et al. |
| 2019/0194690 A1 | 6/2019 | Champion et al. |
| 2019/0233534 A1 | 8/2019 | Mehlin et al. |
| 2019/0233536 A1 | 8/2019 | Champion et al. |
| 2019/0248924 A1 | 8/2019 | Wu |
| 2019/0276541 A1 | 9/2019 | Eavarone et al. |
| 2019/0284296 A1 | 9/2019 | Stuhler |
| 2019/0284299 A1 | 9/2019 | Liu et al. |
| 2019/0292551 A1 | 9/2019 | Rottiers et al. |
| 2019/0300526 A1 | 10/2019 | Fan et al. |
| 2019/0300609 A1 | 10/2019 | Zugmaier et al. |
| 2019/0314417 A1 | 10/2019 | Wobma et al. |
| 2019/0330362 A1 | 10/2019 | Moffat et al. |
| 2019/0343964 A1 | 11/2019 | Akiyama et al. |
| 2019/0351056 A1 | 11/2019 | Christen et al. |
| 2019/0352421 A1 | 11/2019 | Adams et al. |
| 2019/0359732 A1 | 11/2019 | Cheung et al. |
| 2019/0382497 A1 | 12/2019 | Poirier et al. |
| 2020/0023076 A1 | 1/2020 | Fotin-Mleczek et al. |
| 2020/0024363 A1 | 1/2020 | Teran et al. |
| 2020/0040056 A1 | 2/2020 | DiPersio et al. |
| 2020/0040099 A1 | 2/2020 | Kufer et al. |
| 2020/0048356 A1 | 2/2020 | Liu |
| 2020/0071397 A1 | 3/2020 | DiPersio et al. |
| 2020/0079854 A1 | 3/2020 | Hsiue et al. |
| 2020/0087412 A1 | 3/2020 | Fang et al. |
| 2020/0113940 A1 | 4/2020 | Maus et al. |
| 2020/0157218 A1 | 5/2020 | Nathwani et al. |

(56) References Cited

U.S. PATENT DOCUMENTS

| | | |
|---|---|---|
| 2020/0157249 A1 | 5/2020 | Wu |
| 2020/0181260 A1 | 6/2020 | Davila |
| 2020/0181264 A1 | 6/2020 | Rossi et al. |
| 2020/0181288 A1 | 6/2020 | Jang et al. |
| 2020/0199169 A1 | 6/2020 | Leong et al. |
| 2020/0199232 A1 | 6/2020 | Qin et al. |
| 2020/0199248 A1 | 6/2020 | Cheung et al. |
| 2020/0206145 A1 | 7/2020 | Shi et al. |
| 2020/0207851 A1 | 7/2020 | Chen et al. |
| 2020/0216859 A1 | 7/2020 | Champion et al. |
| 2020/0239571 A1 | 7/2020 | Bramson et al. |
| 2020/0261574 A1 | 8/2020 | Reimann et al. |
| 2020/0281976 A1 | 9/2020 | Zeng et al. |
| 2020/0308541 A1 | 10/2020 | Ma et al. |
| 2020/0317809 A1 | 10/2020 | Li |
| 2020/0339679 A1 | 10/2020 | Sirianni et al. |
| 2020/0339686 A1 | 10/2020 | Sato et al. |
| 2020/0384107 A1 | 12/2020 | Yu et al. |
| 2020/0399368 A1* | 12/2020 | Leon ......................... A61P 5/48 |
| 2020/0399370 A1 | 12/2020 | Sahin et al. |
| 2020/0407452 A1 | 12/2020 | Michieli |
| 2021/0000957 A1 | 1/2021 | Shailubhai et al. |
| 2021/0009596 A1 | 1/2021 | Fan et al. |
| 2021/0009691 A1 | 1/2021 | Mach et al. |
| 2021/0024639 A1 | 1/2021 | Michieli |
| 2021/0032333 A1 | 2/2021 | Leon et al. |
| 2021/0038646 A1 | 2/2021 | Maus et al. |
| 2021/0046112 A1 | 2/2021 | Campana et al. |
| 2021/0052612 A1 | 2/2021 | Fan et al. |
| 2021/0085735 A1 | 3/2021 | Finer et al. |
| 2021/0087267 A1 | 3/2021 | Miano et al. |
| 2021/0107985 A1 | 4/2021 | Schuurman et al. |
| 2021/0108213 A1 | 4/2021 | Rashid et al. |
| 2021/0113519 A1 | 4/2021 | Whitehead et al. |
| 2021/0113550 A1 | 4/2021 | Khleif et al. |
| 2021/0113709 A1 | 4/2021 | Demetriou et al. |
| 2021/0130464 A1 | 5/2021 | Leon et al. |
| 2021/0139577 A1 | 5/2021 | Dillon et al. |
| 2021/0139851 A1 | 5/2021 | Chuang et al. |
| 2021/0154247 A1 | 5/2021 | Rottiers et al. |
| 2021/0155713 A1 | 5/2021 | Didonato et al. |
| 2021/0163620 A1 | 6/2021 | Granda et al. |
| 2021/0171661 A1 | 6/2021 | Blein et al. |
| 2021/0177755 A1 | 6/2021 | Dumontet et al. |
| 2021/0180072 A1 | 6/2021 | Rottiers et al. |
| 2021/0188983 A1 | 6/2021 | Robert et al. |
| 2021/0198368 A1 | 7/2021 | Daley et al. |
| 2021/0205248 A1 | 7/2021 | Kaufman et al. |
| 2021/0206853 A1 | 7/2021 | Lindhofer et al. |
| 2021/0214440 A1 | 7/2021 | Ganesan et al. |
| 2021/0214458 A1 | 7/2021 | Liu et al. |
| 2021/0236466 A1 | 8/2021 | Roush et al. |
| 2021/0238291 A1 | 8/2021 | Lowman et al. |
| 2021/0238607 A1 | 8/2021 | Fierabracci |
| 2021/0244815 A1 | 8/2021 | Lee et al. |
| 2021/0246211 A1 | 8/2021 | Goldberg et al. |
| 2021/0251954 A1 | 8/2021 | Sun et al. |
| 2021/0253636 A1 | 8/2021 | Yu et al. |
| 2021/0260173 A1 | 8/2021 | Kjellman et al. |
| 2021/0261645 A1 | 8/2021 | Huang et al. |
| 2021/0261646 A1 | 8/2021 | McGinness et al. |
| 2021/0261649 A1 | 8/2021 | Parry et al. |
| 2021/0269525 A1 | 9/2021 | Yang et al. |
| 2021/0269841 A1 | 9/2021 | Wang et al. |
| 2021/0277127 A1 | 9/2021 | Zhang et al. |
| 2021/0284746 A1 | 9/2021 | Liu et al. |
| 2021/0292423 A1 | 9/2021 | Albrecht et al. |
| 2021/0301015 A1 | 9/2021 | Tseng |
| 2021/0309750 A1 | 10/2021 | Sampson et al. |
| 2021/0324079 A1 | 10/2021 | Cheung et al. |
| 2021/0332134 A1 | 10/2021 | Shibayama et al. |
| 2021/0332334 A1 | 10/2021 | McGinness et al. |
| 2021/0338836 A1 | 11/2021 | Yu et al. |
| 2021/0340219 A1 | 11/2021 | McGinness et al. |
| 2021/0348191 A1 | 11/2021 | Pule et al. |
| 2021/0349094 A1 | 11/2021 | Vasu |
| 2021/0353751 A1 | 11/2021 | Kaufman et al. |
| 2021/0363180 A1 | 11/2021 | Hoang et al. |
| 2021/0363270 A1 | 11/2021 | Park et al. |
| 2021/0371927 A1 | 12/2021 | Gysemans et al. |
| 2021/0379046 A1 | 12/2021 | Scheinberg et al. |
| 2021/0382053 A1 | 12/2021 | Vasiljeva et al. |
| 2021/0386680 A1 | 12/2021 | Cui et al. |
| 2021/0388017 A1 | 12/2021 | Park et al. |
| 2021/0388388 A1 | 12/2021 | Song et al. |
| 2021/0393795 A1 | 12/2021 | Park et al. |
| 2021/0395339 A1 | 12/2021 | Alitalo et al. |
| 2021/0402005 A1 | 12/2021 | Markovic et al. |
| 2022/0002398 A1 | 1/2022 | Thiele et al. |
| 2022/0002407 A1 | 1/2022 | Li et al. |
| 2022/0002408 A1 | 1/2022 | Yuan et al. |
| 2022/0002431 A1 | 1/2022 | Li et al. |
| 2022/0008533 A1 | 1/2022 | Shailubhai |
| 2022/0033427 A1 | 2/2022 | Lourenco et al. |
| 2022/0034903 A1 | 2/2022 | Chen et al. |
| 2022/0041720 A1 | 2/2022 | Leon et al. |
| 2022/0041721 A1 | 2/2022 | Zhang et al. |
| 2022/0041724 A1 | 2/2022 | Twitty et al. |
| 2022/0048961 A1 | 2/2022 | Crook et al. |
| 2022/0056132 A1 | 2/2022 | Qin et al. |
| 2022/0057398 A1 | 2/2022 | Sarvetnick et al. |
| 2022/0073640 A1 | 3/2022 | Moffat et al. |
| 2022/0088196 A1 | 3/2022 | Bauerle et al. |
| 2022/0098307 A1 | 3/2022 | Zhang et al. |
| 2022/0098324 A1 | 3/2022 | Weiner et al. |
| 2022/0098329 A1 | 3/2022 | Santich et al. |
| 2022/0105193 A1 | 4/2022 | Li et al. |
| 2022/0118104 A1 | 4/2022 | Park et al. |
| 2022/0119478 A1 | 4/2022 | Spear et al. |
| 2022/0119549 A1 | 4/2022 | Zhang et al. |
| 2022/0125941 A1 | 4/2022 | Ban et al. |
| 2022/0133887 A1 | 5/2022 | Reimann |
| 2022/0135678 A1 | 5/2022 | Chaudary |
| 2022/0135680 A1 | 5/2022 | Tran et al. |
| 2022/0143291 A1 | 5/2022 | Poirier |
| 2022/0144916 A1 | 5/2022 | Maynard et al. |
| 2022/0144947 A1 | 5/2022 | Smith et al. |
| 2022/0152109 A1 | 5/2022 | Coukos et al. |
| 2022/0152216 A1 | 5/2022 | Sanyal |
| 2022/0153840 A1 | 5/2022 | Qui |
| 2022/0153843 A1 | 5/2022 | Liu et al. |
| 2022/0160887 A1 | 5/2022 | Matray et al. |
| 2022/0160891 A1 | 5/2022 | Green et al. |
| 2022/0160895 A1 | 5/2022 | Iles-Somaratne |
| 2022/0162297 A1 | 5/2022 | Basi |
| 2022/0162335 A1 | 5/2022 | Wang et al. |
| 2022/0168433 A1 | 6/2022 | Matray et al. |
| 2022/0177581 A1 | 6/2022 | Cheung et al. |
| 2022/0177583 A1 | 6/2022 | Conklin et al. |
| 2022/0177600 A1 | 6/2022 | Campbell et al. |
| 2022/0184043 A1 | 6/2022 | Sun et al. |
| 2022/0202950 A1 | 6/2022 | Brahmbhatt et al. |
| 2022/0204621 A1 | 6/2022 | Nathwani et al. |
| 2022/0211870 A1 | 7/2022 | Markovic et al. |
| 2022/0218818 A1 | 7/2022 | Szalay |
| 2022/0218840 A1 | 7/2022 | Kim et al. |
| 2022/0220556 A1 | 7/2022 | Khatri et al. |
| 2022/0235115 A1 | 7/2022 | Li et al. |
| 2022/0235143 A1 | 7/2022 | Spriggs et al. |
| 2022/0242970 A1 | 8/2022 | Davidson et al. |
| 2022/0249566 A1 | 8/2022 | Culshaw et al. |
| 2022/0249696 A1 | 8/2022 | Green et al. |
| 2022/0251200 A1 | 8/2022 | Lewis et al. |
| 2022/0251238 A1 | 8/2022 | Li et al. |
| 2022/0257760 A1 | 8/2022 | Cripe et al. |
| 2022/0265595 A1 | 8/2022 | Cooke et al. |
| 2022/0280440 A1 | 9/2022 | Morales et al. |
| 2022/0298242 A1 | 9/2022 | Yang et al. |
| 2022/0306715 A1 | 9/2022 | Schreiber et al. |
| 2022/0306735 A1 | 9/2022 | Dekosky et al. |
| 2022/0315653 A1 | 10/2022 | Kiefer et al. |
| 2022/0372146 A1 | 11/2022 | Leon |

(56) References Cited

U.S. PATENT DOCUMENTS

| | | |
|---|---|---|
| 2022/0380465 A1 | 12/2022 | Leon et al. |
| 2023/0013752 A1 | 1/2023 | Leon et al. |
| 2023/0382993 A1 | 11/2023 | Leon et al. |

FOREIGN PATENT DOCUMENTS

| | | |
|---|---|---|
| EP | 0613944 A2 | 9/1994 |
| EP | 1515749 | 3/2005 |
| EP | 1591527 | 11/2005 |
| EP | 1687066 | 8/2006 |
| EP | 1691833 | 8/2006 |
| EP | 1753783 | 2/2007 |
| EP | 1697370 B1 | 4/2007 |
| EP | 1697371 B1 | 4/2007 |
| EP | 1397153 B1 | 4/2008 |
| EP | 1686130 B1 | 2/2009 |
| EP | 2037961 | 3/2009 |
| EP | 1379270 B1 | 9/2009 |
| EP | 1337527 B1 | 10/2009 |
| EP | 1837031 B1 | 10/2009 |
| EP | 2093142 | 6/2010 |
| EP | 1716178 B1 | 8/2010 |
| EP | 1827492 B1 | 8/2010 |
| EP | 1697421 B1 | 9/2010 |
| EP | 1673398 B1 | 12/2010 |
| EP | 2270051 | 1/2011 |
| EP | 1451192 B1 | 2/2011 |
| EP | 1798240 B1 | 4/2011 |
| EP | 2397189 | 12/2011 |
| EP | 1879591 B1 | 1/2012 |
| EP | 2288372 B1 | 2/2012 |
| EP | 2096120 B1 | 3/2012 |
| EP | 1578397 B1 | 12/2012 |
| EP | 2119450 B1 | 2/2013 |
| EP | 1973573 B1 | 5/2013 |
| EP | 1797126 B1 | 10/2013 |
| EP | 1613628 B1 | 11/2013 |
| EP | 1740946 B1 | 11/2013 |
| EP | 2164500 B1 | 12/2013 |
| EP | 2408468 B1 | 4/2014 |
| EP | 2714733 | 4/2014 |
| EP | 2755999 | 7/2014 |
| EP | 1976886 B1 | 12/2014 |
| EP | 2814963 | 12/2014 |
| EP | 2344539 B1 | 2/2015 |
| EP | 2892924 | 7/2015 |
| EP | 2342227 B1 | 10/2015 |
| EP | 2551347 B1 | 11/2015 |
| EP | 2295066 B1 | 4/2016 |
| EP | 3024484 | 5/2016 |
| EP | 1957100 B1 | 7/2016 |
| EP | 1976880 B1 | 7/2016 |
| EP | 2292664 B1 | 11/2016 |
| EP | 2029145 B1 | 1/2017 |
| EP | 3464352 B1 | 5/2017 |
| EP | 2066174 B1 | 11/2017 |
| EP | 1629013 B1 | 1/2018 |
| EP | 2854845 B1 | 3/2018 |
| EP | 2793923 B1 | 5/2018 |
| EP | 3024851 B1 | 5/2018 |
| EP | 2835379 B1 | 7/2018 |
| EP | 2764362 B1 | 9/2018 |
| EP | 2878308 B1 | 10/2018 |
| EP | 1629012 B1 | 11/2018 |
| EP | 3129483 B1 | 11/2018 |
| EP | 2968545 B1 | 3/2019 |
| EP | 2982696 B1 | 3/2019 |
| EP | 3330293 B1 | 7/2019 |
| EP | 3087095 B1 | 8/2019 |
| EP | 2993186 B1 | 9/2019 |
| EP | 2793912 B1 | 3/2020 |
| EP | 3044234 B1 | 3/2020 |
| EP | 3083689 B1 | 5/2020 |
| EP | 3186277 B1 | 10/2020 |
| EP | 3227297 B1 | 1/2021 |
| EP | 3791931 A1 | 3/2021 |
| EP | 3318565 B1 | 4/2021 |
| EP | 3402494 B1 | 4/2021 |
| EP | 3402499 B1 | 4/2021 |
| EP | 2819701 B2 | 6/2021 |
| EP | 3310811 B1 | 6/2021 |
| EP | 3504316 B1 | 6/2021 |
| EP | 2242504 B1 | 7/2021 |
| EP | 3268391 B1 | 8/2021 |
| EP | 2742953 B1 | 9/2021 |
| EP | 3297672 B1 | 9/2021 |
| EP | 3389682 B1 | 11/2021 |
| EP | 3439658 B1 | 11/2021 |
| EP | 3194439 B1 | 1/2022 |
| EP | 3230311 B1 | 1/2022 |
| EP | 3703718 B1 | 1/2022 |
| EP | 3434760 B1 | 5/2022 |
| JP | 2016-042024 A | 3/2016 |
| WO | 1990/005541 A1 | 5/1990 |
| WO | 1991/001143 A1 | 2/1991 |
| WO | 1991/004053 A1 | 4/1991 |
| WO | 1991/009966 A1 | 7/1991 |
| WO | 1991/009968 A1 | 7/1991 |
| WO | 1992/000092 A1 | 1/1992 |
| WO | 1992/015671 A1 | 9/1992 |
| WO | 1993/000431 A1 | 1/1993 |
| WO | 1993/019196 A1 | 9/1993 |
| WO | 1993/019767 A1 | 10/1993 |
| WO | 1993/025712 A1 | 12/1993 |
| WO | 1994/023760 A1 | 10/1994 |
| WO | 1994/028912 A1 | 12/1994 |
| WO | 1995/003408 A1 | 2/1995 |
| WO | 1998/047531 A2 | 10/1998 |
| WO | 2001/025398 A2 | 4/2001 |
| WO | 2003/026692 A2 | 4/2003 |
| WO | 2003/102132 A2 | 12/2003 |
| WO | 2003/105896 A1 | 12/2003 |
| WO | 2003/105897 A1 | 12/2003 |
| WO | 2005/076965 A2 | 8/2005 |
| WO | 2007/009064 A2 | 1/2007 |
| WO | 2007/117600 A2 | 10/2007 |
| WO | 2007/145941 A2 | 12/2007 |
| WO | WO2007147090 A2 | 12/2007 |
| WO | 2008/079713 A2 | 7/2008 |
| WO | 2009/029847 A1 | 3/2009 |
| WO | 2014/004857 A1 | 1/2014 |
| WO | 2014138725 A1 | 9/2014 |
| WO | 2014/161918 A1 | 10/2014 |
| WO | WO2014165818 A2 | 10/2014 |
| WO | WO2015073833 | 5/2015 |
| WO | WO2017125897 A1 | 7/2017 |
| WO | 2017/186928 A1 | 11/2017 |
| WO | WO2017193956 A1 | 11/2017 |
| WO | WO2018037416 A1 | 3/2018 |
| WO | WO2018068652 A1 | 4/2018 |
| WO | WO2018115906 A1 | 6/2018 |
| WO | WO2018120842 A1 | 7/2018 |
| WO | WO2018177371 A1 | 10/2018 |
| WO | WO2018178123 A1 | 10/2018 |
| WO | WO2018237192 A1 | 12/2018 |
| WO | WO2019050465 | 3/2019 |
| WO | WO2019091384 A1 | 5/2019 |
| WO | WO2019094669 A2 | 5/2019 |
| WO | WO2019126133 A1 | 6/2019 |
| WO | WO2019133847 A1 | 7/2019 |
| WO | WO2019185864 A1 | 10/2019 |
| WO | WO2019195535 A1 | 10/2019 |
| WO | WO2019204434 A1 | 10/2019 |
| WO | WO2019215772 A1 | 11/2019 |
| WO | WO2019219913 A1 | 11/2019 |
| WO | WO2019222082 A1 | 11/2019 |
| WO | WO2019226894 A1 | 11/2019 |
| WO | WO2019234241 A1 | 12/2019 |
| WO | WO2020001344 A1 | 1/2020 |
| WO | WO2020006486 A1 | 1/2020 |
| WO | WO2020014097 A1 | 1/2020 |
| WO | WO2020028444 A1 | 2/2020 |
| WO | WO2020047176 A1 | 3/2020 |
| WO | WO2020053301 A1 | 3/2020 |

(56) References Cited

FOREIGN PATENT DOCUMENTS

| | | | |
|---|---|---|---|
| WO | WO2020056037 | A1 | 3/2020 |
| WO | WO2020056170 | A1 | 3/2020 |
| WO | WO2020081885 | A1 | 4/2020 |
| WO | WO2020081886 | A1 | 4/2020 |
| WO | WO2020086423 | A1 | 4/2020 |
| WO | WO2020089396 | A2 | 5/2020 |
| WO | WO2020092743 | A2 | 5/2020 |
| WO | WO2020112987 | A1 | 6/2020 |
| WO | WO2020113164 | A1 | 6/2020 |
| WO | WO2020123806 | A1 | 6/2020 |
| WO | WO2020124032 | A1 | 6/2020 |
| WO | WO2020160310 | A1 | 8/2020 |
| WO | WO2020168554 | A1 | 8/2020 |
| WO | WO2020168555 | A1 | 8/2020 |
| WO | WO2020172259 | A1 | 8/2020 |
| WO | WO2020185763 | A1 | 9/2020 |
| WO | WO2020186974 | A1 | 9/2020 |
| WO | WO2020190217 | A1 | 9/2020 |
| WO | WO2020191344 | A1 | 9/2020 |
| WO | WO2020191486 | A1 | 10/2020 |
| WO | WO2020206063 | A1 | 10/2020 |
| WO | WO2020210232 | A1 | 10/2020 |
| WO | WO2020210843 | A2 | 10/2020 |
| WO | WO2020214928 | A1 | 10/2020 |
| WO | 2020232247 | A1 | 11/2020 |
| WO | WO2020222010 | A1 | 11/2020 |
| WO | WO2020222011 | A1 | 11/2020 |
| WO | WO2020223279 | A1 | 11/2020 |
| WO | WO2020226854 | A2 | 11/2020 |
| WO | WO2020227538 | A1 | 11/2020 |
| WO | WO2020229553 | A1 | 11/2020 |
| WO | WO2020247385 | A1 | 12/2020 |
| WO | WO2020247867 | A1 | 12/2020 |
| WO | WO2020247871 | A1 | 12/2020 |
| WO | WO2021001458 | A1 | 1/2021 |
| WO | WO2021016316 | A1 | 1/2021 |
| WO | 2021/035054 | A1 | 2/2021 |
| WO | WO2021038975 | A1 | 3/2021 |
| WO | WO2021041725 | A1 | 3/2021 |
| WO | WO2021041958 | A1 | 3/2021 |
| WO | WO2021044008 | A1 | 3/2021 |
| WO | WO2021048724 | A1 | 3/2021 |
| WO | WO2021060638 | A1 | 4/2021 |
| WO | WO2021064069 | A1 | 4/2021 |
| WO | WO2021071319 | A1 | 4/2021 |
| WO | WO2021072264 | A1 | 4/2021 |
| WO | WO2021090321 | A1 | 5/2021 |
| WO | WO2021092672 | A1 | 5/2021 |
| WO | WO2021110935 | A1 | 6/2021 |
| WO | WO2021111185 | A1 | 6/2021 |
| WO | WO2021116398 | A1 | 6/2021 |
| WO | WO2021119585 | A1 | 6/2021 |
| WO | WO2021127489 | A1 | 6/2021 |
| WO | WO2021130492 | A1 | 7/2021 |
| WO | WO2021138600 | A1 | 7/2021 |
| WO | WO2021144315 | A1 | 7/2021 |
| WO | WO2021146328 | A1 | 7/2021 |
| WO | WO2021155071 | A1 | 8/2021 |
| WO | WO2021165248 | A1 | 8/2021 |
| WO | WO2021173783 | A1 | 9/2021 |
| WO | WO2021183839 | A2 | 9/2021 |
| WO | WO2021188590 | A2 | 9/2021 |
| WO | WO2021195067 | A1 | 9/2021 |
| WO | WO2021202726 | A2 | 10/2021 |
| WO | WO2021202770 | A2 | 10/2021 |
| WO | WO2021207828 | A1 | 10/2021 |
| WO | WO2021213421 | A1 | 10/2021 |
| WO | WO2021216460 | A1 | 10/2021 |
| WO | WO2021216972 | A1 | 10/2021 |
| WO | WO2021222746 | A2 | 11/2021 |
| WO | WO2021222861 | A1 | 11/2021 |
| WO | 2021252917 | A2 | 12/2021 |
| WO | WO2021243206 | A1 | 12/2021 |
| WO | WO2021252780 | A2 | 12/2021 |
| WO | WO2021254574 | A2 | 12/2021 |
| WO | WO2022013872 | A1 | 1/2022 |
| WO | WO2022018262 | A1 | 1/2022 |
| WO | WO2022026439 | A2 | 2/2022 |
| WO | WO2022026939 | A2 | 2/2022 |
| WO | WO2022027039 | A1 | 2/2022 |
| WO | WO2022029438 | A1 | 2/2022 |
| WO | WO2022032004 | A2 | 2/2022 |
| WO | WO2022033419 | A2 | 2/2022 |
| WO | WO2022035888 | A2 | 2/2022 |
| WO | WO2022036495 | A1 | 2/2022 |
| WO | WO2022037520 | A1 | 2/2022 |
| WO | WO2022038365 | A2 | 2/2022 |
| WO | WO2022040429 | A2 | 2/2022 |
| WO | WO2022040603 | A2 | 2/2022 |
| WO | WO2022045247 | A1 | 3/2022 |
| WO | WO2022053036 | A1 | 3/2022 |
| WO | WO2022058298 | A1 | 3/2022 |
| WO | WO2022060832 | A1 | 3/2022 |
| WO | WO2022063302 | A1 | 3/2022 |
| WO | WO2022067224 | A1 | 3/2022 |
| WO | 2022/087149 | A2 | 4/2022 |
| WO | WO2022076898 | A1 | 4/2022 |
| WO | WO2022077108 | A1 | 4/2022 |
| WO | WO2022083853 | A1 | 4/2022 |
| WO | WO2022090714 | A1 | 5/2022 |
| WO | WO2022090723 | A1 | 5/2022 |
| WO | WO2022090724 | A1 | 5/2022 |
| WO | WO2022098771 | A1 | 5/2022 |
| WO | WO2022099032 | A1 | 5/2022 |
| WO | WO2022099076 | A1 | 5/2022 |
| WO | WO2022105787 | A1 | 5/2022 |
| WO | WO2022115474 | A1 | 6/2022 |
| WO | WO2022115719 | A1 | 6/2022 |
| WO | WO2022116480 | A1 | 6/2022 |
| WO | WO2022125482 | A1 | 6/2022 |
| WO | WO2022125566 | A1 | 6/2022 |
| WO | WO2022129910 | A1 | 6/2022 |
| WO | WO2022132929 | A2 | 6/2022 |
| WO | WO2022148736 | A1 | 7/2022 |
| WO | WO2022157352 | A1 | 7/2022 |
| WO | WO2022159555 | A1 | 7/2022 |
| WO | WO2022162192 | A1 | 8/2022 |
| WO | WO2022164935 | A1 | 8/2022 |
| WO | WO2022167689 | A1 | 8/2022 |
| WO | WO2022169825 | A1 | 8/2022 |
| WO | WO2022179004 | A1 | 9/2022 |
| WO | WO2022183018 | A1 | 9/2022 |
| WO | WO2022187586 | A1 | 9/2022 |
| WO | WO2022192236 | A1 | 9/2022 |
| WO | WO2022194264 | A1 | 9/2022 |
| WO | WO2022195241 | A1 | 9/2022 |
| WO | WO2022197907 | A1 | 9/2022 |
| WO | WO2022199555 | A1 | 9/2022 |
| WO | 2022251253 | A1 | 12/2022 |
| WO | 2022251258 | A1 | 12/2022 |
| WO | 2023039295 | A1 | 3/2023 |
| WO | 2023044495 | A1 | 3/2023 |
| WO | 2023/230476 | A1 | 11/2023 |
| WO | 2024/182767 | A1 | 9/2024 |
| WO | 2024/206739 | A1 | 10/2024 |

OTHER PUBLICATIONS

Sims et al., "Teplizumab Improves and Stabilizes Beta Cell Function in Antibody-Positive High-Risk Individuals," Science Translational Medicine, vol. 13, No. 8980, pp. 1-14, Mar. 3, 2021.

Provention Bio, Inc., "Recent-Onset Type 1 Diabetes Trial Evaluating Efficacy and Safety of Teplizumab (Protect)", Clinical Trials. gov, https://clinicaltrials.gov/ct2/show/NCT03875729, Nov. 15, 2021.

International Search Report in International Patent Application No. PCT/US2022/030772 mailed Sep. 1, 2022.

American Diabetes Association, "2. Classification and Diagnosis of Diabetes: Standards of Medical Care in Diabetes—2019" Diabetes Care, vol. 42, Suppl. 1, pp. S13-S28, Jan. 2019.

Anonymous: "Anti-CD3 Prevention ANTI-CD3 Mab (Teplizumab) for Prevention of Diabetes in Relatives at-risk for type 1 Diabetes Mellitus (Protocol Tn-10", Type 1 Diabetes TrialNet, Protocol

(56) References Cited

OTHER PUBLICATIONS

Version Jun. 25, 2014, https://clinicaltrials.gov/ProvidedDocs/61/NCT01030861/Prot_000.

Atkinson et al., "The Challenge of Modulating Beta-Cell Autoimmunity in Type 1 Diabetes" Lancet Diabetes Endocrinol, vol. 7, pp. 52-64, 2019.

Bingley et al., "Type 1 Diabetes TrialNet: A Multifaceted Approach to Bringing Disease-Modifying Therapy to Clinical Use in Type 1 Diabetes" Diabetes Care, vol. 41, pp. 653-661, Apr. 2018.

Cox D., "Regression Models and Life Tables" Journal of the Royal Statistical Society, Series B, vol. 34, No. 2, pp. 187-220, 1972.

Dayan et al., "Changing the Landscape for Type 1 Diabetes: The First Step to Prevention" Lancet, vol. 394, pp. 1286-1296, Oct. 5, 2019.

Demeester et al., "Preexisting Insulin Autoantibodies Predice Efficacy of Otelixizumab in Preserving Residual beta-Cell Function in Recent-Onset Type 1 Diabetes" Diabetese Care, vol. 3, No. 4, pp. 644-651, Apr. 2015.

Diabetes Study Group, "Effects of Insulin in Relatives of Patients with Type 1 Diabetes Mellitus" New England Journal of Medicine, vol. 346, No. 22, pp. 1685-1691, May 30, 2002.

Espluges et al., "Control of TH17 Cells Occurs in the Small Intestine" Nature, vol. 475, pp. 514-520, Jul. 28, 2011.

Gale et al., "European Nicotinamide Diabetes Intervention Trial (ENDIT): A Randomised Controlled Trial of Intervention Before the Onset of Type 1 Diabetes" Lancet, vol. 363, pp. 925-931, Mar. 20, 2004.

Greenbaum et al., "Fall in C-Peptide During First 2 Years from Diagnosis: Evidence of at Least Two Distinct Phases from Composite TrialNet Data" Diabetes, vol. 61, pp. 2066-2073, Aug. 2012.

Hagopian et al., "Teplizumab Preserves C-Peptide in Recent-Onset Type 1 Diabetes—Two-Year Results from the Randomized, Placebo-Controlled Protégé Trial" Diabetes, vol. 62, pp. 3901-3908, Nov. 2013.

Herold et al., "Anti-CD3 Monoclonal Antibody in New-Onset Type 1 Diabetes Mellitus" New England Journal of Medicine, vol. 346, pp. 1692-1698, May 30, 2002.

Herold et al., "A Single Course of Anti-CD3 Monoclonal Antibody hOKT3γ1(Ala-Ala) Results in Improvement in C-Peptide Responses and Clinical Parameters for at Least 2 Years after Onset of Type 1 Diabetes" Diabetes, vol. 54, pp. 1763-1769, Jun. 2005.

Herold et al., Activation of Human T Cells by FcR Nonbinding Anti-CD3 mAb, hOKT3 gamma1 (Ala-Ala), Journal of Clinical Investigation, vol. 111, No. 3, pp. 409-418, Feb. 2003.

Herold et al., "An Anti-CD3 Antibody, Teplizumab, in Relatives at Risk for Type 1 Diabetes" The New England Journal of Medicine, vol. 381, No. 7, pp. 603-613, Aug. 15, 2019.

Herold et al., "Beta Cell Death and Dysfunction During Type 1 Diabetes Development in At-Risk Individuals" Journal of Clinical Investigation, vol. 125, No. 3, pp. 163-1173, Mar. 2015.

Herold et al., "Teplizumab (Anti-CD3 mAb) Treatment Preserves C-Peptide Responses in Patients With New-Onset Type 1 Diabetes in a Randomized Control Trial" Diabetes, vol. 62, pp. 3766--3774, Nov. 2013.

Herold et al., "Teplizumab Treatment May Improve C-Peptide Responses in Participants with Type 1 Diabetes after the New-Onset Period: A Randomised Controlled Trial", Diabetologia, vol. 6, pp. 391-400, Oct. 21, 2012.

Hippich et al., "Genetic Contribution to the Divergence in Type 1 Diabetes Risk Between Children From the General Population and Children from Affected Families" Diabetes, vol. 68,pp. 847-857, Apr. 2019.

Insel et al., "Staging Presymptomatic Type 1 Diabetes: A Scientific Statement of JDRF, the Endocrine Society, and the American Diabetes Association" Diabetes Care, vol. 38, pp. 1964-1974, Oct. 2015.

Keymeulen et al., "Insulin Needs After CD3-Antibody Therapy in New-Onset Type 1 Diabetes" Lancet Diabetes Endocrinol, vol. 7, pp. 52-64, 2019.

Kuhn et al., "Therapeutic Anti-CD3 Monoclonal Antibodies: From Bench to Bedside" Immunotherapy, vol. 8, No. 8, pp. 889-906, May 10, 2016.

Lan et al., Discrete Sequential Boundaries for Clinical Trials, Biometrika, vol. 70, No. 3, pp. 659-663, Dec. 1983.

Livingstone et al., "Estimated Life Expectancy in a Scottish Cohort with Type 1 Diabetes" JAMA, vol. 313, No. 1, pp. 37-44, Jan. 6, 2015.

Long et al., "Partial Exhaustion of CD8 T Cells and Clinical Response to Teplizumab in New-Onset Type 1 Diabetes" Science Immunology, vol. 1, No. 5, Abstract Article eaai7793.

Mannering et al., "The Case for an Autoimmune Aetiology of Type 1 Diabetes", Clinical and Experimental Immunology, Wiley-Blackwell Publishing Ltd., GB, vol. 183, No. 1, pp. 8-15, Oct. 21, 2015.

Mantel et al., "Evaluation of Suvival Data and Two New Rank Order Statistics Arising in its Consideration" Cancer Chemotherapy Reports, vol. 50, No. 3, Mar. 1966.

Menke et al., "The Prevalence of Type 1 Diabetes in the United States" Epidemiology, vol. 24, No. 5, pp. 773-774, Sep. 2013.

Miller et al., "Current State of Type 1 Diabetes Treatment in the United States" Diabetes Care, vol. 38, pp. 971-997A268, Jun. 2015.

Noble et al., "Genetics of the HLA Region in the Prediction of Type 1 Diabetes", Current Diabetes Reports, Current Science, Inc., vol. 11, No. 6, pp. 533-542, Sep. 13, 2011.

Perdigoto et al., "Treatment of Type 1 Diabetes with Teplizumab: Clinical and Immunological Follow-Up after 7 Years from Diagnosis" Diabetologia, vol. 62, No. 4, pp. 655-664, Apr. 2019.

Rawshani et al., "Excess Mortality and Cardiovascular Disease in Young Adults with Type 1 Diabetes in Relation to Age at Onset: a Nationwide, Register-Based Cohort Study" Lancet vol. 392, pp. 477-486, Aug. 11, 2018.

Schoenfeld, "Sample-size Formula for the Proportional-Hazards Regression Model" Biometrics, vol. 39, No. 2, pp. 499-503, Jun. 1983.

Sherry et al., "Teplizumab for Treatment of Type 1 Diabetes (Protégé Study): 1-Year Results from a Randomised, Placebo-Controlled Trial" Lancet, vol. 378, Issue 9790, pp. 487-497, Aug. 6, 2011.

Skowera et al., "beta-Cell-Specific CD8 T Cell Phenotype in Type 1 Diabetes Reflects Chronic Autoantigen Exposure", Diabetes, vol. 64, No. 3, pp. 916-926, Mar. 2015.

Therneau et al., "Modeling Survival Data: Extending the Cox Model" . Statistics for Biology and Health. Springer, New York, NY pp. 39-77, https://doi.org/10.1007/978-1-4757-3294-8_3 This is a Book Chapter—Available to purchase for $29.95 if necessary.

Tooley et al., "Changes in T-Cell Subsets Identify Responders to FcR Non-Binding Anti-CD3 mAb (teplizumab) in Patients with Type 1 Diabetes" European Journal of Immunology, vol. 46, pp. 230-241, Jan. 2016.

Waldron-Lynch et al., "Teplizumab Induces Human Gut-Tropic Regulatory Cells in Humanized Mice and Patients" Science Translational Medicine, vol. 4, Issue 118, pp. 1-29, Jan. 25, 2012.

Wherrett et al., "Defining Pathways for Development of Disease-Modifying Therapies in Children With Type 1 Diabetes: A Consensus Report" Diabetes Care, vol. 38, pp. 1975-1985, Oct. 2015.

Wherrett et al., "Prevention of Type 1 Diabetes" Endocrinology and Metabolism Clinics of North America, vol. 38, No. 4, pp. 777-792, Dec. 1, 2009.

Wherry et al., "Molecular Signature of CD8+ T Cell Exhaustion During Chronic Viral Infection" Immunity, vol. 27, pp. 670-684, Oct. 2007.

Wherry, "T Cell Exhaustion" Nature Immunology, vol. 12, No. 6, pp. 492-498, Jun. 2011.

Wu et al., "Risk Factors and Primary Prevention Trials for Type 1 Diabetes", International Journal of Biological Sciences, vol. 9, No. 7, pp. 666-679, Jul. 18, 2013.

Wenzlau et al., "The Cation Efflux Transporter ZnT8 (Slc3A8) is a Major Autoantigen in Human Type 1 Diabetes" PNAS, vol. 104, No. 43, p. 17040-17045, Oct. 23, 2007.

U.S. Appl. No. 17/345,495, filed Jun. 11, 2021, Francisco Leon.

U.S. Appl. No. 17/752,650, filed May 24, 2022, Francisco Leon.

U.S. Appl. No. 17/929,573, filed Sep. 2, 2022, Francisco Leon.

(56) References Cited

OTHER PUBLICATIONS

U.S. Appl. No. 18/321,964, filed May 23, 2023, Francisco Leon.
U.S. Appl. No. 18/691,228, filed Mar. 12, 2024, Francisco Leon.
U.S. Appl. No. 18/693,879, filed Mar. 20, 2024, Francisco Leon.
"Effect of Intensive Therapy on Residual β-Cell Function in Patients with Type 1 Diabetes in the Diabetes Control and Complications Trial: A Randomized, Controlled Trial," Ann Intern Med. (1998) 128(7):517-23.
DCCT (Diabetes Control and Complications Trial Research Group), "The Effect of Intensive Treatment of Diabetes on the Development and Progression of Long-Term Complications in Insulin-Dependent Diabetes Mellitus," (1993) N. Engl. J. Med. 329:977-86.
Isaacs et al., "Study Design and Key Findings from Teplizumab Clinical Trials in Type 1 Diabetes," (2023).
Keymeulen et al., "A Randomised, Single-blind, Placebo-controlled, Dose-finding Safety and Tolerability Study of the Anti-CD3 Monoclonal Antibody Otelixizumab in New-onset Type 1 Diabetes," Diabetologia (2021) 64(2):313-24.
Leung, et al., "Expansion of Functional Regulatory T Cells Using Soluable RAGE Prevents Type 1 Diabetes," bioRxiv (2020).
Long, et al., "Remodeling T Cell Compartments during Anti-CD3 Immunotheraphy of Type 1 Diabetes," Cellular Immunology (2017) 319:3-9.
Ovalle, et al., "Verapamil and Beta Cell Function in Adults With Recent-onset Type 1 Diabetes", Nature Medicine (2018) 24(8):1108-12.
Unsworth et al., "New-Onset Type 1 Diabetes in Children During COVID-19: Multicenter Regional Findings in the U.K.," Diabetes Care 1 (2020) 43(11):e170-71.
Brown et al., "unknown," Current Opinion in Investigational Drugs (2006) 7(4):381-388 (Abstract only).
Friend et al., "Phase I Study of An Engineered Aglycosylated Humanized CD3 Antibody in Renal Transplant Rejection," Transplantation (1999) 68(11):1625-6.
Leslie et al., "Type 1 Diabetes and Latent Autoimmune Diabetes in Adults: One End of the Rainbow," JCEM (2006) 91(5):1654-9.
Mahon et al., "TrialNet Natural History, G. Type 1 Diabetes TrialNet Study, The TrialNet Natural History Study of the Development of Type 1 Diabetes: objectives, design, and initial results," Pediatr Diabetes. (2009) 10:97-104.
Naik, et al., "Latent Autoimmune Diabetes in Adults," J. Clin. Endocrinol. Metab. (2009) 94(12):4635-44.
Tsai et al., "The Rise and Fall of Insulin Secretion in Type 1 Diabetes Mellitus," Diabetologia. (2006) 49:261-70.
US Department of Health, "General Considerations for the Clinical Evaluation of Drugs," HEW Publication No. FDA 77-3040, (1997).
Van Cauter et al., "Estimation of Insulin Secretion Rates From C-Peptide Levels. Comparison Of Individual and Standard Kinetic Parameters For C-Peptide Clearance," Diabetes (1992) 41:368-77.
Von Herrath et al., "Non Mitogenic CD3 Antibody Reverses Virally Induced (Rat Insulin Promoter-Lymphocyte Choriomeningitis Virus) Autoimmune Diabetes Without Impeding Viral Clearance," J. Immunol. (2002) 168(2):933-41.
Yu et al., "Type 1 Diabetes TrialNet Study, Zinc Transporter-8 Autoantibodies Improve Prediction of Type 1 Diabetes in Relatives Positive for the Standard Biochemical Autoantibodies," (2012) Diabetes Care. 35:1213-18.
Ziegler et al., "Seroconversion to Multiple Islet Autoantibodies and Risk of Progression to Diabetes in Children," Jama. (2013) 309:2473-79.
Eizirik et al., "The Role of Inflammation in Insulitis and Beta-Cell Loss in Type 1 Diabetes," Nat Rev Endocrinol, (2009) 5:219-26.
Perdigoto et al., "N. Immune Tolerance, Treatment of Type 1 Diabetes with Teplizumab: Clinical and Immunological Follow-Up After 7 Years from Diagnosis," (2019) Diabetologia. 62:655-64.
Dean et al., "Combination therapies in the context of anti-CD3 antibodies for the treatment of autoimmune diseases," Swiss Medical Weekly (2012):11 pages.

Herold, et al., "Treatment of patients with new onset Type 1 diabetes with a single course of anti-CD3 mAb teplizumab preserves insulin production for up to 5 years," Clinical Immunology (2009) 132(2):166-73.
Masharani et al., "Teplizumab therapy for type 1 diabetes," Expert Opinion on Biological Therapy (2010) 10(3):459-65.
Michalakis, et al., "COVID-19 and Hyperglycemia/diabetes,"World Journal of Diabetes (2021) 12(5):642-50.
Van Der Werf et al., "Viral Infections as Potential Triggers of Type 1 Diabetes", Diabetes/Metabolism Research And Reviews (2006) 23(3):169-183.
U.S. Appl. No. 18/666,000, filed Aug. 29, 2024, Francisco Leon.
Achenbach et al., "Modulating the Autoimmune Response in Type 1 Diabetes," The Review of Diabetic Studies (2004) 1(3):137-40.
Battaglia et al., "Understanding and Preventing Type 1 Diabetes Through the Unique Working Model of TrialNet," Diabetologia (2017) 60:2139-47.
Bogun et al., "C-Peptide Levels in Subjects Followed Longitudinally Before and After Type 1 Diabetes Diagnosis in TrialNet," Diabetes Care (2020) 43:1-8.
Bresson et al., "Immunotherapy After Recent-Onset Type 1 Diabetes: Combinatorial Treatment for Achieving Long-Term Remission in Humans?" The Review of Diabetic Studies (2004) 1(3):108-12.
Bresson et al., "Limitations in Immunotherapy with CD3 Antibodies: Comment on the Article by Drs. Chatenoud and Bach," The Review of Diabetic Studies (2005) 2(4):187-9.
Brutsaert, "Diabetes Mellitus (DM)," Merck Manual (2024) https://www.merckmanuals.com/professional/endocrine-and-metabolic-disorders/diabetes-mellitus-and-disorders-of-carbohydrate-metabolism/diabetes-mellitus-dm.
Ceuppens et al., "Failures of OKT3 Monoclonal Antibody to Induce Lymphocyte Mitogenesis: A Familial Defect in Monocyte Helper Function," The Journal of Immunology (1985) 134(3):1498-502.
Chatenoud et al., "Anti-CD3 Antibody Induces Long-Term Remission of Overt Autoimmunity in Nonobese Diabetic Mice," Proc. Natl. Acad. Sci. (1994) 91:123-8.
Chatenoud et al., "CD3 Antibody-Induced Dominant Self Tolerance in Overtly Diabetic NOD Mice," J Immunol. (1997) 158:2947-54.
Chatenoud et al., "Questioning Four Preconceived Ideas on Immunotherapy of Clinical Type 1 Diabetes: Lessons from Recent CD3 Antibody Trials," The Review of Diabetic Studies (2005) 2(3):116-20.
Chekalin et al., "Peculiarities of Age-related Pharmacokinetics in Children," Pediatrics (2005) N3:63-66. Found on the Internet: <URL: https://pediatriajournal.ru/files/upload/mags/268/2005_3_1363.pdf.
Davidson et al., "An Alternative Approach to The Diagnosis of Diabetes with A Review of the Literature," Diabetes Care (1995) 18:1065-71.
Eli Lilly, "MacroGenics and Lilly Announce Pivotal Clinical Trial of Teplizumab Did Not Meet Primary Efficacy Endpoint," Oct. 20, 2010, https://investor.lilly.com/news-releases/news-release-details/macrogenics-and-lilly-announce-pivotal-clinical-trial-teplizumab.
Evans-Molina et al., "Beta Cell Dysfunction Exists More than 5 Years Before Type 1 Diabetes Diagnosis," JCI Insight (2018):1-10.
Ferrannini et al., "Progression to Diabetes in Relatives of Type 1 Diabetic Patients: Mechanisms and Mode of Onset," Diabetes (2010) 59:679-85.
Foster et al., "State of Type 1 Diabetes Management and Outcomes from the T1D Exchange in 2016-2018," Diabetes Technol. Ther. (2019) 21:66-72.
Greenbaum et al., "Preservation of Beta-Cell Function in Autoantibody-Positive Youth with Diabetes," Diabetes Care (2009) 32:1839-44.
Greenbaum et al., "Strength in Numbers Opportunities for Enhancing the Development of Effective Treatments for Type 1 Diabetes—The TrialNet Experience," Diabetes (2018) 67:1216-25.
Grineva et al. "New Technologies in Prevention and Treatment of Diabetes Type 1," Translational Medicine (2014) 4:5-10.
Grogan, "GSK/Tolerx Type 1 Diabetes Drug Fails in Phase III," https://pharmatimes.com/news/gsktolerx_type_1_diabetes_drug_fails_in_phase_iii_979443/ (2011).
GSK, "GlaxoSmithKline and Tolerx Announce Phase III DEFEND-1 Study of Otelixizumab in Type 1 Diabetes Did Not Meet its Primary

(56) References Cited

OTHER PUBLICATIONS

Endpoint," Mar. 11, 2011, https://www.gsk.com/en-gb/media/press-releases/glaxosmithkline-and-tolerx-announce-phase-iii-defend-1-study-of-otelixizumab-in-type-1-diabetes-did-not-meet-its-primary-endpoint/.

Havran et al., ""Expression and Function of the CD3-Antigen Receptor on Murine CD4+8+ Thymocytes,"" Nature (1987) 330(12):170-3.

Hering et al., "Transplantation of Cultured Islets from Two-Layer Preserved Pancreases in Type 1 Diabetes with Anti-CD3 Antibody," American Journal of Transplantation (2004) 4(3):390-401.

Herold et al., "Prevention of Autoimmune Diabetes with Nonactivating Anti-CD3 Monoclonal Antibody," Diabetes (1992) 41:385-91.

Herold et al., "Immunomodulatory Activity of Humanized Anti-IL-7R Monoclonal Antibody RN168 in Subjects with Type 1 Diabetes," JCI Insight (2019):1-16.

Herold et al., "Anti-CD3 Monoclonal Antibody in New-Onset Type 1 Diabetes Mellitus," N Engl J Med. (2002) 346(22):1692-8.

Herold, "Anti-CD3 (Teplizumab) for Prevention of Diabetes in Relatives At-risk for Type 1 Diabetes Mellitus," Protocol TN10 Manual of Operations Version 3.0 (2013).

Herold, et al., "Teplizumab: A Disease-Modifying Therapy for Type 1 Diabetes That Preserves β-Cell Function," Diabetes Care (2023) 46(10):1848-56.

Keymeulen et al., "Insulin Needs After CD3-Antibody Therapy in New-Onset Type 1 Diabetes," N Engl J Med. (2005) 352:2598-608.

Koskinen et al., "Reduced β-cell Function in Early Preclinical Type 1 Diabetes," European Journal of Endocrinology (2016) 174:251-9.

Krischer et al., "Effect of Oral Insulin on Prevention of Diabetes in Relatives of Patients with Type 1 Diabetes: A Randomized Clinical Trial," JAMA (2017) 318:1891-902.

Krischer et al., "Genetic and Environmental Interactions Modify the Risk of Diabetes-Related Autoimmunity by 6 Years of Age: The TEDDY Study," Diabetes Care (2017) 40:1194-202.

Medline Plus, "Autoimmune Disorders," https://medlineplus.gov/ency/article/000816.htm (2023).

Nathan et al., "Dysglycemia and Index60 as Prediagnostic End Points for Type 1 Diabetes Prevention Trials," Diabetes Care (2017) 40:1494-9.

Norman et al., "Phase I Trial of HuM291, A Humanized Anti-CD3 Antibody, in Patients Receiving Renal Allografts from Living Donors," Transplantation (2000) 70(12):1707-12.

Palmer et al., "Is Latent Autoimmune Diabetes in Adults Distinct from Type 1 Diabetes or Just Type 1 Diabetes at an Older Age?" Diabetes (2005) 54(Supplement 2):S62-7.

Palmer, "C-peptide in the Natural History of Type 1 Diabetes," Diabetes Metab Res Rev. (2009) 25:325-8.

Polonsky et al., "Use of Biosynthetic Human C-Peptide in The Measurement of Insulin Secretion Rates in Normal Volunteers and Type I Diabetic Patients," J Clin Invest. (1986) 77:98-105.

Ramos et al., "Teplizumab and β-Cell Function in Newly Diagnosed Type 1 Diabetes," The New England Journal of Medicine (2023) 389(23):2151-61.

Renders et al., "Engineered CD3 Antibodies for Immunosuppression," Clin. Exp. Immunol. (2003) 133:307-9.

Sherry et al., "Effects of Autoimmunity and Immune Therapy on Beta-Cell Turnover in Type 1 Diabetes," Diabetes (2006) 55:3238-45.

Sherry et al., "Teplizumab for Treatment of Type 1 Diabetes (Protege Study): 1-Year Results from a Randomised, Placebo-Controlled Trial," Lancet (2011) 378:487-97.

Siljander et al., "Insulin Secretion and Sensitivity in The Prediction of Type 1 Diabetes in Children with Advanced Beta-Cell Autoimmunity," Eur J Endocrinol. (2013) 169:479-503.

Sims et al., "Cause or effect? A Review of Clinical Data Demonstrating Beta Cell Dysfunction Prior To The Clinical Onset of Type 1 Diabetes," Mol Metab. (2019) 27S:S129-38.

Skyler, "Prevention and Reversal of Type 1 Diabetesd-Past Challenges and Future Opportunities," Diabetes Care (2015) 38:997-1007.

Sosenko et al., "Incident Dysglycemia and Progression to Type 1 Diabetes Among Participants in the Diabetes Prevention Trial-Type 1," Diabetes Care (2009) 32(9):1603-7.

Sosenko et al., "Patterns of Metabolic Progression to Type 1 Diabetes in the Diabetes Prevention Trial-Type 1," Diabetes Care (2006) 29:643-9.

Steele et al., "Insulin Secretion in Type 1 Diabetes," Diabetes (2004) 53:426-33.

Stenstrom et al., "Latent Autoimmune Diabetes in Adults: Definition, Prevalence, β-Cell Function, and Treatment," Diabetes (2005) 54(2):S68-72.

Tao et al., "Estimating the Cost of Type 1 Diabetes in the U.S.: A Propensity Score Matching Method," PLoS One (2010) 5(7)e11501:1-11.

Herold et al., "Treatment of Type 1 Diabetes with Anti-CD3 Monoclonal Antibody," Immunologic Research (2000) 28(2):141-50.

Herold et al., "Treatment with hOKT3g1 (Ala-Ala) Improves Insulin Responses and Reduces Insulin Requirements in PTS with New Onset Type 1 Diabetes (T1DM)," Diabetes (2004) 53(2):A63.

Herold et al., "452 Metabolic Parameters at Baseline Identify Clinical Responders to Teplizumab 2 Years After Diagnosis of Type 1 Diabetes," 48th Annual Meeting of the European Association for the Study of Diabetes (2012) 55 (Suppl. 1):S191.

Kumar et al., "Novel Selective Thiadiazine DYRK1A Inhibitor Lead Scaffold with Human Pancreatic β-cell Proliferation Activity," Eur J Med Chem (2018) 157:1005-16.

Kumar et al., "DYRK1A Inhibitors as Potential Therapeutics for β-Cell Regeneration for Diabetes," J. Med. Chem. (2021) 64(6):2901-22.

Larsson et al., "Safety and Efficacy of Autoantigen-Specific Therapy With 2 Doses of Alum-Formulated Glutamate Decarboxylase in Children with Multiple Islet Autoantibodies and Risk for Type 1 Diabetes: A Randomized Clinical Trial," Pediatr Diabetes. (2018) 19:410-419.

Leung et al., "Soluble RAGE Prevents Type 1 Diabetes Expanding Functional Regulatory T Cells," Diabetes (2022) 71(9):1994-2008.

Liu et al., "Selective DYRK1A Inhibitor for the Treatment of Type 1 Diabetes: Discovery of 6-Azaindole Derivative GNF2133," J. Med. Chem. (2020) 63(6):2958-73.

Näntö-Salonen et al., "Nasal Insulin to Prevent Type 1 Diabetes in Children with HLA Genotypes and Autoantibodies Conferring Increased Risk of Disease: A Double-Blind, Randomised Controlled Trial," The Lancet. (2008) 372:1746-55.

Niddk, "Teplizumab for Prevention of Type 1 Diabetes in Relatives "At-Risk"," ClinicalTrials.gov ID NCT01030861 https://clinicaltrials.gov/study/NCT01030861 (2020).

PCT International Search Report of PCT/US1994/006198, Nov. 2, 1994.

PCT International Search Report of PCT/US2006/027386, Dec. 28, 2007.

PCT International Search Report of PCT/US2007/071275, Aug. 8, 2008.

PCT International Search Report of PCT/US2020/032891, Aug. 26, 2020.

PCT International Search Report of PCT/US2021/037039, Nov. 30, 2021.

PCT International Search Report of PCT/US2022/030780, Sep. 1, 2022.

PCT International Search Report of PCT/US2022/043383, Jan. 4, 2023.

PCT International Search Report of PCT/US2022/076702, Apr. 13, 2023.

PCT International Search Report of PCT/US2023/067357, Nov. 3, 2023.

PCT International Search Report of PCT/US2024/018202, Jun. 26, 2024.

PCT International Search Report of PCT/US2024/022121, Jul. 12, 2024.

PCT International Search Report of PCT/US2024/040020, Nov. 13, 2024.

Sherry et al., "Natural History of Beta-Cell Function in Type 1 Diabetes," Diabetes. (2005) 54 Suppl 2: S32-39.

(56) References Cited

OTHER PUBLICATIONS

Sims et al., "The Deterrence of Rapid Metabolic Decline Within 3 Months After Teplizumab Treatment in Individuals at High Risk for Type 1 Diabetes," Diabetes (2021) 70(12): 2922-31.

Supplementary European Search Report for European Application No. EP 07812153 dated May 19, 2010.

Teplizumab for Prevention of Type 1 Diabetes In Relatives "At-Risk"https://classic.clinicaltrials.gov/ct2/show/study/NCT01030861?term=NCT01030861&draw=2&rank=1 https://classic.clinicaltrials.gov/ct2/history/NCT01030861?V_19=View#StudyPageTop.

* cited by examiner

FIG. 26

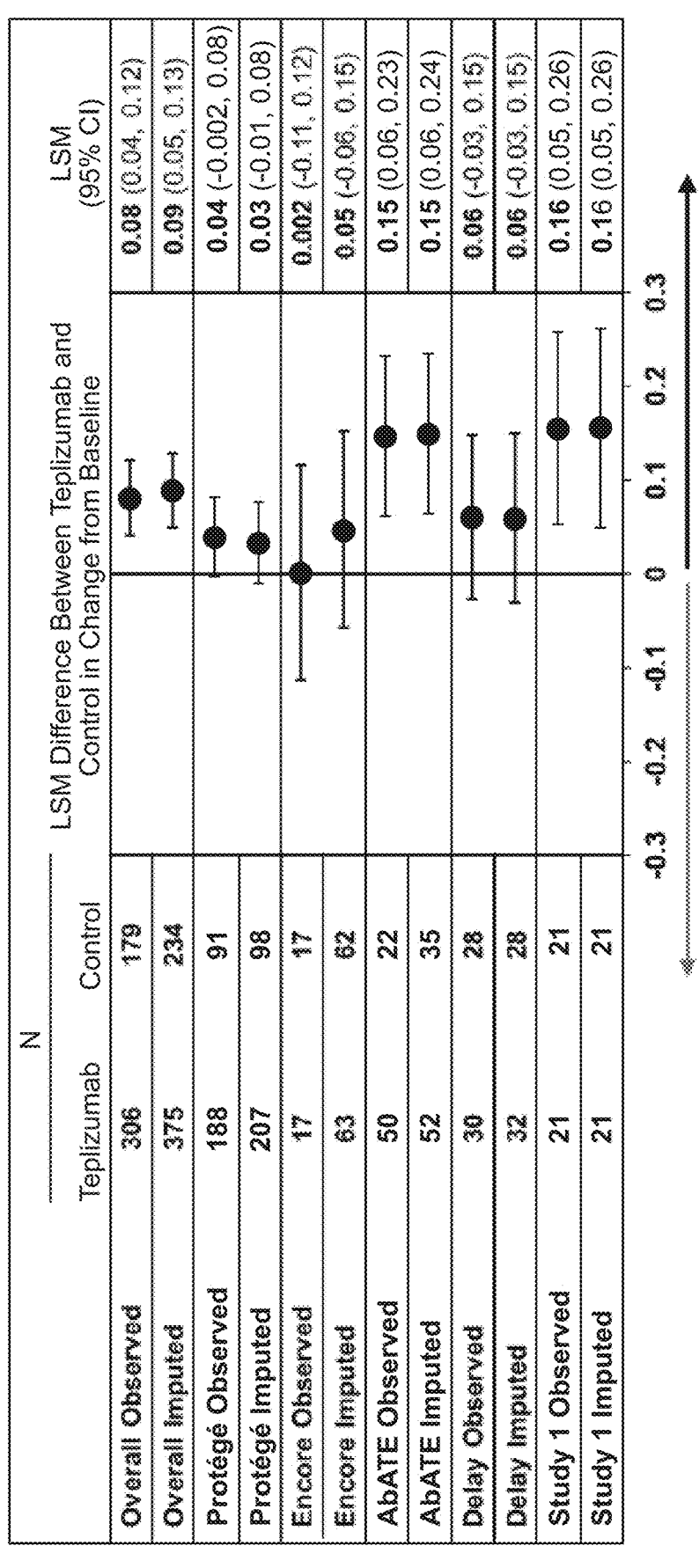

| | N | | LSM Difference Between Teplizumab and Control in Change from Baseline | LSM (95% CI) |
|---|---|---|---|---|
| | Teplizumab | Control | | |
| Overall Observed | 306 | 179 | | 0.08 (0.04, 0.12) |
| Overall Imputed | 375 | 234 | | 0.09 (0.05, 0.13) |
| Protégé Observed | 188 | 91 | | 0.04 (-0.002, 0.08) |
| Protégé Imputed | 207 | 98 | | 0.03 (-0.01, 0.08) |
| Encore Observed | 17 | 17 | | 0.002 (-0.11, 0.12) |
| Encore Imputed | 63 | 62 | | 0.05 (-0.06, 0.15) |
| AbATE Observed | 50 | 22 | | 0.15 (0.06, 0.23) |
| AbATE Imputed | 52 | 35 | | 0.15 (0.06, 0.24) |
| Delay Observed | 30 | 28 | | 0.06 (-0.03, 0.15) |
| Delay Imputed | 32 | 28 | | 0.06 (-0.03, 0.15) |
| Study 1 Observed | 21 | 21 | | 0.16 (0.05, 0.26) |
| Study 1 Imputed | 21 | 21 | | 0.16 (0.05, 0.26) |

-0.3  -0.2  -0.1  0  0.1  0.2  0.3

*Favors Control*     Favors Teplizumab

Note: Analysis conducted and results presented for ln(AUC+1)
Abbreviations: AUC=area under the concentration-time curve, CI=confidence interval, LSM=least squares mean
N=number with 1-year data included in the meta-analysis

FIG. 27

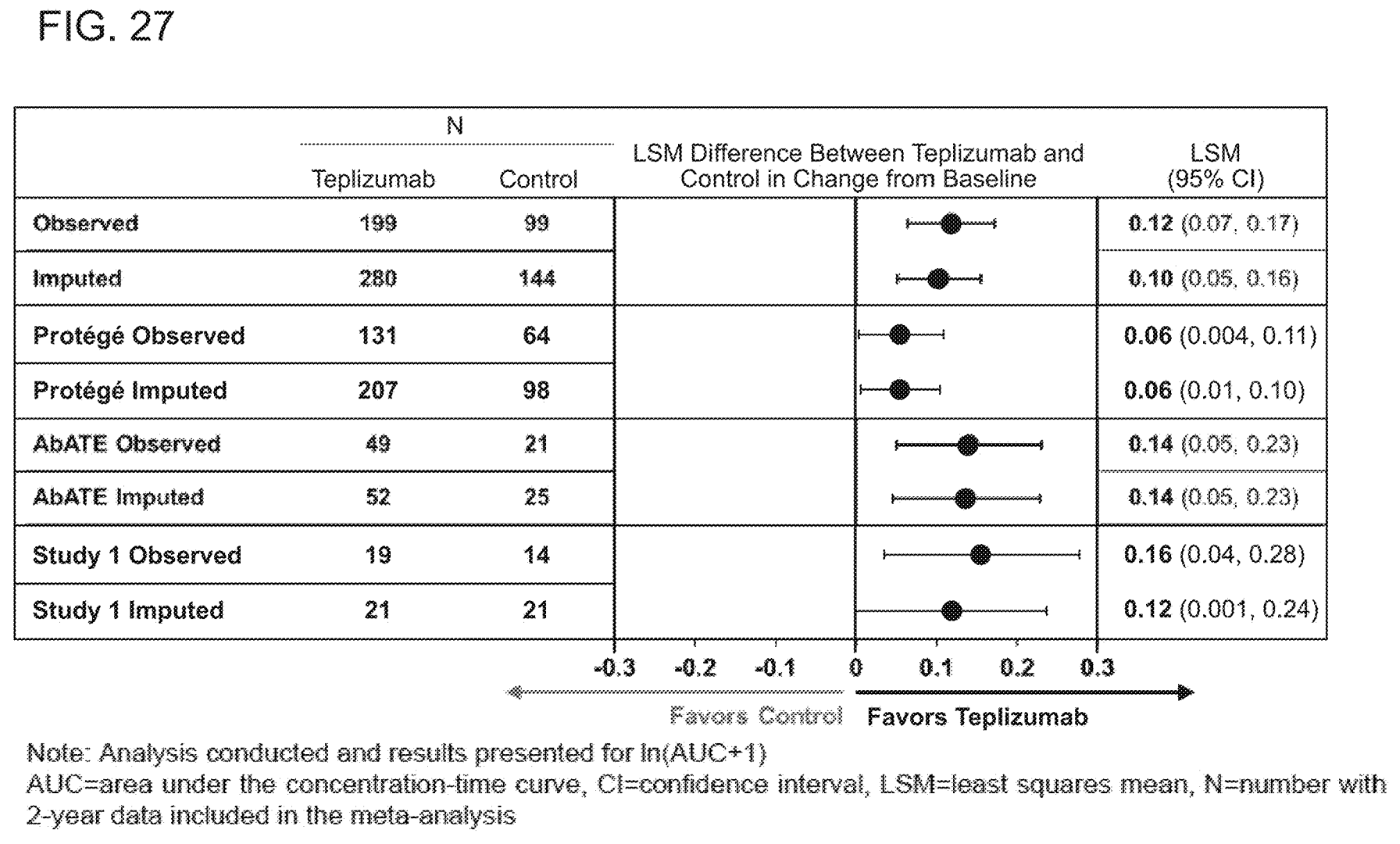

| | N | | LSM Difference Between Teplizumab and Control in Change from Baseline | LSM (95% CI) |
|---|---|---|---|---|
| | Teplizumab | Control | | |
| Observed | 199 | 99 | | 0.12 (0.07, 0.17) |
| Imputed | 280 | 144 | | 0.10 (0.05, 0.16) |
| Protégé Observed | 131 | 64 | | 0.06 (0.004, 0.11) |
| Protégé Imputed | 207 | 98 | | 0.06 (0.01, 0.10) |
| AbATE Observed | 49 | 21 | | 0.14 (0.05, 0.23) |
| AbATE Imputed | 52 | 25 | | 0.14 (0.05, 0.23) |
| Study 1 Observed | 19 | 14 | | 0.16 (0.04, 0.28) |
| Study 1 Imputed | 21 | 21 | | 0.12 (0.001, 0.24) |

-0.3   -0.2   -0.1   0   0.1   0.2   0.3

Favors Control      Favors Teplizumab

Note: Analysis conducted and results presented for ln(AUC+1)
AUC=area under the concentration-time curve, CI=confidence interval, LSM=least squares mean, N=number with 2-year data included in the meta-analysis

AUC 2-H-OGTT

Number of Patients with
all 3 tests available

| | 0 | 3 | 6 | 12 | 18 | 24 | 30 | 36 | 42 |
|---|---|---|---|---|---|---|---|---|---|
| Teplizumab | 20 | 18 | 20 | 18 | 15 | 9 | 8 | 5 | 5 |
| Placebo | 23 | 22 | 15 | 11 | 9 | 8 | 7 | 5 | | a. Protégé b. Encore c. Study 1 d. AbATE e. Delay

FIG. 30B

Cycle 1: Typical 40 and 90 kg male subject

FIG. 30A

Cycle 1: Typical 60 kg male subject

SEQUENCE LISTING

```
<160> NUMBER OF SEQ ID NOS: 2

<210> SEQ ID NO 1
<211> LENGTH: 213
<212> TYPE: PRT
<213> ORGANISM: Unknown
<220> FEATURE:
<223> OTHER INFORMATION: Synthetic

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Val Ser Tyr Met
                20                  25                  30

Asn Trp Tyr Gln Gln Thr Pro Gly Lys Ala Pro Lys Arg Trp Ile Tyr
            35                  40                  45

Asp Thr Ser Lys Leu Ala Ser Gly Val Pro Ser Arg Phe Ser Gly Ser
    50                  55                  60

Gly Ser Gly Thr Asp Tyr Thr Phe Thr Ile Ser Ser Leu Gln Pro Glu
65                  70                  75                  80

Asp Ile Ala Thr Tyr Tyr Cys Gln Gln Trp Ser Ser Asn Pro Phe Thr
                85                  90                  95

Phe Gly Gln Gly Thr Lys Leu Gln Ile Thr Arg Thr Val Ala Ala Pro
            100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
    210

<210> SEQ ID NO 2
<211> LENGTH: 449
<212> TYPE: PRT
<213> ORGANISM: Unknown
<220> FEATURE:
<223> OTHER INFORMATION: Synthetic

<400> SEQUENCE: 2
```

-continued

```
Gln Val Gln Leu Val Gln Ser Gly Gly Gly Val Val Gln Pro Gly Arg
1               5                   10                  15

Ser Leu Arg Leu Ser Cys Lys Ala Ser Gly Tyr Thr Phe Thr Arg Tyr
            20                  25                  30

Thr Met His Trp Val Arg Gln Ala Pro Gly Lys Gly Leu Glu Trp Ile
        35                  40                  45

Gly Tyr Ile Asn Pro Ser Arg Gly Tyr Thr Asn Tyr Asn Gln Lys Val
    50                  55                  60

Lys Asp Arg Phe Thr Ile Ser Arg Asp Asn Ser Lys Asn Thr Ala Phe
65                  70                  75                  80

Leu Gln Met Asp Ser Leu Arg Pro Glu Asp Thr Gly Val Tyr Phe Cys
                85                  90                  95

Ala Arg Tyr Tyr Asp Asp His Tyr Cys Leu Asp Tyr Trp Gly Gln Gly
            100                 105                 110

Thr Pro Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415
```

-continued

```
Ser Arg Trp Gln Gln Gly Asn Val Phe Ser Cys Ser Val Met His Glu
        420                 425                 430

Ala Leu His Asn His Tyr Thr Gln Lys Ser Leu Ser Leu Ser Pro Gly
        435                 440                 445

Lys
```

METHODS FOR TREATING TYPE 1 DIABETES

RELATED APPLICATIONS

This application claims priority to and the benefit of U.S. Provisional Application No. 63/192,402, filed May 24, 2021, the entire disclosure of which is incorporated herein by reference.

SEQUENCE LISTING

This specification includes a sequence listing submitted herewith, which includes the file entitled 178833-011101_ST25.txt having the following size: 6,058 bytes which was created May 23, 2022, the contents of which are incorporated by reference herein.

FIELD

The present disclosure relates in general to methods and dosage regimen for treating type 1 diabetes (T1D) in subjects in need thereof.

BACKGROUND

Type 1 diabetes (T1D) is caused by the autoimmune destruction of insulin producing beta cells in the islets of Langerhans leading to dependence on exogeneous insulin injections for survival. Approximately 1.6 million Americans have Type 1 diabetes, and after asthma, it remains one of the most common diseases of childhood. Despite improvements in care, most affected individuals with T1D are not able to consistently achieve desired glycemic targets. For individuals with type 1 diabetes, there are persisting concerns for increased risk of both morbidity and mortality. Two recent studies noted loss of 17.7 life-years for children diagnosed before age 10, and 11 and 13 life-years lost for adult-diagnosed Scottish men and women respectively.

Thus, a need exists for improved T1D treatment methods and compositions.

SUMMARY

Some aspects relate to a method of treating clinical type 1 diabetes (T1D), comprising administering to a subject in need thereof a 12-day course of teplizumab at a total dose of more than about 9000 μg/m². Some aspects relate to teplizumab for use in a method of treating clinical type 1 diabetes (T1D), comprising administering to a subject in need thereof a 12-day course of the teplizumab at a total dose of more than about 9000 μg/m².

In some embodiments, the total dose is between about 9000 and about 9500 μg/m². In some embodiments, the total dose is between about 9000 and about 14000 μg/m².

In some embodiments, a method of treating type 1 diabetes (T1D) is provided comprising administering to a subject in need thereof a 12-day course of teplizumab at a total dose of from about 9000 to about 9500 μg/m². In some embodiments, a method of treating type 1 diabetes (T1D) is provided comprising administering to a subject in need thereof a 12-day course of teplizumab at a total dose of from about 9000 to about 14000 μg/m².

In some embodiments, the 12-day course comprises a first dose of 106 μg/m² teplizumab on day 1, a second dose of 425

μg/m² teplizumab on day 2, and one dose of 850 μg/m² on each of days 3-12, and wherein the total dose is approximately 9031 μg/m².

In some embodiments, the 12-day course comprises a first dose of 211 μg/m² teplizumab on day 1, a second dose of 423 μg/m² teplizumab on day 2, and one dose of 840 μg/m² on each of days 3-12, and wherein the total dose is approximately 9034 μg/m².

In some embodiments, the method can include administering a first and a second 12-day courses of teplizumab. In some embodiments, the first and the second 12-day courses are administered at about 1-6 months, about 2-5 months or about 3 months interval.

In some embodiments, the method can include administering to the subject in need thereof a third or more 12-day course of teplizumab, each course at a total dose of more than about 9000 μg/m².

In some embodiments, the third or more 12-day course of teplizumab comprises a first dose of 106 μg/m² teplizumab on day 1, a second dose of 425 μg/m² teplizumab on day 2, and one dose of 850 μg/m² on each of days 3-12, and wherein the total dose of each course is approximately 9031 μg/m².

In some embodiments, the third or more 12-day course of teplizumab comprises a first dose of 211 μg/m² teplizumab on day 1, a second dose of 423 μg/m² teplizumab on day 2, and one dose of 840 μg/m² on each of days 3-12, and wherein the total dose of each course is approximately 9034 μg/m².

In some embodiments, the third or more 12-day course of teplizumab is administered at about a 12 month to about a 24-month interval.

In some embodiments, the method can further include determining, after the administration of each 12-day course, a baseline of a level of TIGIT+KLRG1+CD8+ cells with respect to all CD3+ T cells, monitoring the level of the TIGIT+KLRG1+CD8+CD3+ T-cells and administering an additional 12-day course of teplizumab when the level of the TIGIT+KLRG1+CD8+CD3+ T-cells returns to the baseline level. In some embodiments, the determining of TIGIT+KLRG1+CD8+CD3+ T-cells is by flow cytometry. In some embodiments, the monitoring of TIGIT+KLRG1+CD8+CD3+ T-cells is by flow cytometry. In some embodiments, the determining of TIGIT+KLRG1+CD8+CD3+ T-cells is about 1-6 months, about 2-5 months, or about 3 months after the administration of each 12-day course. In some embodiments, if the subject has more than about 10% TIGIT+KLRG1+CD8+ T-cells in all CD3+ T cells, subsequent monitoring is annual. In some embodiments, if the subject has less than about 10% TIGIT+KLRG1+CD8+ T-cells in all CD8+ T cells, subsequent monitoring is every about 3-6 months.

In some embodiments, the subject in need thereof has been diagnosed with T1D within 6 weeks prior to the administrating step.

In some embodiments, the administrating step results in reduction by at least 10% of insulin use, HbA1c levels, hypoglycemic episodes, or combinations thereof as compared to pre-treatment levels.

In some embodiments, each dose is administered parenterally.

In some embodiments, each dose is administered by intravenous infusion.

In some embodiments, the subject in need thereof is about 8 to 17 years old.

In some embodiments, the subject in need thereof have a peak C-peptide level of ≥0.2 pmol/mL during a mixed meal tolerance test (MMTT).

In some embodiments, the subject receiving teplizumab has a higher mean C-peptide value compared with a control receiving placebo.

In some embodiments, the method further includes assessing the area under the time-concentration curve (AUC) of C-peptide following a mixed meal tolerance test (MMTT), at 78 weeks.

In some embodiments, the subject in need thereof has at least 20% of beta-cell function prior the administration of the first dose.

In some embodiments, the reduction of insulin use, HbA1c levels, hypoglycemic episodes, or combinations thereof is over a period of 12 months or more.

4

Model-based Simulations for Typical Male Patients with WT=45 kg, Age=13 years, BSA=1.33 m², and no Detected ADAs.

Figure 11:
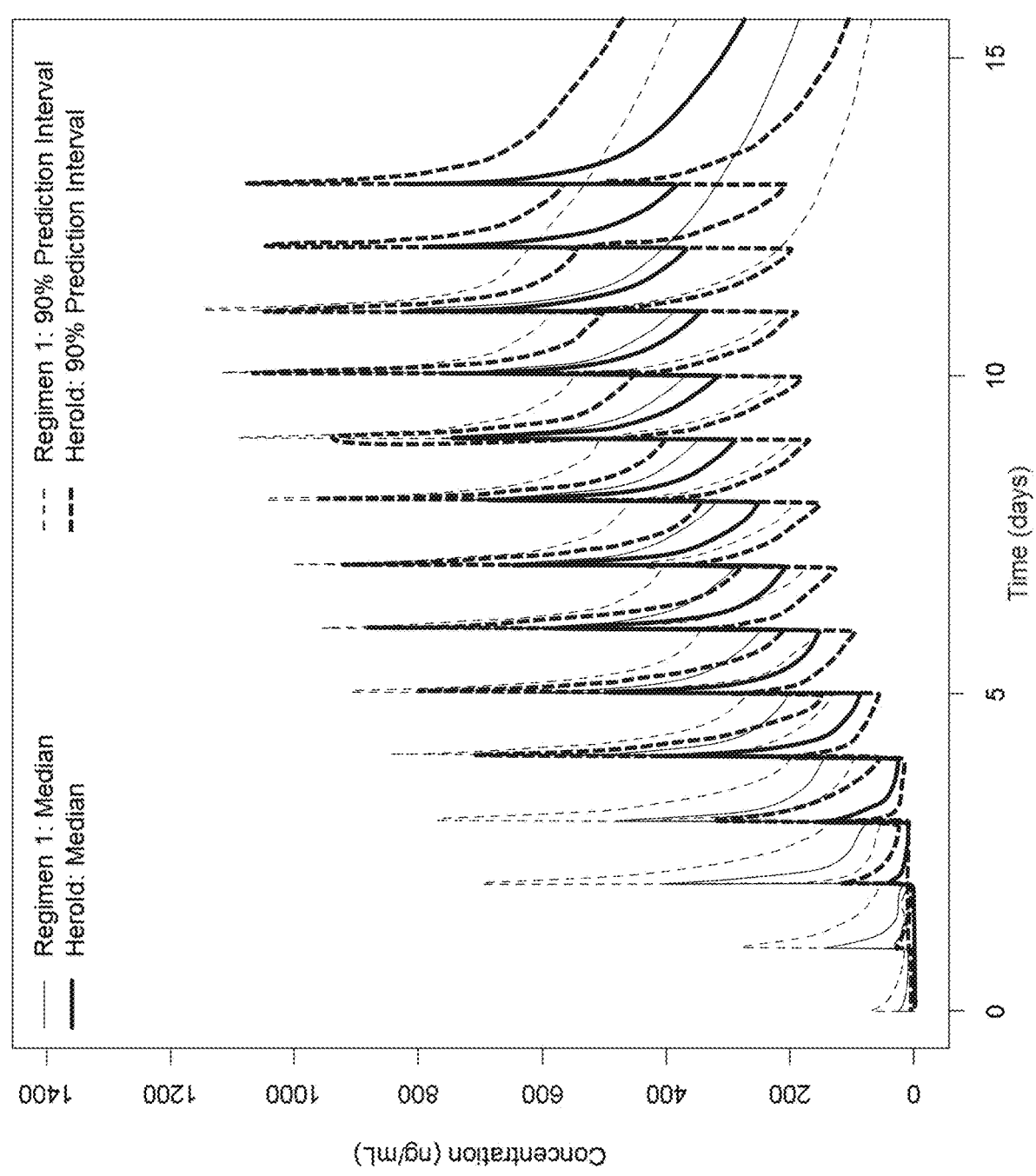

FIG. 11 is a graph showing Comparison of Concentrations versus Time Profiles for Herold Dosing Regimen and Dosing Regimen 1: Model-based Simulations for Typical Male Patients with WT=45 kg, Age=13 years, BSA=1.33 m², and no Detected ADAs.

Figure 12:
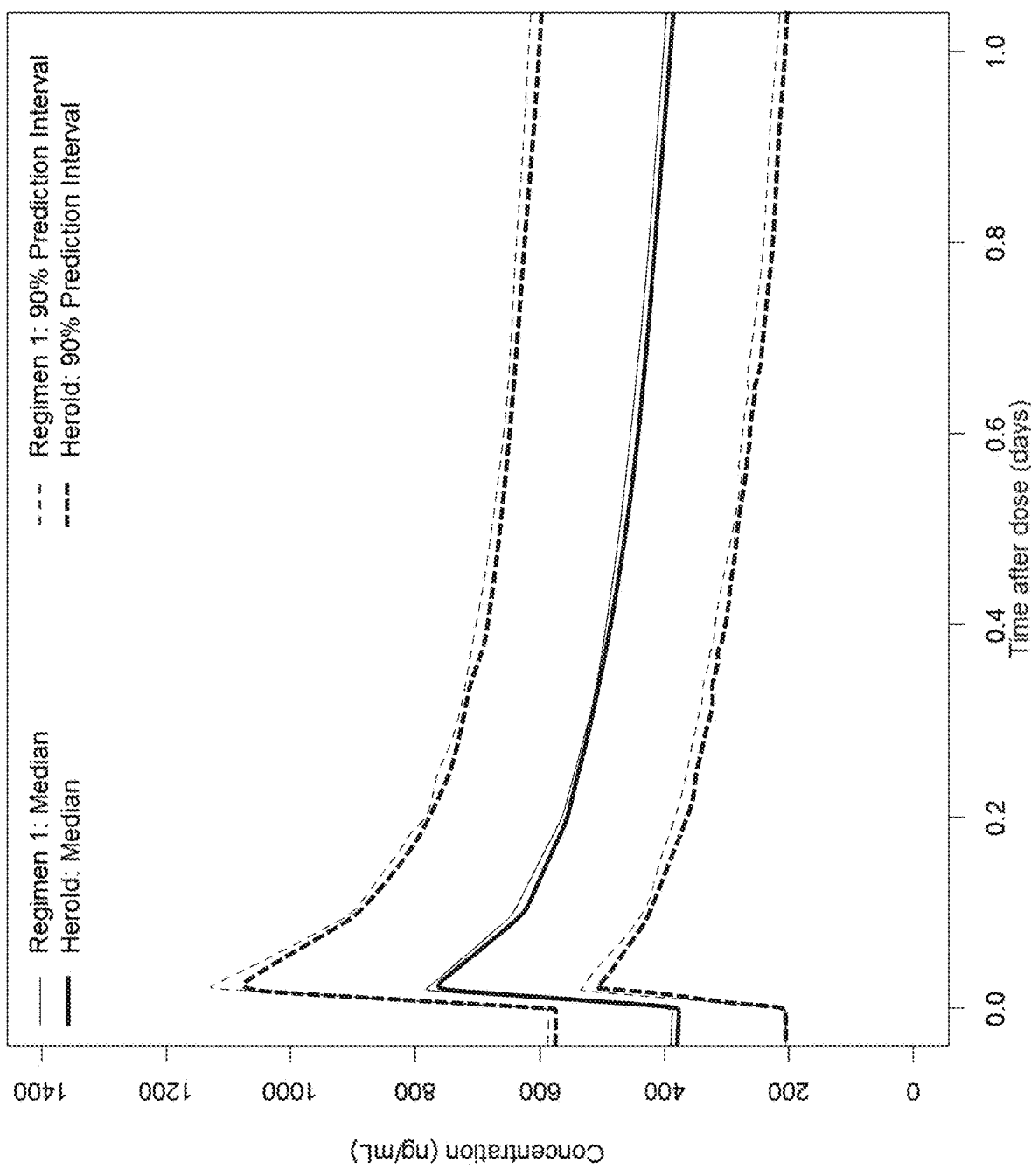
Figures 13A, 13B, 13C, 13D, 13E, 13F:
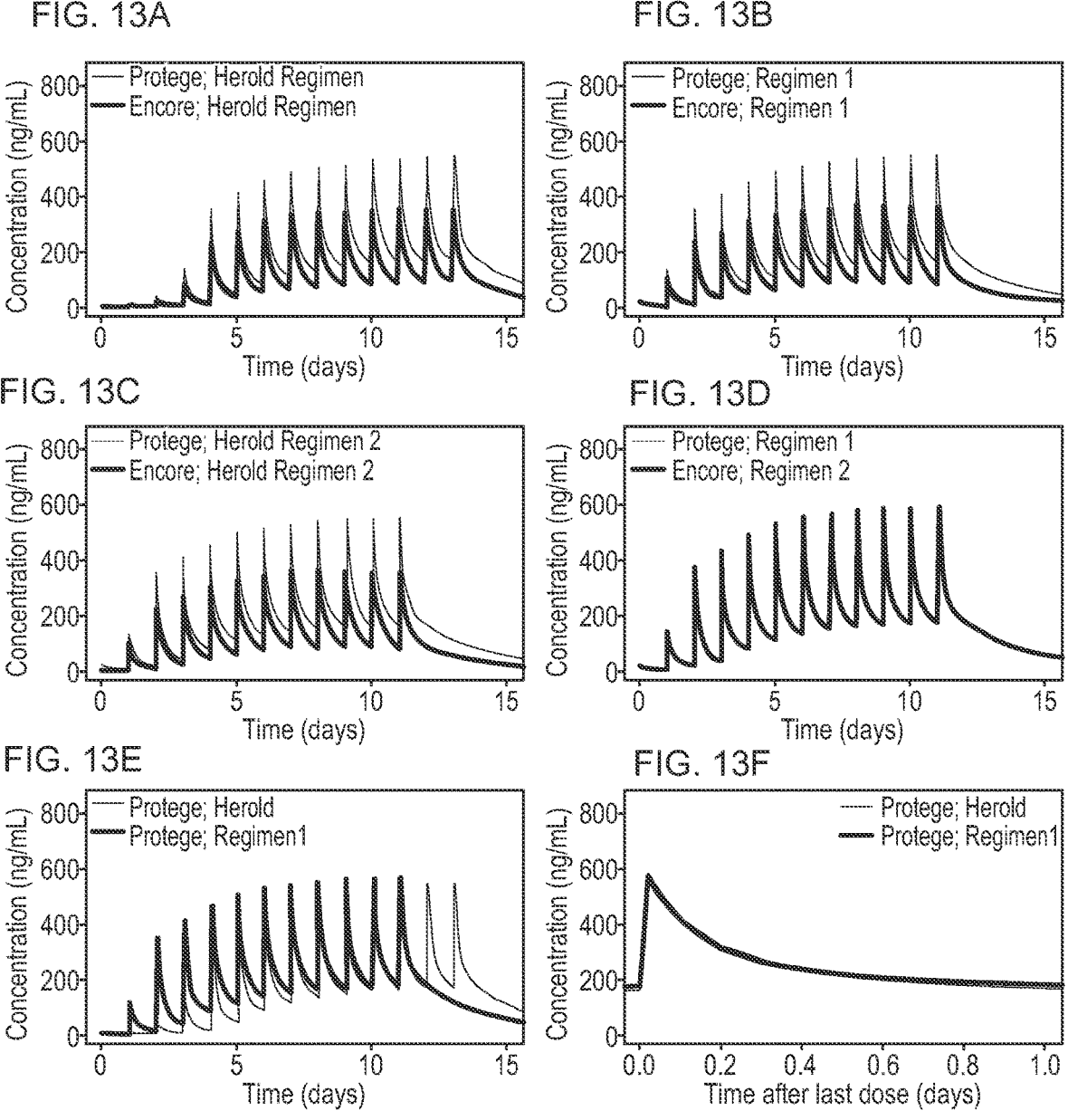

FIG. 12 is a graph showing Comparison of Concentrations versus Time Profiles on the last dosing day for Herold Dosing Regimen and Dosing Regimen 1: Model-based Simulations for Typical Male Patients with WT=45 kg, Age=13 years, BSA=1.33 m², and no Detected ADAs.

FIGS. 13A-13F are graphs showing Simulated Concentrations versus Time Profiles For Three Dosing Regimens: Population Predictions for a Typical Male Patient with WT=45 kg, Age=13 years, BSA=1.33 m², and High Level of Detected ADAs.

Figure 14:
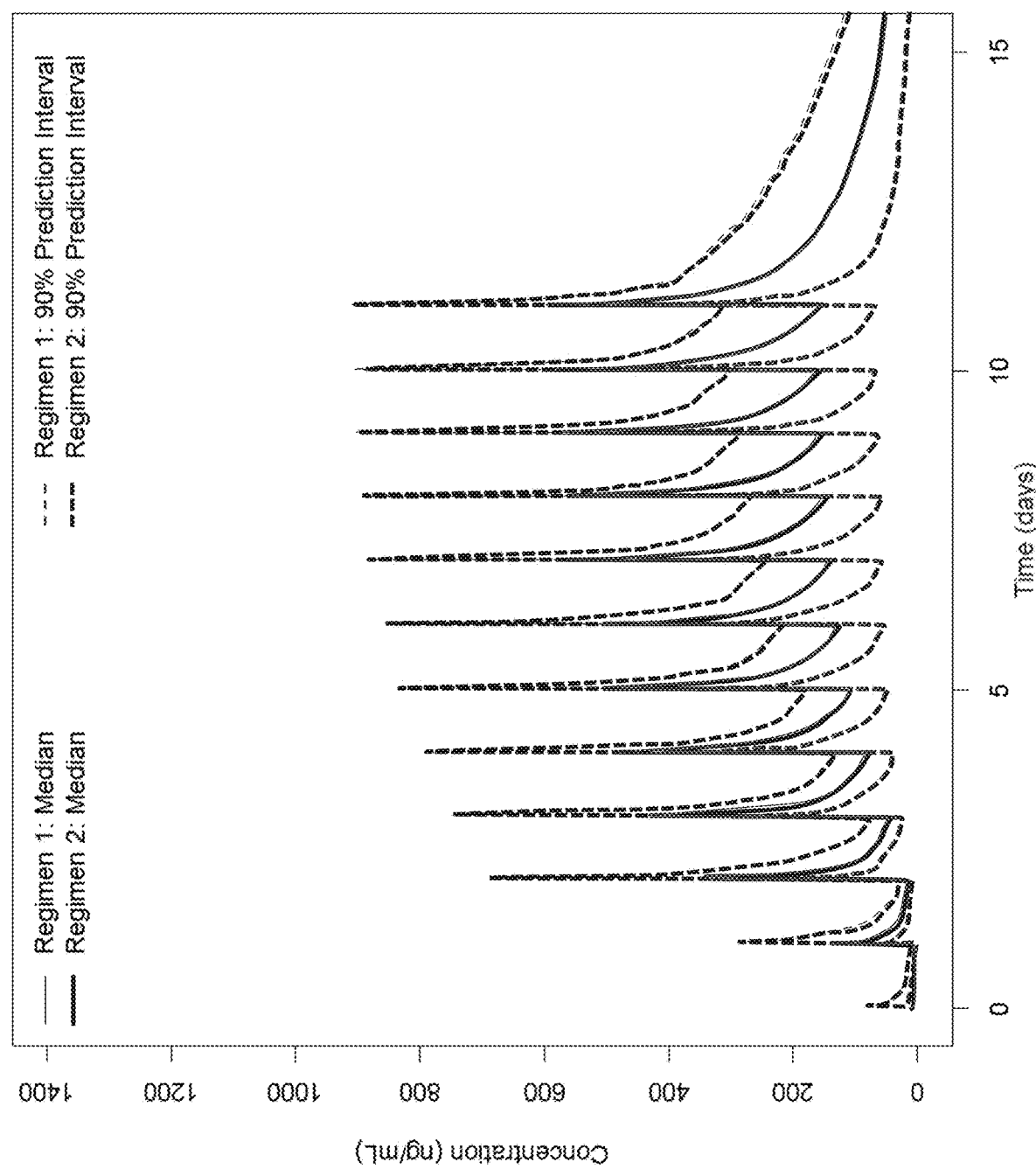

FIG. 14 is a graph showing Comparison of Concentrations versus Time Profiles for Dosing Regimens 1 and 2: Model-based Simulations for Typical Male Patients with WT=45 kg, Age=13 years, BSA=1.33 m², and High Level of Detected ADAs.

Figure 15:
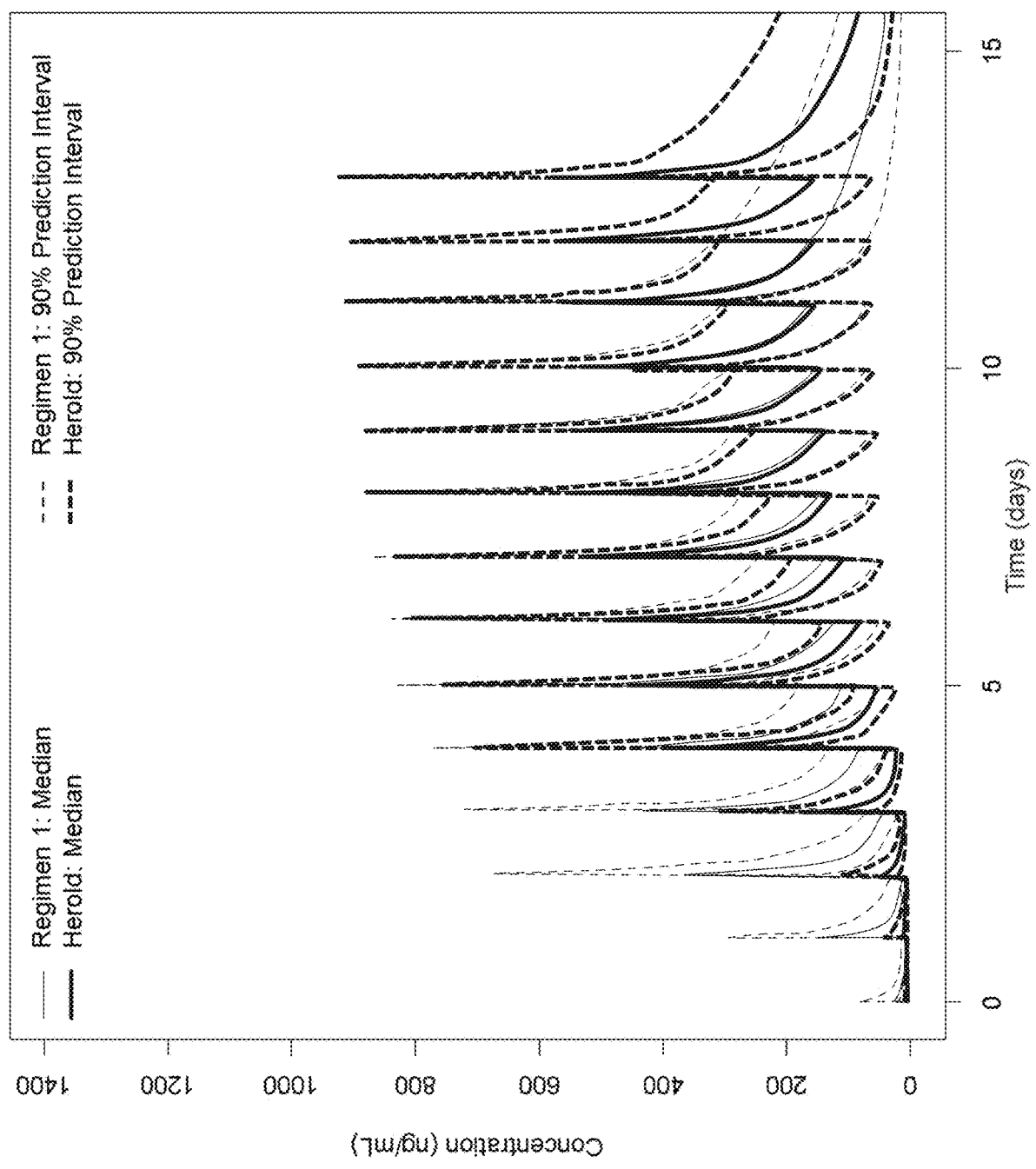

FIG. 15 is a graph showing Comparison of Concentrations versus Time Profiles for Herold Dosing Regimen and Dosing Regimen 1: Model-based Simulations for Typical Male Patients with WT=45 kg, Age=13 years, BSA=1.33 m², and High Level of Detected ADAs.

Figure 16:
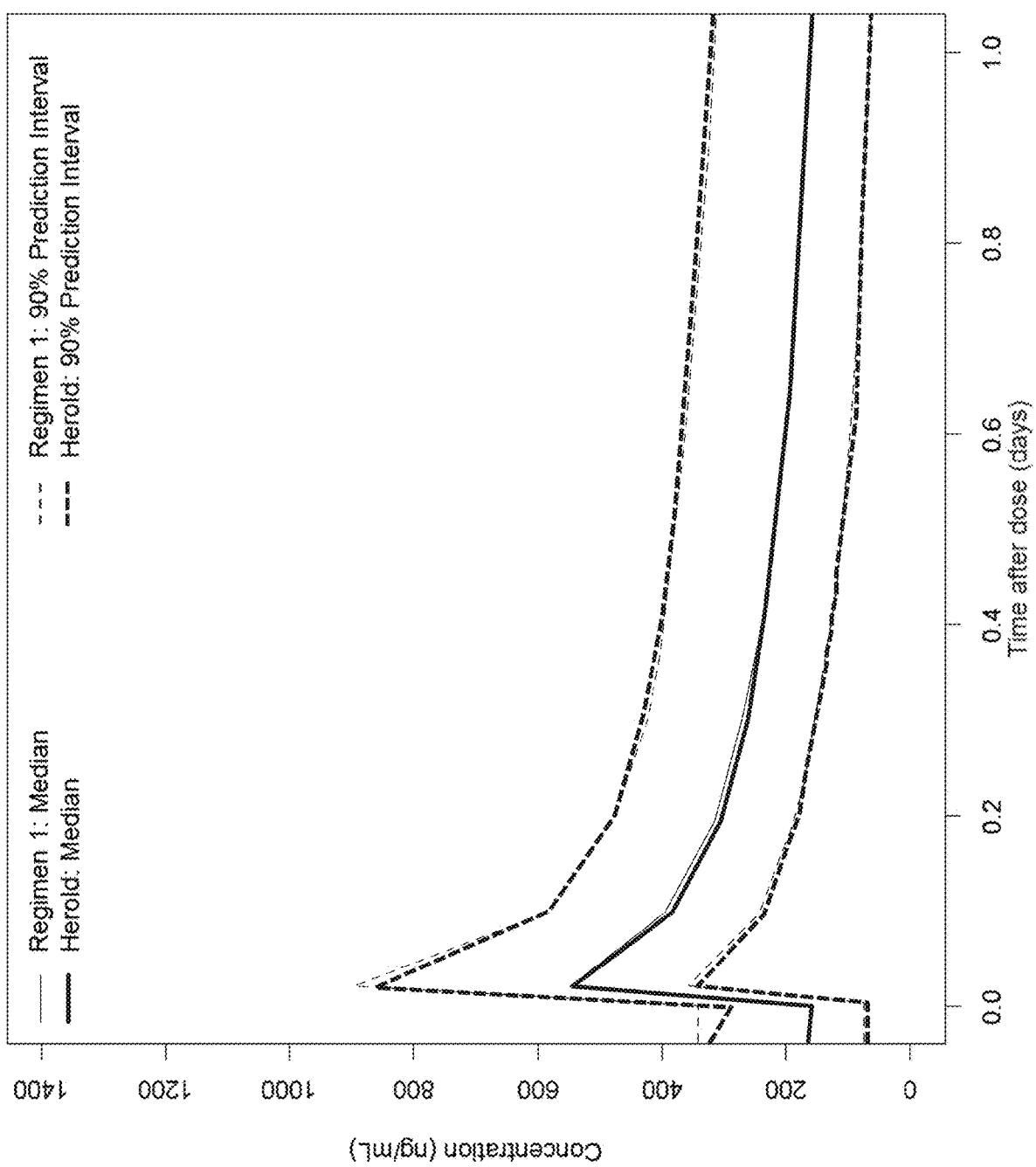

FIG. 16 is a graph showing Comparison of Concentrations versus Time Profiles on the last dosing day for Herold Dosing Regimen and Dosing Regimen 1: Model-based Simulations for Typical Male Patients with WT=45 kg, Age=13 years, BSA=1.33 m², and High Level of Detected ADAs.

Figure 17:
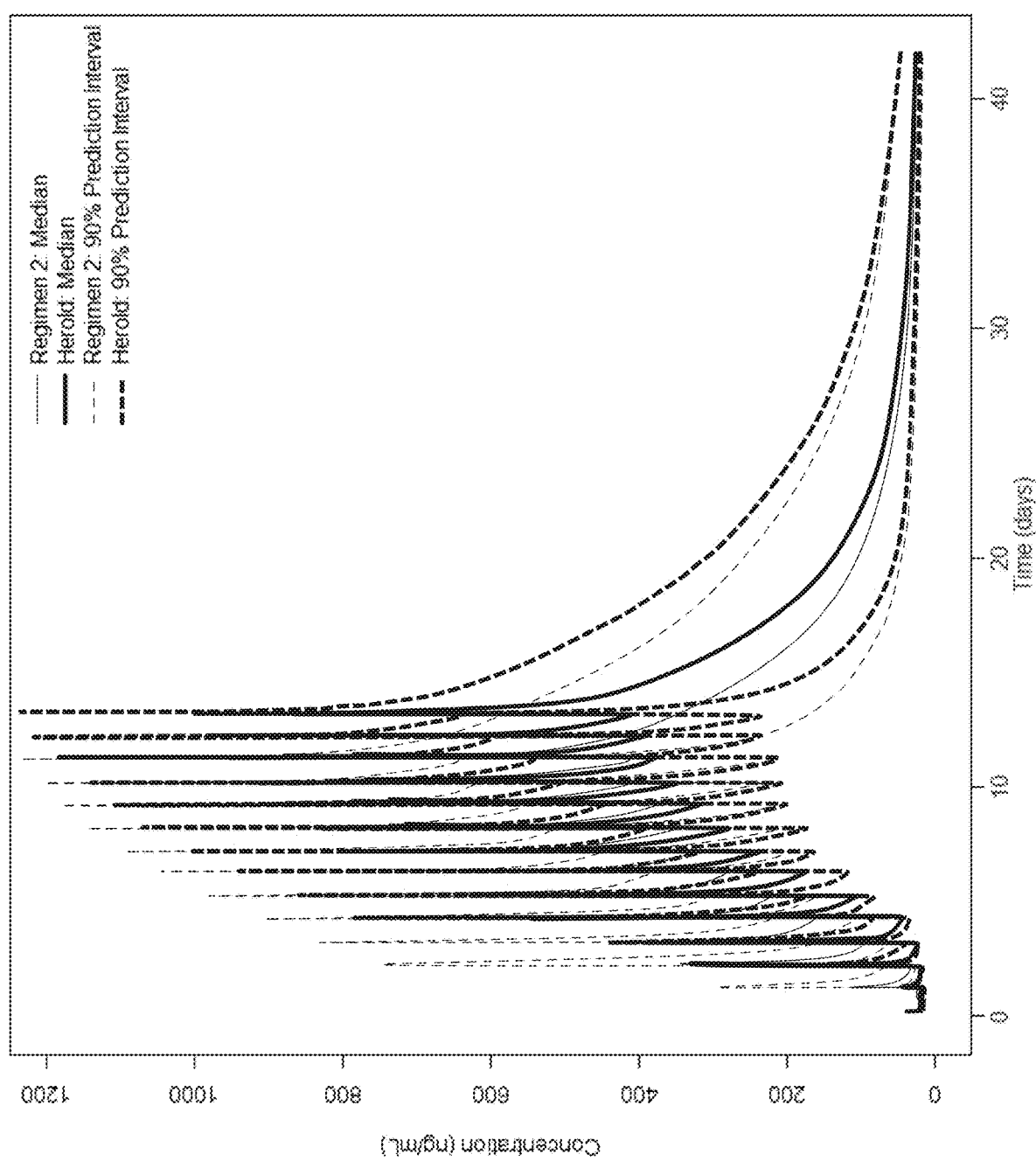

FIG. 17 is a graph showing Comparison of Concentrations versus Time Profiles for Herold Regimen and Dosing Regimen 2: Model-based Simulations for Male Patients with WT=60 kg, Age=18 years, BSA=1.67 m², and no Detected ADAs (42 days).

Figure 18:
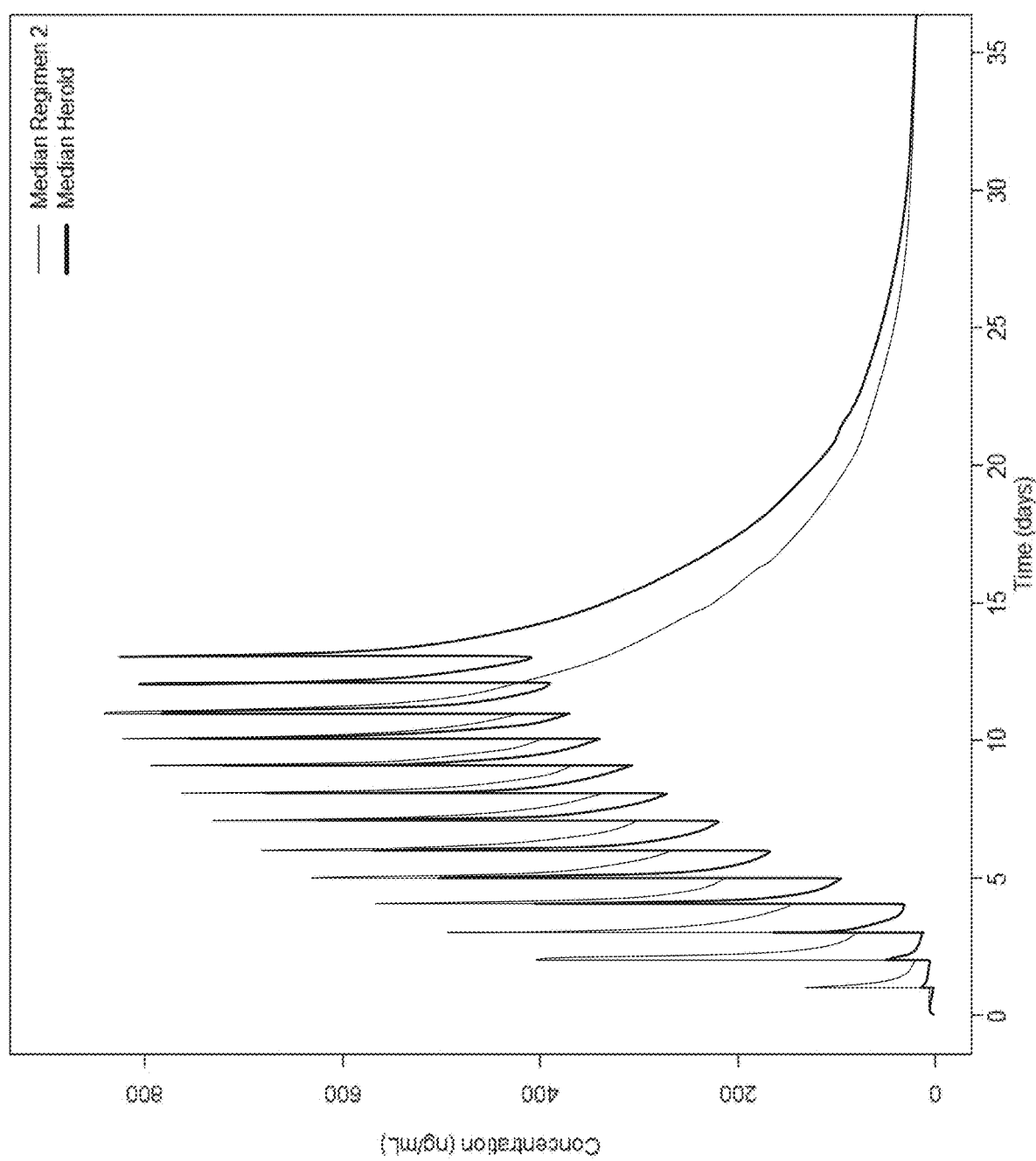

FIG. 18 is a graph showing Comparison of Median Concentrations versus Time Profiles for Herold Regimen and Dosing Regimen 2: Model-based Simulations for Male Patients with WT=60 kg, Age=18 years, BSA=1.67 m², and no Detected ADAs (35 days).

Figure 19:
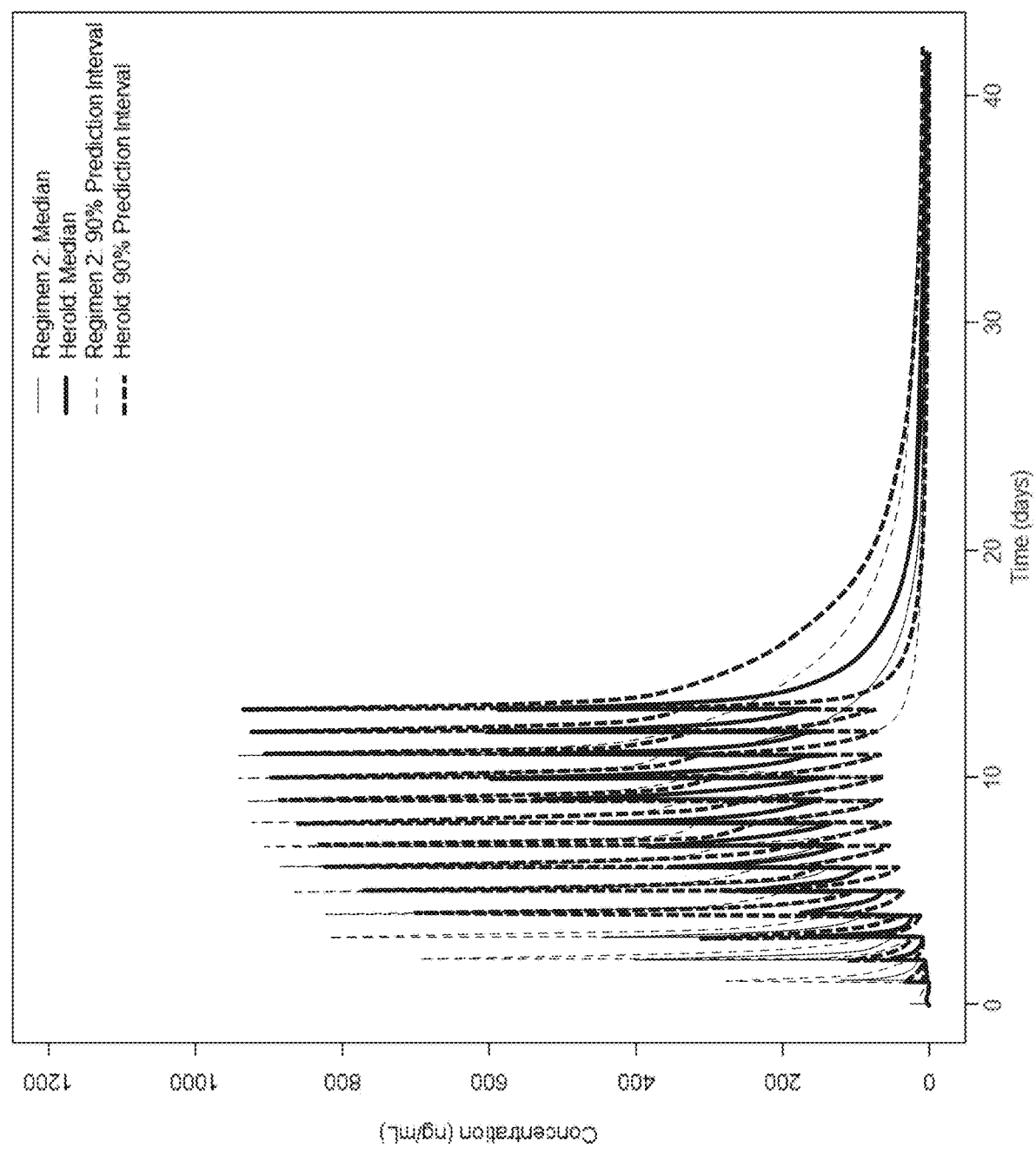

FIG. 19 is a graph showing Comparison of Concentrations versus Time Profiles for Herold Regimen and Dosing Regimen 2: Model-based Simulations for Male Patients with WT=60 kg, Age=18 years, BSA=1.67 m², and High Level of Detected ADAs (42 days).

Figure 20:
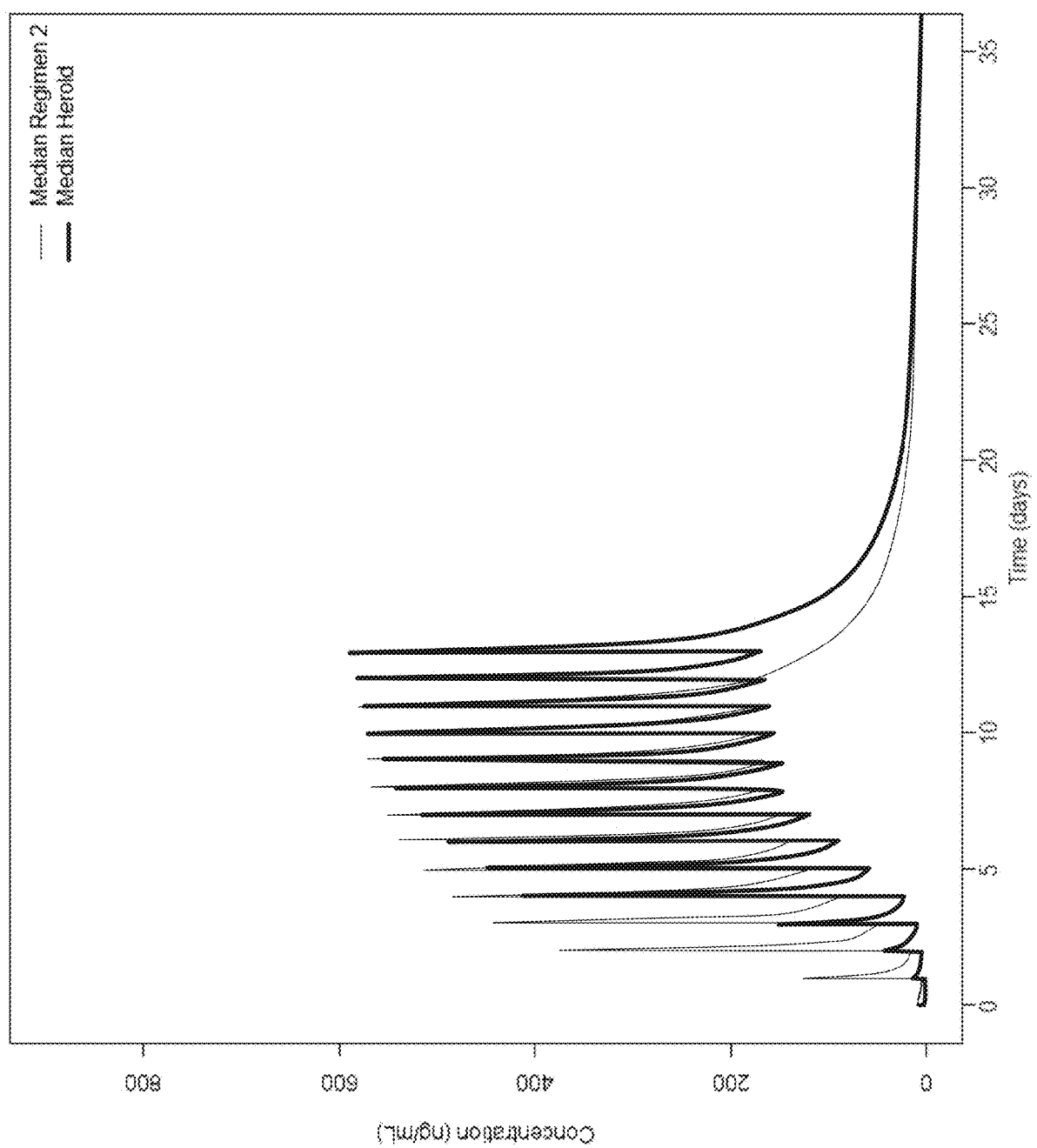

FIG. 20 is a graph showing Comparison of Median Concentrations versus Time Profiles for Herold Regimen and Dosing Regimen 2: Model-based Simulations for Male Patients with WT=60 kg, Age=18 years, BSA=1.67 m², and High Level of Detected ADAs (35 days).

Figure 21:
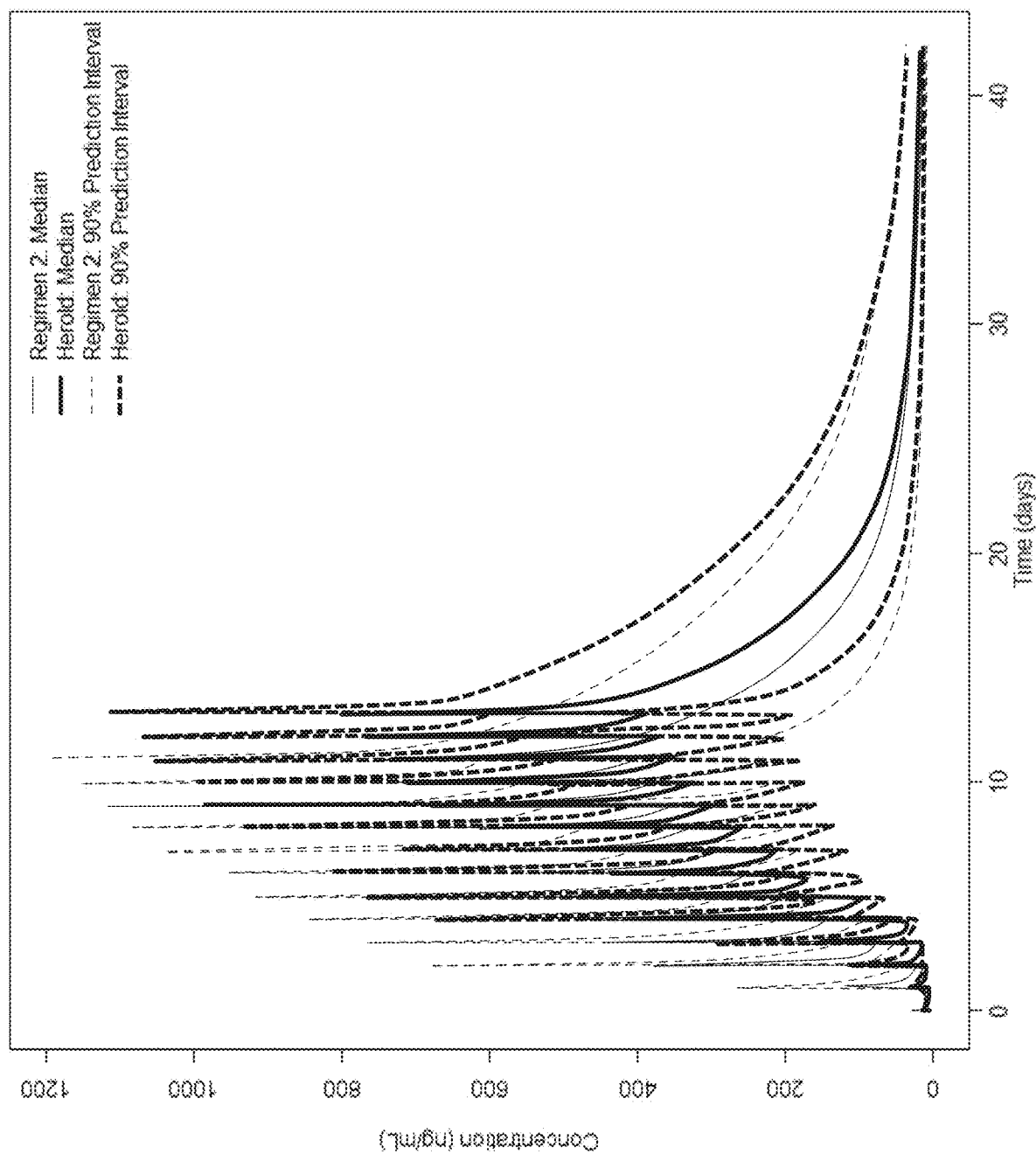

FIG. 21 is a graph showing Comparison of Concentrations versus Time Profiles for Herold Regimen and Dosing Regimen 2: Model-based Simulations for Male Patients with WT=45 kg, Age=13 years, BSA=1.33 m², and no Detected ADAs (42 days).

Figure 22:
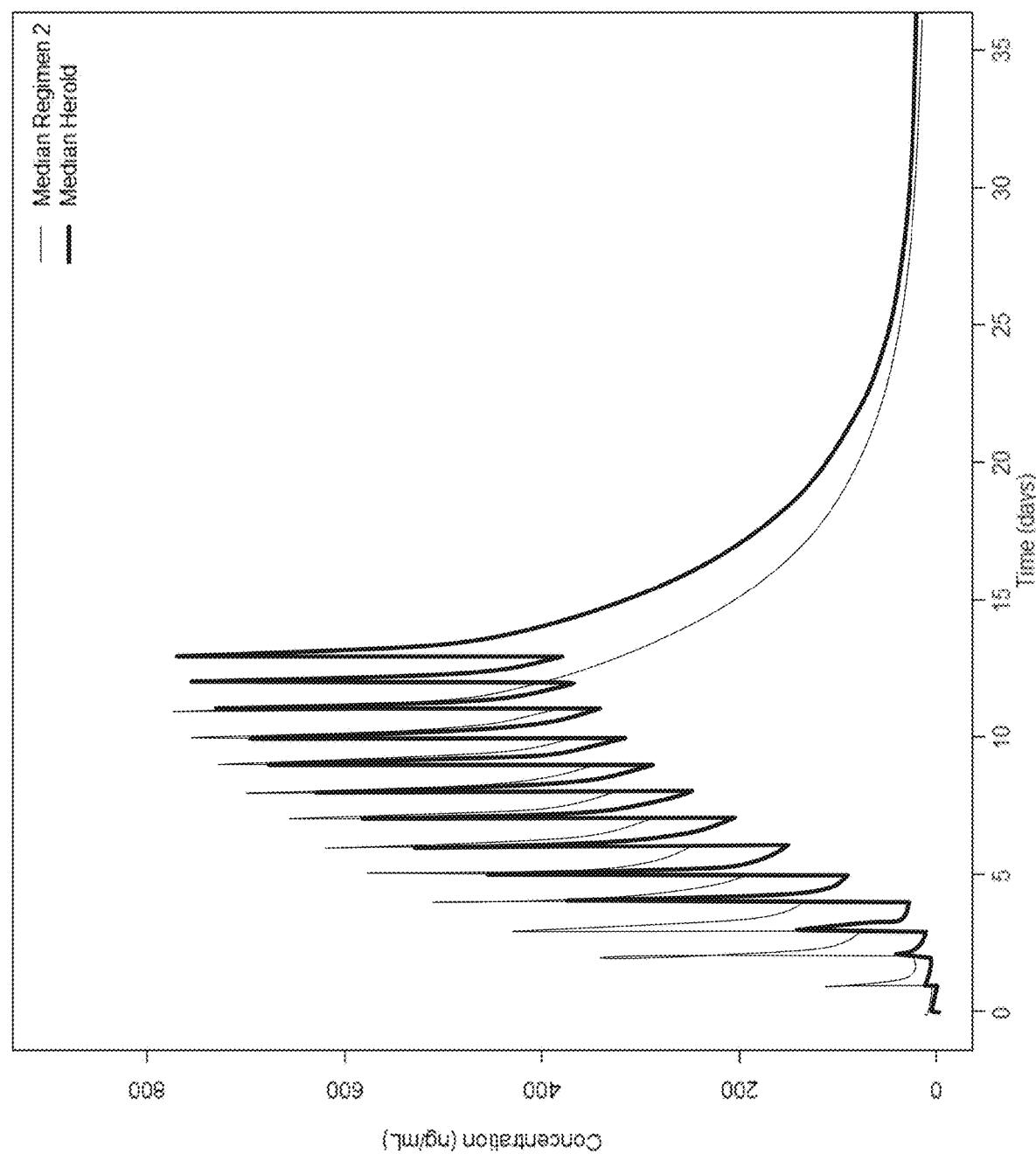

FIG. 22 is a graph showing Comparison of Median Concentrations versus Time Profiles for Herold Regimen and Dosing Regimen 2: Model-based Simulations for Male Patients with WT=45 kg, Age=13 years, BSA=1.33 m², and no Detected ADAs (35 days).

Figure 23:
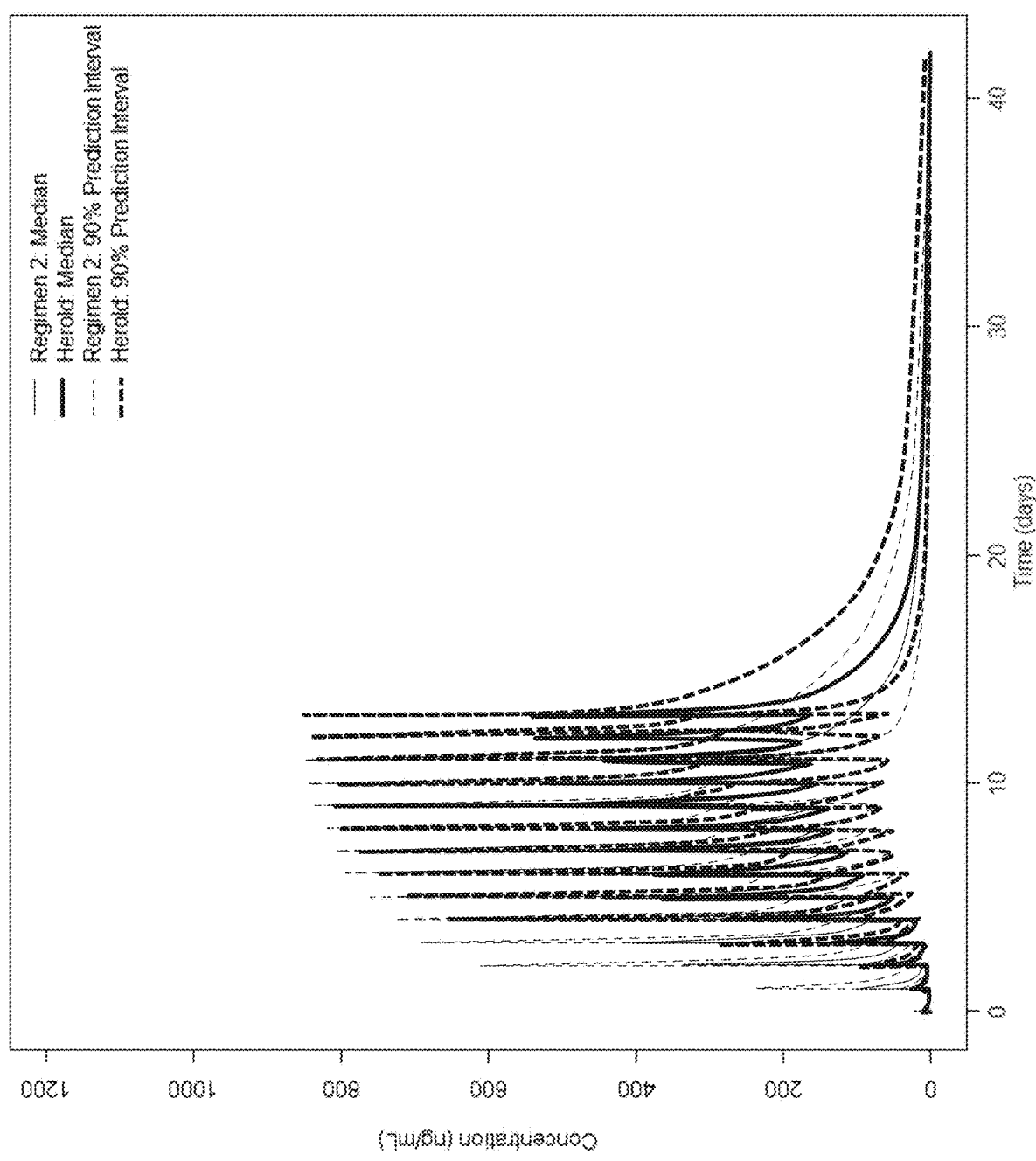

FIG. 23 is a graph showing Comparison of Concentrations versus Time Profiles for Herold Regimen and Dosing Regimen 2: Model-based Simulations for Male Patients with WT=45 kg, Age=13 years, BSA=1.33 m², and High Level of Detected ADAs (42 days).

Figure 24:
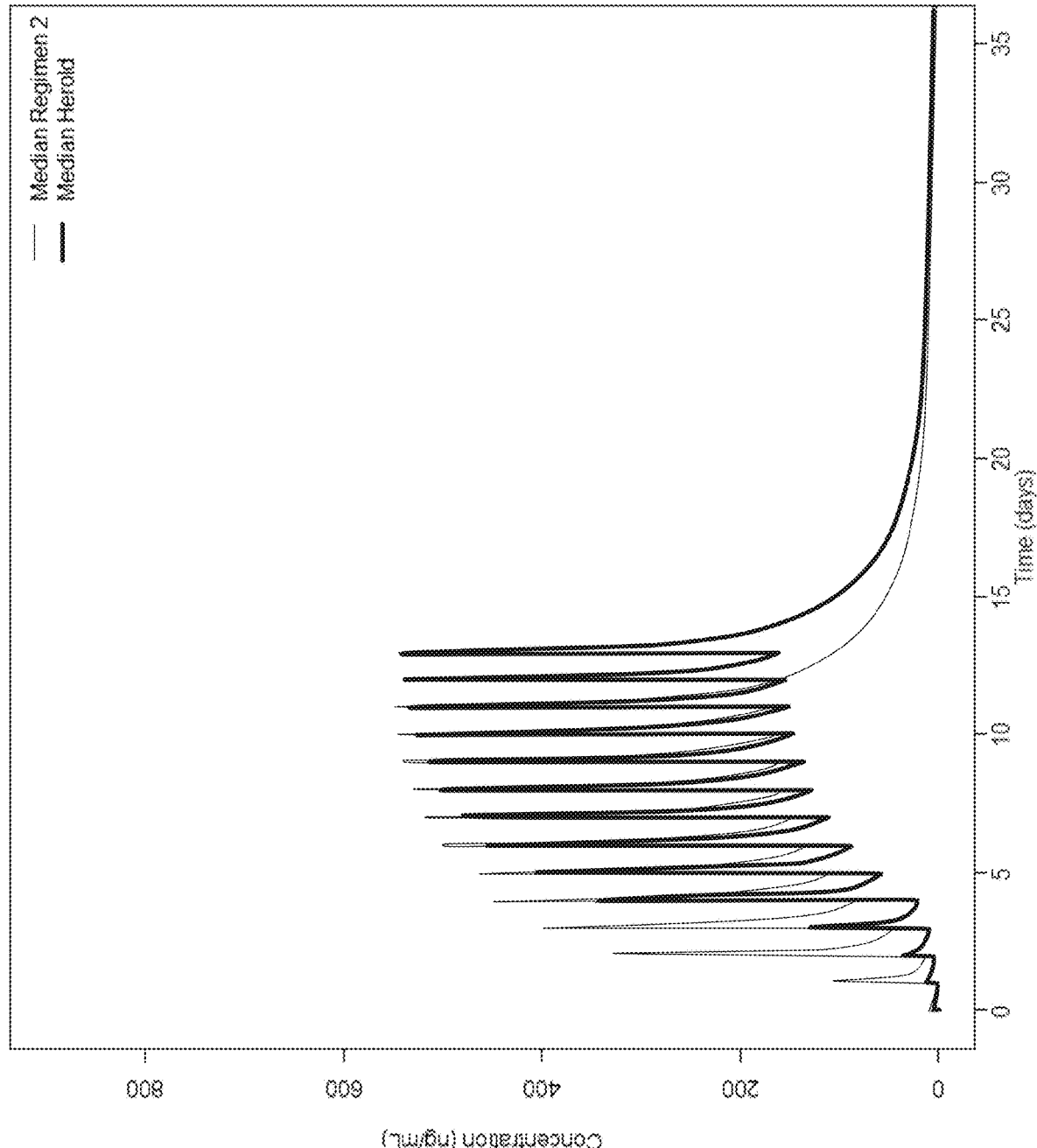

FIG. 24 is a graph showing Comparison of Median Concentrations versus Time Profiles for Herold Regimen and Dosing Regimen 2: Model-based Simulations for Male Patients with WT=45 kg, Age=13 years, BSA=1.33 m², and High Level of Detected ADAs (35 days).

Figure 25:
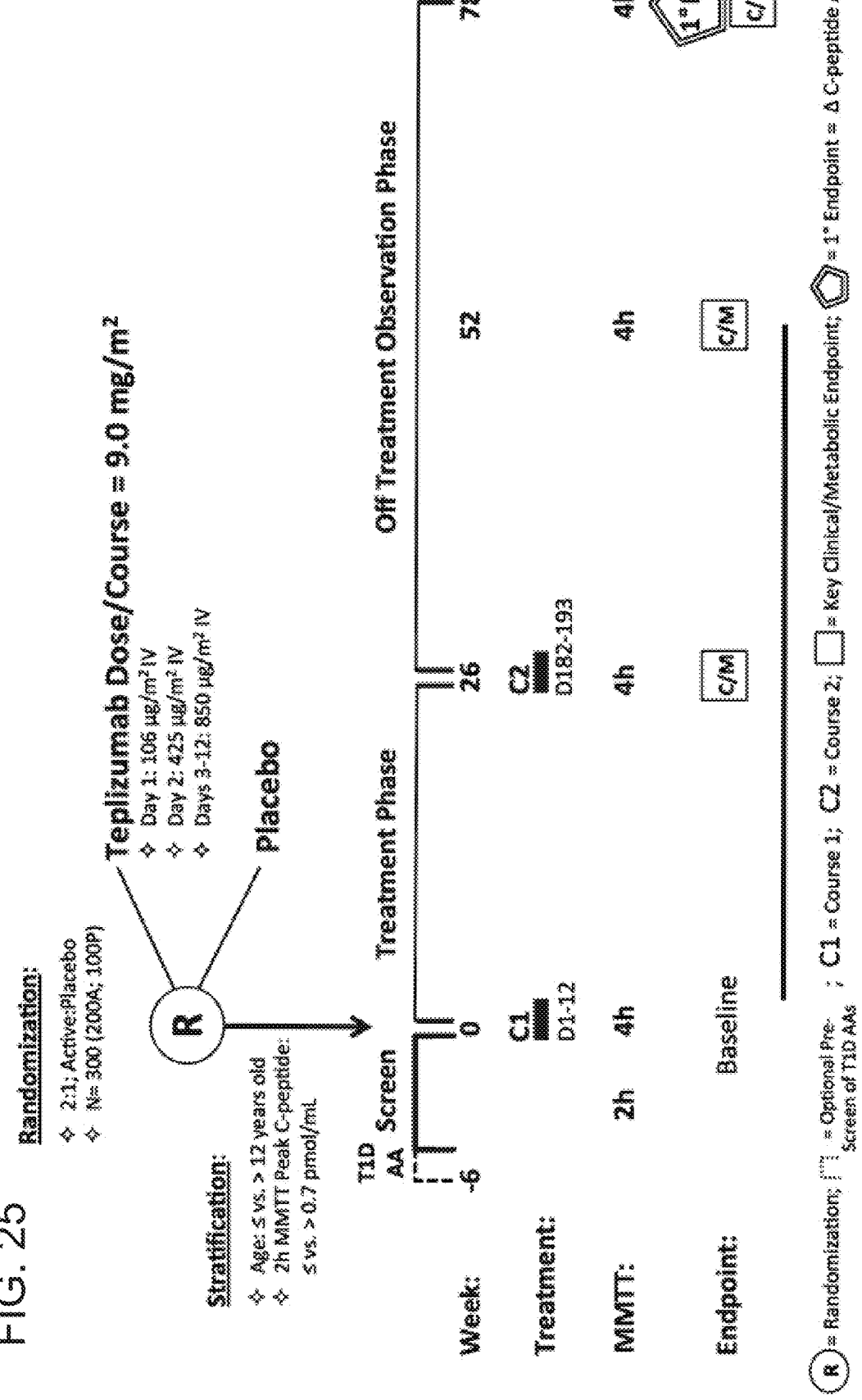

FIG. 25 shows a diagram of the study design according to one embodiment.

FIG. 26 shows Predicted Mean Difference Between Teplizumab and Control in the Change from Baseline in C-Peptide AUC (nmol/L) at 1 Year Follow-up in Supportive Study Meta-Analysis.

FIG. 27 shows Predicted Mean Difference Between Teplizumab and Control in the Change from Baseline in C-peptide AUC (nmol/L) at 2 Year Follow-up in Supportive Study Meta-Analysis.

Figure 28:
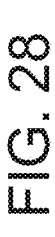

FIG. 28 is a graph showing TN-10: C-Peptide AUCs (nmol/L) in Patients with T1D.

Figure 29:
Figure 29:
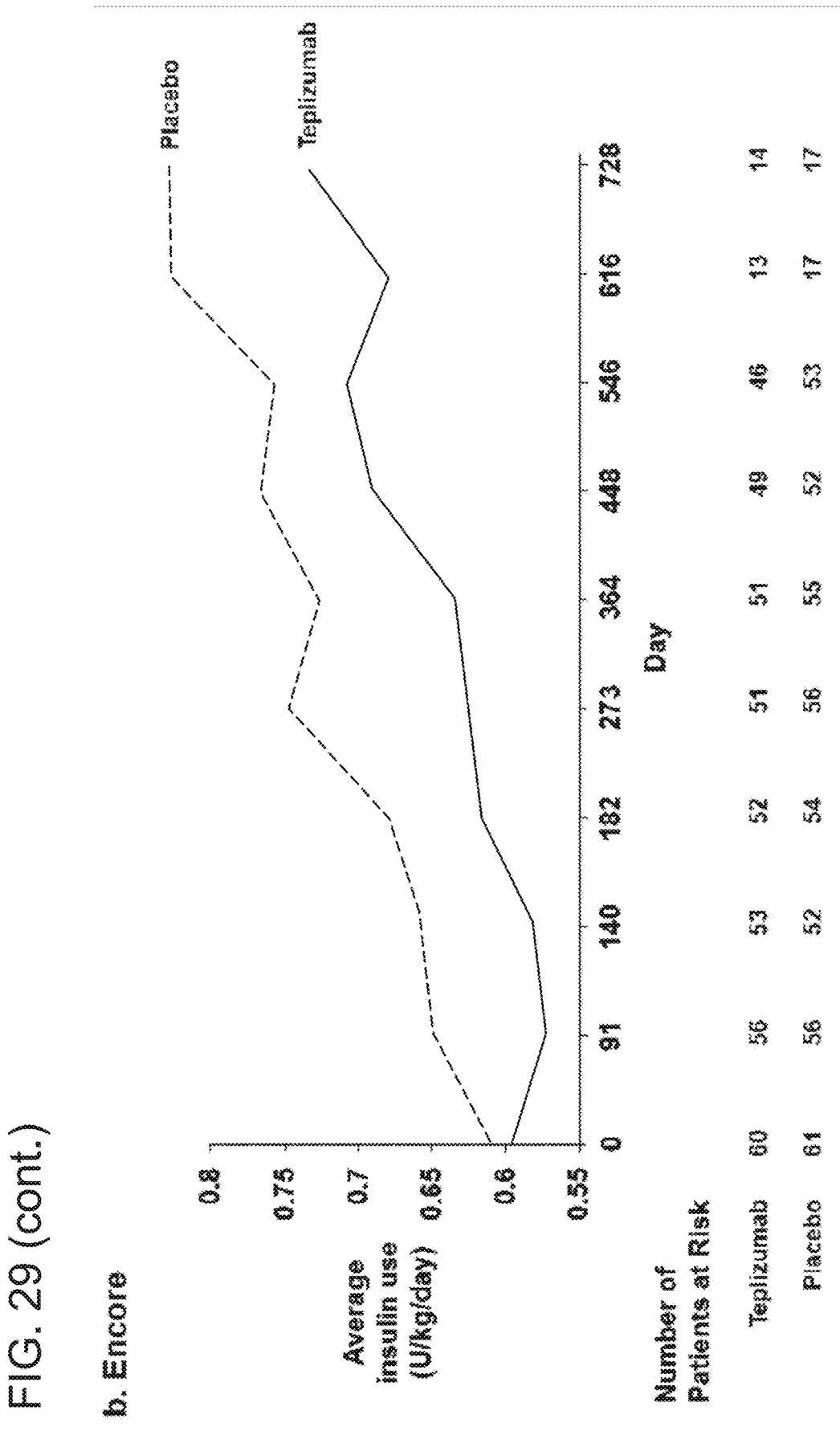
Figure 29:
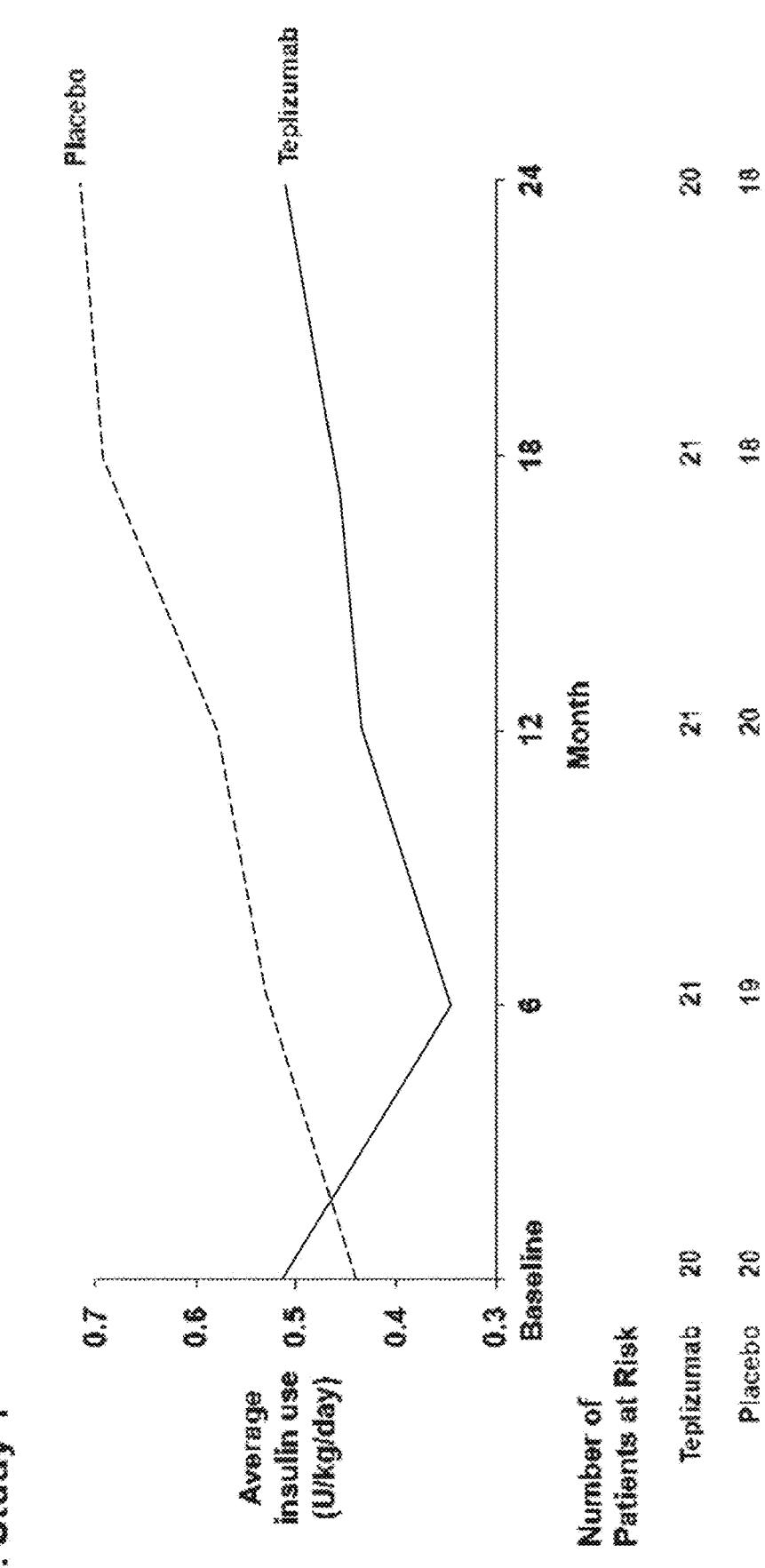
Figure 29:
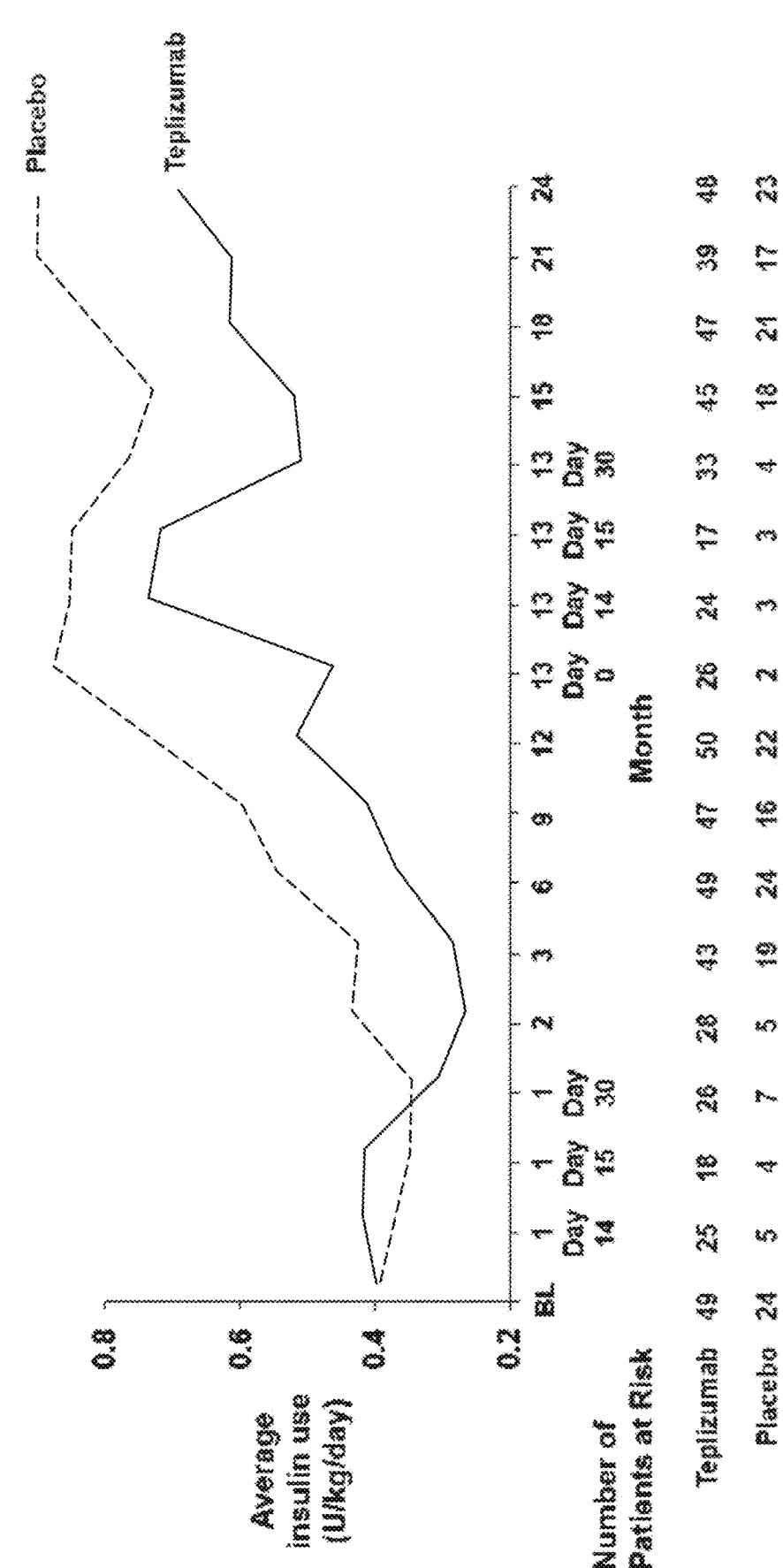
Figure 29:
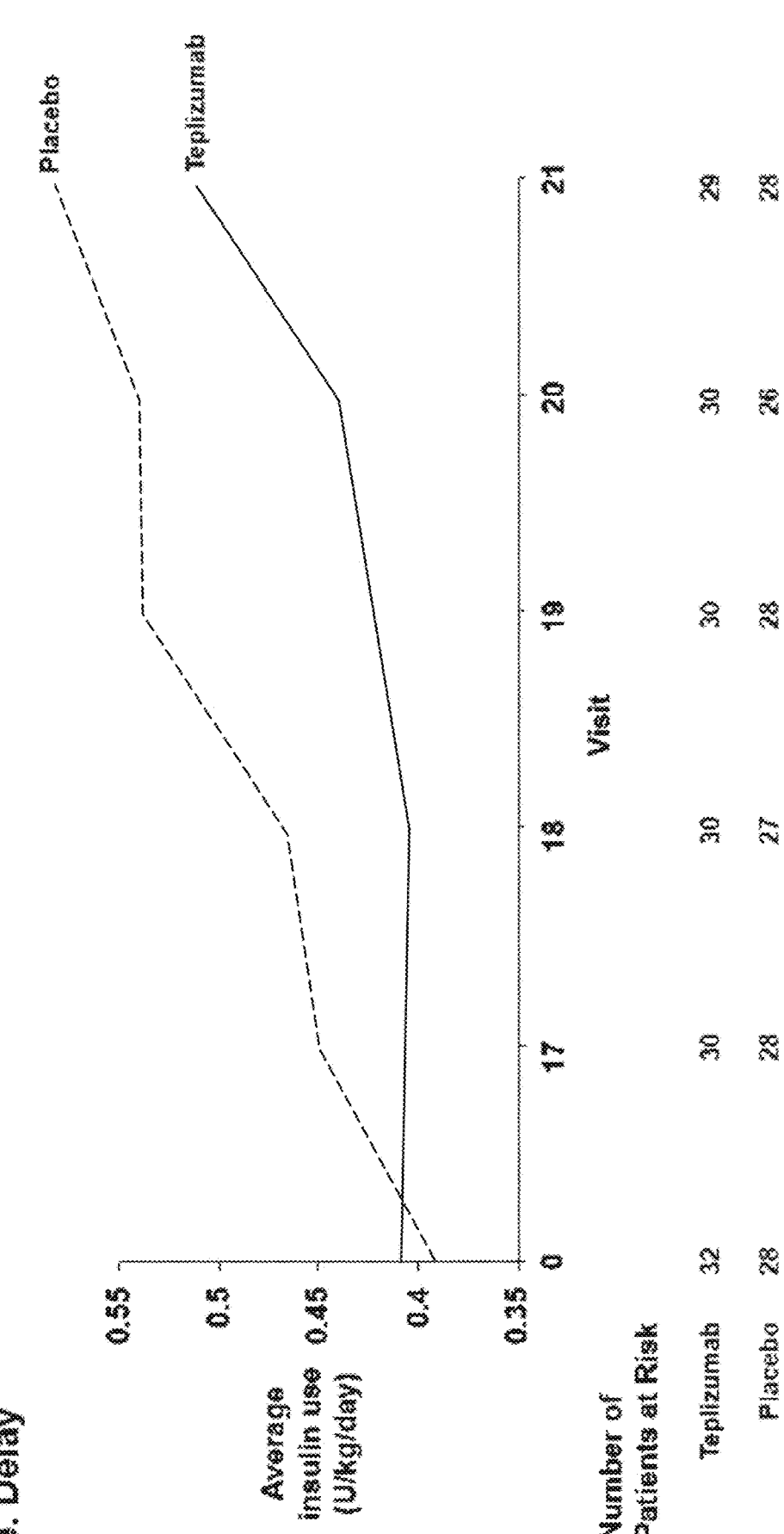

FIGS. 29a-29e are graphs showing Average Insulin Use at Each Visit for Protégé regimen (FIG. 29a), Encore regimen (FIG. 29b), Study 1 regimen (FIG. 29c), AbATE regimen (FIG. 29d) and Delay regimen (FIG. 29e).

Figures 30A, 30B:
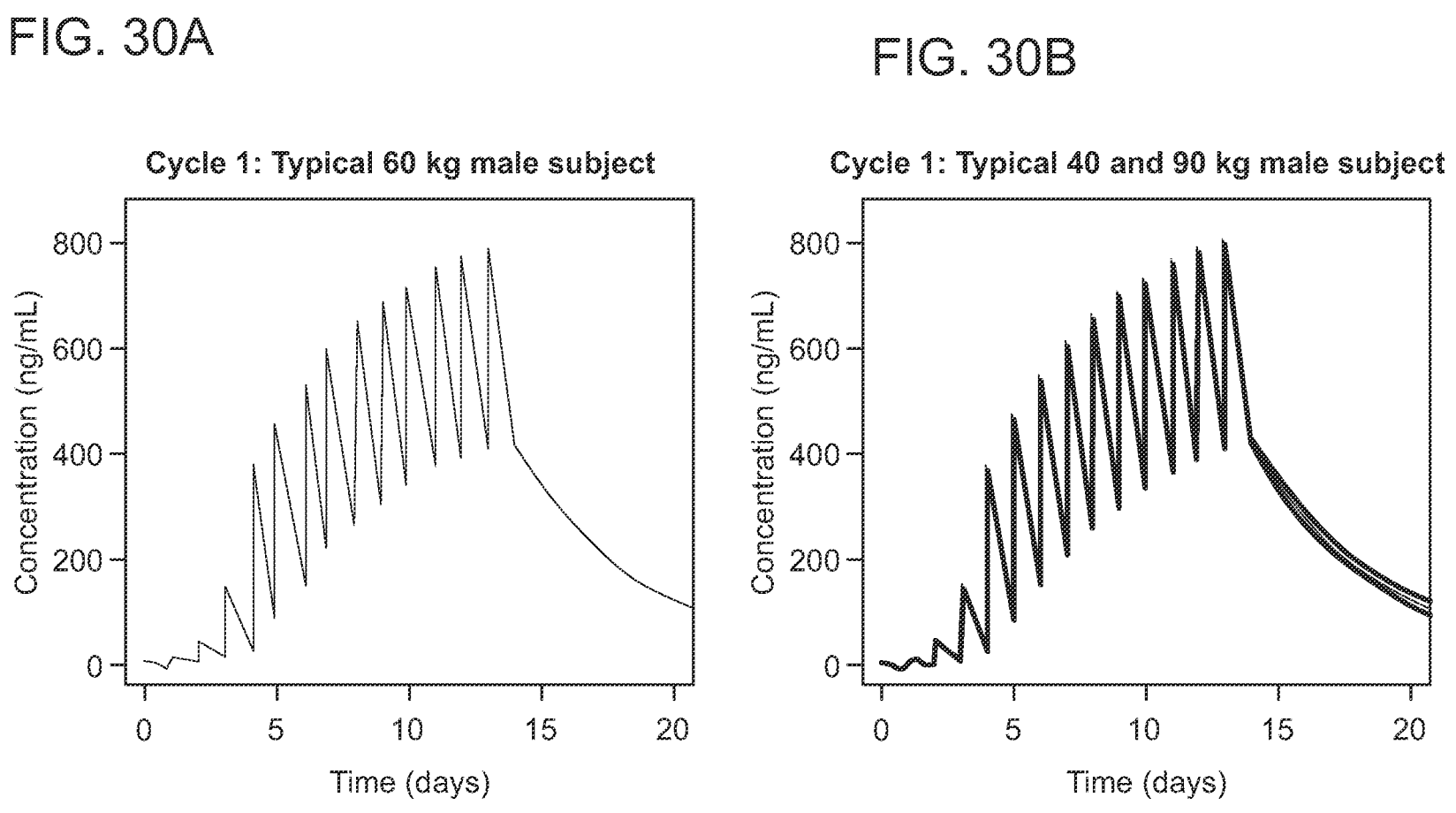

FIGS. 30A-30B are graphs showing Predicted Mean Teplizumab Serum Concentration Versus Time Profile Following 14-Day Regimen Across Different Body Weights.

Figure 31:
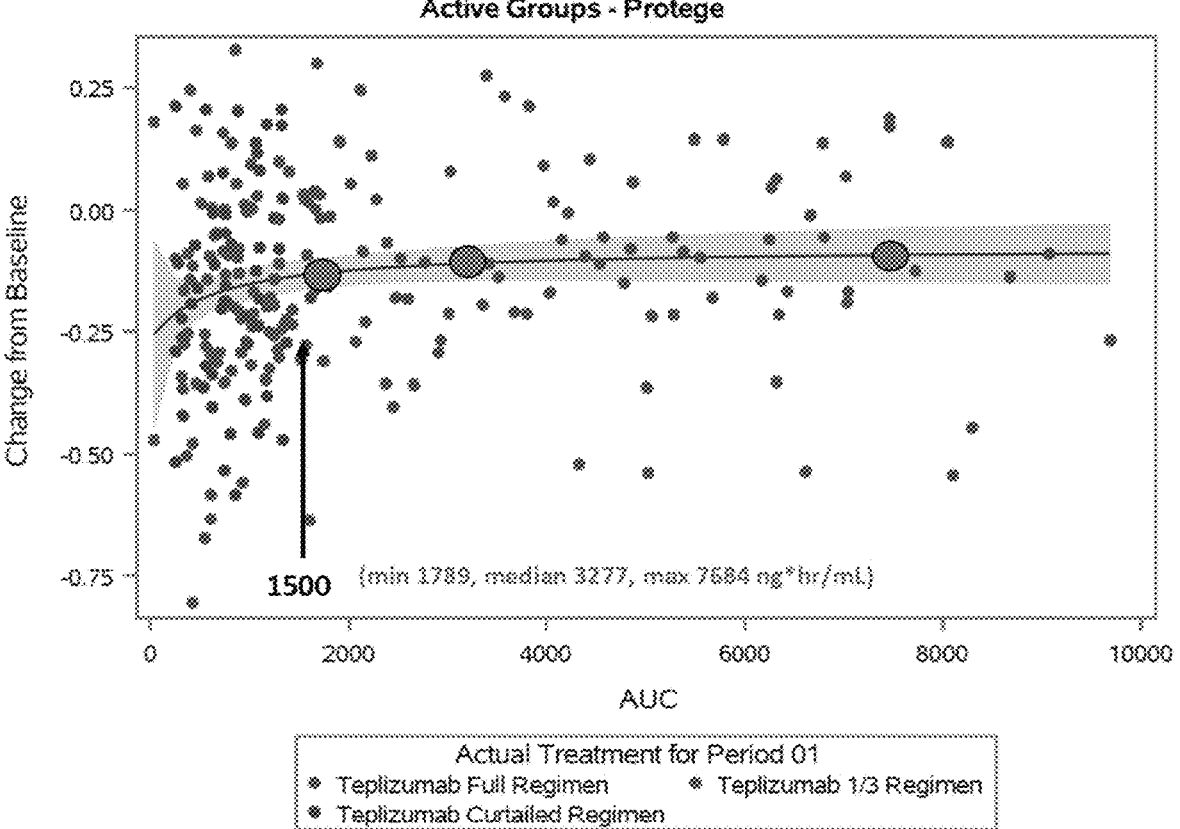

FIG. 31 is a Plot Emax model: predicted C-peptide change vs AUC, Year 2. The Protégé study was conducted in newly diagnosed (Stage 3) T1D patients and tested 3 teplizumab dosing regimens (full 14-day [about 9,030 μg/m² cumulative dose], one-third of the 14-day regimen [1/3], and a 6-day curtailed [first 6 days of the full 14-day regimen]).

DETAILED DESCRIPTION

Type 1 diabetes usually develops in childhood and adolescence; however, it can also present in adulthood as late as the 5th and 6th decades of life, although much less frequently (Atkinson 2014, Bluestone 2010, Streisand 2014). In addition to being more prone to some short- and long-term complications, there are differences in the clinical course and response to immune therapies between children/young adults and older adults. In the days or weeks before initial diagnosis, children and adolescents often suffer from severe diabetes symptoms, including polydipsia, polyuria, and weight loss, which could result in a clinical presentation of DKA and shock which requires hospitalization (Atkinson 2014, Bluestone 2010, Streisand 2014, Mittermayer 2017). Children and young adults with new-onset T1D usually have an immediate need for exogenous insulin.

This sharply contrasts with the experience of adults who develop T1D who often have months or years of non-specific symptoms or present asymptomatically from routine glycemic screening. These individuals can often be managed for prolonged periods of time (months or years) with diet or oral hypoglycemic agents before a demonstrable insulin need. More definitive studies have shown a different rate of decline of β cells according to age (Greenbaum 2012; Ludvigsson 2013). Following decades of study, the Diabetes TrialNet network has concluded that "age is the most important factor impacting the rate of decline of C-peptide post diagnosis" in that a significantly more rapid rate of decline occurs in children and adolescents compared to younger and older adults with new-onset disease. This more rapid decline appears to be due to a much more virulent and aggressive autoimmune process in children compared to adults, ostensibly supporting that there are important differences in T1D immuno-pathoetiology in younger versus older individuals (Greenbaum 2012, Campbell-Thompson 2016). Due to these fundamental differences, it is reasonable to expect that adults and children may respond differently to an immune-based disease modifying therapy. In other words, one treatment may be very effective in children but not effective at all in adults and vice versa (Rigby 2014).

Children and adolescents are those at highest risk of developing disease and suffer most substantially from short- and long-term morbidity and mortality, and thus this group has the most to benefit from a disease modifying therapy (Wherrett 2015). This has recently been reinforced by a large study showing that those diagnosed with T1D in childhood and adolescence have a 4-6-fold increase in lifetime mortality risk, including seven times the risk of mortality from cardiovascular disease, compared to counterparts without T1D. This mortality risk is in sharp contrast to individuals diagnosed with T1D in adulthood, who have a ~3-fold higher risk from all-cause and cardiovascular disease-related mortality compared to their otherwise healthy peers (Rawshani 2017, Rawshani 2018). Recent reports indicate that those with T1D have a life expectancy ~11-13 years less than otherwise healthy-age matched individuals (Lind 2014, Huo 2016). While it is a goal in T1D research to reduce the morbidity and mortality for all with T1D, it is apparent that the most urgent need is for those who develop T1D in childhood and adolescence.

There is therefore a need to develop a therapy for children who can most likely benefit from it.

Aspects of the disclosure relate to methods of treating type 1 diabetes (T1D) in subjects in need thereof. Provided herein are methods that preserve β cell function and improve clinical management of T1D in children compared with the natural course of disease and current standard of care including exogenous insulin therapy. The preservation of β cell function is anticipated to translate to clinical and/or metabolic benefits consistent with improved ability to maintain glycemic control and short- and/or long-term outcomes. In some embodiments, the method comprises diagnosing patients 8 to 17 years of age with T1D, administering to the patients within 6 weeks of diagnosis a first course of daily doses of teplizumab for 12 days, and a second course of daily doses of teplizumab for 12 days, wherein the first and second courses are separated with a 6-month interval. In some embodiments, the method further comprises assessing the area under the time-concentration curve (AUC) of C-peptide following a mixed meal tolerance test (MMTT), at 78 weeks (18 months or 1.5 years), and/or evaluating clinical endpoints such insulin use, HbA1c levels, and hypoglycemic episodes.

Definitions

Certain terms are defined herein below. Additional definitions are provided throughout the application.

As used herein, the articles "a" and "an" refer to one or more than one, e.g., to at least one, of the grammatical object of the article. The use of the words "a" or "an" when used in conjunction with the term "comprising" herein may mean "one," but it is also consistent with the meaning of "one or more," "at least one," and "one or more than one."

As used herein, "about" and "approximately" generally mean an acceptable degree of error for the quantity measured given the nature or precision of the measurements. Exemplary degrees of error are within 20 percent (%), typically, within 10%, and more typically, within 5% of a given range of values. The term "substantially" means more than 50%, preferably more than 80%, and most preferably more than 90% or 95%.

As used herein the term "comprising" or "comprises" is used in reference to compositions, methods, and respective component(s) thereof, that are present in a given embodiment, yet open to the inclusion of unspecified elements.

As used herein the term "consisting essentially of" refers to those elements required for a given embodiment. The term permits the presence of additional elements that do not materially affect the basic and novel or functional characteristic(s) of that embodiment of the disclosure.

The term "consisting of" refers to compositions, methods, and respective components thereof as described herein, which are exclusive of any element not recited in that description of the embodiment.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments.

As used herein, the term "onset" of disease with reference to Type-1 diabetes refers to a patient meeting the criteria established for diagnosis of Type-1 diabetes by the American Diabetes Association (see, Mayfield et al., 2006, Am. Fam. Physician 58:1355-1362).

As used herein, a "protocol" includes dosing schedules and dosing regimens. The protocols herein are methods of use and include therapeutic protocols. A "dosing regimen", "dosage regimen" or "course of treatment" may include administration of several doses of a therapeutic agent over 1 to 20 days.

As used herein, the terms "subject" and "patient" are used interchangeably. As used herein, the terms "subject" and "subjects" refer to an animal, preferably a mammal including a non-primate (e.g., a cow, pig, horse, cat, dog, rat, and mouse) and a primate (e.g., a monkey or a human), and more preferably a human. In some embodiments, the patient population comprises children. In some embodiments, the patient population comprises children newly diagnosed with T1D. In some embodiments, the patient population is treated within 6 weeks of the T1D diagnosis. In some embodiments, the patient population comprises children who are positive for at least one T1D-associated autoantibody and have a peak stimulated C-peptide of ≥0.2 pmol/mL at screening.

As used herein, the term "children" (and variations thereof) includes those being around 8 to 17 years of age.

As used herein, the term "effective amount" refers to that amount of teplizumab sufficient to result in the delay or prevention of the development, recurrence or onset of one or more symptoms of T1D.

As used herein, the terms "treat", "treatment" and "treating" refer to the amelioration of one or more symptoms associated with T1D that results from the administration of one or more CD3 binding molecules. In some embodiments, such terms refer to a reduction in a human's average number of hypoglycemic episodes. In other embodiments, such terms refer to the maintenance of a reference level of C-peptide in the peripheral blood.

In some embodiments, the effective amount reduces one or more T1D symptoms by at least 5%, by at least 10%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%.

Various aspects of the disclosure are described in further detail below. Additional definitions are set out throughout the specification.

Anti-CD3 Antibodies and Pharmaceutical Compositions

The terms "anti-CD3 antibody" and "an antibody that binds to CD3" refer to an antibody or antibody fragment that is capable of binding cluster of differentiation 3 (CD3) with sufficient affinity such that the antibody is useful as a prophylactic, diagnostic and/or therapeutic agent in targeting CD3. In some embodiments, the extent of binding of an anti-CD3 antibody to an unrelated, non-CD3 protein is less than about 10% of the binding of the antibody to CD3 as measured, e.g., by a radioimmunoassay (RIA). In some embodiments, an antibody that binds to CD3 has a dissociation constant (Kd) of <1 µM, <100 nM, <10 nM, <1 nM, <0.1 nM, <0.01 nM, or <0.001 nM (e.g. $10^{-8}$ M or less, e.g. from $10^{-8}$ M to $10^{-13}$ M, e.g., from $10^{-9}$ M to $10^{-13}$ M). In some embodiments, an anti-CD3 antibody binds to an epitope of CD3 that is conserved among CD3 from different species.

In some embodiments, the anti-CD3 antibody can be ChAglyCD3 (otelixizumab). Otelixizumab is a humanized Fc nonbinding anti-CD3, which was evaluated initially in phase 2 studies by the Belgian Diabetes Registry (BDR) and then developed by Tolerx, which then partnered with GSK to conduct the phase 3 DEFEND new onset T1D trials (NCT00678886, NCT01123083, NCT00763451). Otelixizumab is administered IV with infusions over 8 days. See, e.g., Wiczling et al., J. Clin. Pharmacol. 50 (5) (May 2010) 494-506; Keymeulen et al., N Engl J Med. 2005; 352:2598-608; Keymeulen et al., Diabetologia. 2010; 53:614-23; Hagopian et al., Diabetes. 2013; 62:3901-8; Aronson et al., Diabetes Care. 2014; 37:2746-54; Ambery et al., Diabet Med. 2014; 31:399-402; Bolt et al., Eur. J. Immunol. 1YY3. 23:403-411; Vlasakakis et al., Br J Clin Pharmacol (2019) 85 704-714; Guglielmi et al, Expert Opinion on Biological Therapy, 16:6, 841-846; Keymeulen et al., N Engl J Med 2005; 352:2598-608; Keymeulen et al., BLOOD 2010, VOL 115, No. 6; Sprangers et al., Immunotherapy (2011) 3 (11), 1303-1316; Daifotis et al., Clinical Immunology (2013) 149, 268-278; all incorporated herein by reference.

In some embodiments, the anti-CD3 antibody can be visilizumab (also called HuM291; Nuvion). Visilizumab is a humanized anti-CD3 monoclonal antibody characterized by a mutated IgG2 isotype, lack of binding to Fcγ receptors, and the ability to induce apoptosis selectively in activated T cells. It was evaluated in patients in graft-versus-host disease (NCT00720629; NCT00032279) and in ulcerative colitis (NCT00267306) and Crohn's Disease (NCT00267709). See, e.g., Sandborn et al., Gut 59 (11) (November 2010) 1485-1492, incorporated herein by reference.

Teplizumab

In some embodiments, the anti-CD3 antibody can be teplizumab. Teplizumab, also known as hOKT3y1(Ala-Ala) (containing an alanine at positions 234 and 235) is an anti-CD3 antibody that had been engineered to alter the function of the T lymphocytes that mediate the destruction of the insulin-producing beta cells of the islets of the pancreas. Teplizumab binds to an epitope of the CD38 chain expressed on mature T cells and by doing so changes their function. Circulating T cells (and other lymphocytes) are transiently reduced following teplizumab treatment, in a process that may include margination and depletion (Long 2017, Sherry 2011). In addition to reduced effector function of T cells, teplizumab appears to both increase the number and function of regulatory T cells (Tregs) (Ablamunits 2010, Bisikirska 2005, Long 2017, Waldron-Lynch 2012). More recent studies indicate that teplizumab induces immunologic "exhaustion" in a subset of effector CD8+ T cells, perhaps making them more susceptible to regulation or deletion (Long 2016, Long 2017). Taken together, these mechanistic data suggest that teplizumab not only exerts a "suppressive" effect on β cell immune destructive processes but rather is an immune "modulator" favoring a rebalancing of effector and regulatory arms involved with T1D autoimmunity and supporting the notion that teplizumab may have the ability to contribute to the re-introduction of β cell self-tolerance (Lebastchi 2013).

Sequences and compositions of teplizumab are disclosed in U.S. Pat. Nos. 6,491,916; 8,663,634; and 9,056,906, each incorporated herein by reference in its entirety. The molecular weight of teplizumab is approximately 150 KD. The full sequences of light and heavy chains are set forth below. Bolded portions are the complementarity determining regions.

```
Teplizumab Light Chain (SEQ ID NO: 1):
DIQMTQSPSSLSASVGDRVTITCSASSSVSYMNWYQQTPGKAPKRWIYDT

SKLASGVPSRFSGSGSGTDYTFTISSLQPEDIATYYCQQWSSNPFTFGQG

TKLQITRTVAAPSVFIFPPSDEQLKSGTASVVCLLNNFYPREAKVQWKVD

NALQSGNSQESVTEQDSKDSTYSLSSTLTLSKADYEKHKVYACEVTHQGL

SSPVTKSFNRGEC

Teplizumab Heavy Chain (SEQ ID NO: 2):
QVQLVQSGGGVVQPGRSLRLSCKASGYTFTRYTMHWVRQAPGKGLEWIGY

INPSRGYTNYNQKVKDRFTISRDNSKNTAFLQMDSLRPEDTGVYFCARYY

DDHYCLDYWGQGTPVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPAPEAAGGPSVFLFPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSRDELTKNQVSLTCLVKGFYPSDIAVEWESNGQPENNYKTTPPVL

DSDGSFFLYSKLTVDKSRWQQGNVFSCSVMHEALHNHYTQKSLSLSPGK
```

In some embodiments, provided herein, is a pharmaceutical composition. Such compositions comprise an effective amount of an anti-CD3 antibody, and a pharmaceutically acceptable carrier. In some embodiments, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously.

Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like (See, for example, Handbook of Pharmaceutical Excipients, Arthur H. Kibbe (ed., 2000, which is incorporated by reference herein in its entirety), Am. Pharmaceutical Association, Washington, D.C.

The composition, if desired, can also contain minor amounts of wetting or emulsifying agents, or pH buffering agents. These compositions can take the form of solutions, suspensions, emulsion, tablets, pills, capsules, powders, sustained release formulations and the like. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions contain a therapeutically effective amount of a therapeutic agent preferably in purified form, together with a suitable amount of carrier so as to provide the form for proper administration to the patient. The formulation should suit the mode of administration. In some embodiments, the pharmaceutical compositions are sterile and in suitable form for administration to a subject, preferably an animal subject, more preferably a mammalian subject, and most preferably a human subject.

In some embodiments, it may be desirable to administer the pharmaceutical compositions locally to the area in need of treatment; this may be achieved by, for example, and not by way of limitation, local infusion, by injection, or by means of an implant, said implant being of a porous, non-porous, or gelatinous material, including membranes, such as sialastic membranes, or fibers. Preferably, when administering the anti-CD3 antibody, care must be taken to use materials to which the anti-CD3 antibody does not absorb.

In some embodiments, the composition can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.).

In some embodiments, the composition can be delivered in a controlled release or sustained release system. In some embodiments, a pump may be used to achieve controlled or sustained release (see Langer, supra; Sefton, 1987, CRC Crit. Ref. Biomed. Eng. 14:20; Buchwald et al., 1980, Surgery 88:507; Saudek et al., 1989, N. Engl. J. Med. 321:574). In some embodiments, polymeric materials can be used to achieve controlled or sustained release of the antibodies of the disclosure or fragments thereof (see e.g., Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, J., Macromol. Sci. Rev. Macromol. Chem. 23:61; see also Levy et al., 1985, Science 228:190; During et al., 1989, Ann. Neurol. 25:351; Howard et al., 1989, J. Neurosurg. 71:105); U.S. Pat. Nos. 5,679,377; 5,916,597; 5,912,015; 5,989,463; 5,128,326; PCT Publication No. WO 99/15154; and PCT Publication No. WO 99/20253. Examples of polymers used in sustained release formulations include, but are not limited to, poly(2-hydroxy ethyl methacrylate), poly(methyl methacrylate), poly (acrylic acid), poly(ethylene-co-vinyl acetate), poly(methacrylic acid), polyglycolides (PLG), polyanhydrides, poly (N-vinyl pyrrolidone), poly(vinyl alcohol), polyacrylamide, poly(ethylene glycol), polylactides (PLA), poly(lactide-co-glycolides) (PLGA), and polyorthoesters. In some embodiments, the polymer used in a sustained release formulation is inert, free of leachable impurities, stable on storage, sterile, and biodegradable. In some embodiments, a controlled or sustained release system can be placed in proximity of the therapeutic target, i.e., the lungs, thus requiring only a fraction of the systemic dose (see, e.g., Goodson, in Medical Applications of Controlled Release, supra, vol. 2, pp. 115-138 (1984)).

Controlled release systems are discussed in the review by Langer (1990, Science 249:1527-1533). Any technique known to one of skill in the art can be used to produce sustained release formulations comprising one or more antibodies of the disclosure or fragments thereof. See, e.g., U.S. Pat. No. 4,526,938; PCT Publication No. WO 91/05548; PCT Publication No. WO 96/20698; Ning et al., 1996, Radiotherapy & Oncology 39:179-189; Song et al., 1995, PDA Journal of Pharmaceutical Science & Technology 50:372-397; Cleek et al., 1997, Pro. Int'l. Symp. Control. Rel. Bioact. Mater. 24:853-854; and Lam et al., 1997, Proc. Int'l. Symp. Control Rel. Bioact. Mater. 24:759-760, each of which is incorporated herein by reference in its entirety.

A pharmaceutical composition can be formulated to be compatible with its intended route of administration. Examples of routes of administration include, but are not limited to, parenteral, e.g., intravenous, intradermal, subcutaneous, oral, intranasal (e.g., inhalation), transdermal (topical), transmucosal, and rectal administration. In some embodiments, the composition is formulated in accordance with routine procedures as a pharmaceutical composition adapted for intravenous, subcutaneous, intramuscular, oral, intranasal or topical administration to human beings. In some embodiments, a pharmaceutical composition is formulated in accordance with routine procedures for subcutaneous administration to human beings. Typically, compositions for intravenous administration are solutions in sterile isotonic aqueous buffer. Where necessary, the composition may also include a solubilizing agent and a local anesthetic such as lignocamne to ease pain at the site of the injection.

The compositions may be formulated for parenteral administration by injection, e.g., by bolus injection or continuous infusion. Formulations for injection may be presented in unit dosage form, e.g., in ampoules or in multidose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

In some embodiments, the disclosure provides dosage forms that permit administration of the anti-CD3 antibody continuously over a period of hours or days (e.g., associated with a pump or other device for such delivery), for example, over a period of 1 hour, 2 hours, 3 hours, 4 hours, 6 hours, 8 hours, 10 hours, 12 hours, 16 hours, 20 hours, 24 hours, 30 hours, 36 hours, 4 days, 5 days, 7 days, 10 days or 12 days. In some embodiments, the disclosure provides dosage forms that permit administration of a continuously increasing dose, for example, increasing from 106 ug/m$^2$/day to 850 ug/m$^2$/day or 211 ug/m$^2$/day to 840 ug/m$^2$/day over a period of 24 hours, 30 hours, 36 hours, 4 days, 5 days, 7 days, 10 days or 12 days.

The compositions can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

Generally, the ingredients of the compositions disclosed herein are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

In particular, the disclosure provides that the anti-CD3 antibodies, or pharmaceutical compositions thereof, can be packaged in a hermetically sealed container such as an ampoule or sachette indicating the quantity of the agent. In some embodiments, the anti-CD3 antibody, or pharmaceutical compositions thereof is supplied as a dry sterilized lyophilized powder or water free concentrate in a hermetically sealed container and can be reconstituted, e.g., with water or saline to the appropriate concentration for administration to a subject. Preferably, the anti-CD3 antibody, or pharmaceutical compositions thereof is supplied as a dry sterile lyophilized powder in a hermetically sealed container at a unit dosage of at least 5 mg, more preferably at least 10 mg, at least 15 mg, at least 25 mg, at least 35 mg, at least 45 mg, at least 50 mg, at least 75 mg, or at least 100 mg. The lyophilized agents, or pharmaceutical compositions herein should be stored at between 2° C. and 8° C. in its original container and the therapeutic agents, or pharmaceutical compositions of the disclosure should be administered within 1 week, preferably within 5 days, within 72 hours, within 48 hours, within 24 hours, within 12 hours, within 6 hours, within 5 hours, within 3 hours, or within 1 hour after being reconstituted. In some embodiments, the pharmaceutical composition is supplied in liquid form in a hermetically sealed container indicating the quantity and concentration of the agent. Preferably, the liquid form of the administered composition is supplied in a hermetically sealed container at least 0.25 mg/ml, more preferably at least 0.5 mg/ml, at least 1 mg/ml, at least 2.5 mg/ml, at least 5 mg/ml, at least 8 mg/ml, at least 10 mg/ml, at least 15 mg/ml, at least 25 mg/ml, at least 50 mg/ml, at least 75 mg/ml or at least 100 mg/ml. The liquid form should be stored at between 2° C. and 8° C. in its original container.

In some embodiments, the disclosure provides that the composition of the disclosure is packaged in a hermetically sealed container such as an ampoule or sachette indicating the quantity of the anti-CD3 antibody.

The compositions may, if desired, be presented in a pack or dispenser device that may contain one or more unit dosage forms containing the active ingredient. The pack may, for example, comprise metal or plastic foil, such as a blister pack.

The amount of the composition of the disclosure which is effective in the treatment of one or more symptoms associated with T1D can be determined by standard clinical techniques. The precise dose to be employed in the formulation can also depend on the route of administration and the seriousness of the condition, and should be decided according to the judgment of the practitioner and each patient's circumstances. Effective doses may be extrapolated from dose-response curves derived from in vitro or animal model test systems.

Methods and Use

In some embodiments, the present disclosure encompasses administration of anti-human CD3 antibodies such as teplizumab to patients 8 through 17 years old 6 weeks from T1D diagnosis having a peak C-peptide level of ≥0.2 pmol/mL during a mixed meal tolerance test (MMTT). In some embodiments, the peak C-peptide level at screening rages from 0.2 pmol/mL (inclusive) to 0.7 pmol/mL (inclusive).

In some embodiments, T1D diagnosis is according to the American Diabetes Association (ADA) criteria. As defined by the American Diabetes Association (ADA) for the clinical diagnosis of diabetes, the individual must meet one of the following 4 criteria:

A fasting plasma glucose (FPG) of ≥126 mg/dL (7.0 mmol/L). Fasting is defined as no caloric intake for at least 8 hours.

A 2-hour plasma glucose (PG) of ≥200 mg/dL (11.1 mmol/L) during an oral glucose tolerance test (OGTT). The test should be performed as described by the World Health Organization (WHO), using a glucose load containing the equivalent of 75 g anhydrous glucose dissolved in water.

A hemoglobin A1C (HbA1c) of ≥6.5% (48 mmol/mol). The test should be performed in a laboratory using a method that is National Glycohemoglobin Standardization Program (NGSP) certified and standardized to the Diabetes Control and Complications Trial (DCCT) assay.

In a patient with classic symptoms of hyperglycemia or hyperglycemic crisis, a random PG of ≥200 mg/dl (11.1 mmol/L).

For the diagnosis of clinical Type 1 diabetes (T1D), the ADA suggests that plasma blood glucose rather than HbA1C should be used to diagnose the acute onset of T1D in individuals with symptoms of hyperglycemia.

According to ADA, a patient with classic symptoms, measurement of plasma glucose is sufficient to diagnose clinical diabetes (symptoms of hyperglycemia or hyperglycemic crisis plus a random plasma glucose ≥200 mg/dL [11.1 mmol/L]). In these cases, knowing the plasma glucose level is critical because, in addition to confirming that symptoms are due to diabetes, it will inform management decisions. Some providers may also want to know the HbA1C to determine how long a patient has had hyperglycemia. In addition, T1D, previously called "insulin-dependent diabetes" or "juvenile-onset diabetes," accounts for 5-10% of diabetes and is due to cellular-mediated autoimmune destruction of the pancreatic β-cells. Autoimmune markers include islet cell autoantibodies and autoantibodies to GAD (GAD65), insulin, the tyrosine phosphatases IA-2 and IA-2 β, and ZnT8. T1D is defined by the presence of one or more of these autoimmune markers.

In some embodiments, the diagnosis of T1D is made with the use of a continuous glucose monitoring system (CGM) revealing high sensor average glucose levels (>=110 mg/dL), or high variability of glycemia (CV >=15), or less time in range (>=10% of the time above 140 mg/dL).

In some embodiments, the patient diagnosed with clinical T1D has a positive result on testing for at least one of the following T1D-related autoantibodies: Glutamic acid decarboxylase 65 (GAD65) autoantibodies, Islet antigen 2 (IA-2) autoantibodies, Zinc transporter 8 (ZnT8) autoantibodies Islet cell cytoplasmic autoantibodies (ICA) or Insulin autoantibodies (if testing obtained within the first 14 days of insulin treatment). In some embodiments, the presence of the autoantibodies is detected by ELISA, electrochemoluminescence (ECL), radioassay (see, e.g., Yu et al., 1996, J. Clin. Endocrinol. Metab. 81:4264-4267), agglutination PCR (Tsai et al, *ACS Central Science* 2016 2 (3), 139-147) or by any other method for immunospecific detection of antibodies described herein or as known to one of ordinary skill in the art.

It is recognized that β cells continue to be lost following T1D diagnosis. To maximize the effect of β cell preservation in patients with a recoverable level endogenous insulin production, the patients to be treated are within 6 weeks from T1D diagnosis and have a peak C-peptide level of ≥0.2 pmol/mL during a mixed meal tolerance test (MMTT).

In some embodiments, the methods provided herein prevents or delays the need for administration of insulin to the patients.

β-cell function prior to, during, and after therapy may be assessed by methods described herein or by any method known to one of ordinary skill in the art. For example, the Diabetes Control and Complications Trial (DCCT) research group has established the monitoring of percentage glycosylated hemoglobin (HA1 and HA1c) as the standard for evaluation of blood glucose control (DCCT, 1993, N. Engl. J. Med. 329:977-986). Alternatively, characterization of daily insulin needs, C-peptide levels/response, hypoglycemic episodes, and/or FPIR may be used as markers of β-cell function or to establish a therapeutic index (See Keymeulen et al., 2005, N. Engl. J. Med. 352:2598-2608; Herold et al., 2005, Diabetes 54:1763-1769; U.S. Pat. Appl. Pub. No. 2004/0038867 A1; and Greenbaum et al., 2001, Diabetes 50:470-476, respectively). For example, FPIR is calculated as the sum of insulin values at 1 and 3 minutes post IGTT, which are performed according to Islet Cell Antibody Register User's Study protocols (see, e.g., Bingley et al., 1996, Diabetes 45:1720-1728 and McCulloch et al., 1993, Diabetes Care 16:911-915).

In some embodiments, the effective amount comprises a 12-day course of subcutaneous intravenous (IV) infusion of the anti-CD3 antibody such as teplizumab at 106-850 micrograms/meter squared (ug/m²). In some embodiments, the total dosage over the duration of the regimen is about 14000 ug/m², 13500 ug/m², 13000 ug/m², 12500 ug/m², 12000 ug/m², 11500 ug/m², 11000 ug/m², 10500 ug/m², 10000 ug/m², 9500 ug/m², 9000 ug/m², 8000 ug/m², 7000 ug/m², 6000 ug/m², and may be less than 5000 ug/m², 4000 ug/m², 3000 ug/m², 2000 ug/m², or 1000 ug/m². In some embodiments, the total dosage over the duration of the regimen is from about 9030 ug/m² to about 14000 ug/m², about 9030 ug/m² to about 13500 ug/m², about 9000 ug/m² to about 13000 ug/m², about 9000 ug/m² to about 12500 ug/m², about 9000 ug/m² to about 12000 ug/m², about 9000 ug/m² to about 11500 ug/m², about 9000 ug/m² to about 11000 ug/m², about 9000 ug/m² to about 10500 ug/m², about 9000 ug/m² to about 10000 ug/m², about 9000 ug/m² to about 9500 ug/m². In some embodiments, the total dosage over the duration of the regimen is from about 9030 ug/m² to about 14000 ug/m², about 9030 ug/m² to about 13500 ug/m², about 9030 ug/m² to about 13000 ug/m², about 9030 ug/m² to about 12500 ug/m², about 9030 ug/m² to about 12000 ug/m², about 9030 ug/m² to about 11500 ug/m², from about 9030 ug/m² to about 11000 ug/m², about 9030 ug/m² to about 10500 ug/m², about 9030 ug/m² to about 10000 ug/m², about 9030 ug/m² to about 9500 ug/m².

Without being bound by the theory, cumulative doses above about 9,000 ug/m$^2$ of teplizumab are expected to have comparable efficacy in terms of C-peptide preservation as shown for about 9,000 mg. That is because the exposure/response curve surprisingly reaches a plateau above which increasing doses do not result in increased efficacy. The evaluation of C-peptide preservation was performed utilizing the Protégé study data. Model-predicted teplizumab AUCs versus change from baseline in C-peptide were plotted and an Emax analysis was performed. These data demonstrate that an Emax model describes the relationship between teplizumab exposure and change in C-peptide at 2 years. As shown in FIG. 31, at teplizumab AUC levels greater than about 1500 ng*hr/mL (below the lowest AUC predicted for the about 9,000 ug/m$^2$ dose, of 1,789 ng*hr/mL) no additional improvement in C-peptide with increased teplizumab exposure was observed. Therefore, these data suggest that doses above about 9,000 mg of teplizumab would have comparable efficacy in terms of C-peptide preservation as shown for about 9,000 mg.

In some embodiments, the effective amount comprises a 12-day course IV infusion of teplizumab at a first dose of 106 ug/m$^2$ teplizumab on day 1, a second dose of 425 ug/m$^2$ teplizumab on day 2, and one dose of 850 ug/m$^2$ on each of days 3-12. In some embodiments, the effective amount comprises a 12-day course IV infusion of teplizumab at a first dose of 211 ug/m$^2$ teplizumab on day 1, a second dose of 423 ug/m$^2$ teplizumab on day 2, and one dose of 840 ug/m$^2$ on each of days 3-12. In some embodiments, the effective amount comprises a 12-day course IV infusion of teplizumab at a first dose of approximately 100 ug/m$^2$ teplizumab on day 1, a second dose of approximately 400 ug/m$^2$ teplizumab on day 2, a third dose of approximately 850 ug/m$^2$ on day 3, and approximately 1,200 ug/m$^2$ on each of days 4-12. In some embodiments, the effective amount comprises a 12-day course IV infusion of teplizumab at a first dose of approximately 100 ug/m$^2$ teplizumab on day 1, a second dose of approximately 400 ug/m$^2$ teplizumab on day 2, a third dose of approximately 850 ug/m$^2$ on day 3, and approximately 1,300 ug/m$^2$ on each of days 4-12. In some embodiments, the effective amount comprises a 12-day course IV infusion of teplizumab at a first dose of approximately 100 ug/m$^2$ teplizumab on day 1, a second dose of approximately 400 ug/m$^2$ teplizumab on day 2, a third dose of approximately 850 ug/m$^2$ on day 3, and approximately 1,400 ug/m$^2$ on each of days 4-12. In some embodiments, the effective amount comprises a 12-day course IV infusion of teplizumab at a first dose of approximately 200 ug/m$^2$ teplizumab on day 1, a second dose of approximately 400 ug/m$^2$ teplizumab on day 2, a third dose of approximately 850 ug/m$^2$ on day 3, and approximately 1,200 ug/m$^2$ on each of days 4-12. In some embodiments, the effective amount comprises a 12-day course IV infusion of teplizumab at a first dose of approximately 200 ug/m$^2$ teplizumab on day 1, a second dose of approximately 400 ug/m$^2$ teplizumab on day 2, a third dose of approximately 850 ug/m$^2$ on day 3, and approximately 1,300 ug/m$^2$ on each of days 4-12. In some embodiments, the effective amount comprises a 12-day course IV infusion of teplizumab at a first dose of approximately 200 ug/m$^2$ teplizumab on day 1, a second dose of approximately 400 ug/m$^2$ teplizumab on day 2, a third dose of approximately 850 ug/m$^2$ on day 3, and approximately 1,400 ug/m$^2$ on each of days 4-12.

Provided herein is a dosing regimen comprising two or more courses of dosing with an anti-CD3 antibody such as teplizumab comprising a first course of dosing at week 1 and second course of dosing at week 26. In some embodiments, teplizumab is administered via IV infusion in two courses, with the first course starting on Day 1 (Week 1) and the second course on approximately Day 182 (Week 26), each course of treatment including daily infusions for 12 days, with a cumulative teplizumab dose of 9000 ug/m$^2$ for each course of treatment. In some embodiments, teplizumab is administered via IV infusion in two courses, with the first course starting on Day 1 (Week 1) and the second course on approximately Day 182 (Week 26), each course of treatment including daily infusions for 12 days, with a cumulative teplizumab dose of 9500 ug/m$^2$ for each course of treatment. In some embodiments, teplizumab is administered via IV infusion in two courses, with the first course starting on Day 1 (Week 1) and the second course on approximately Day 182 (Week 26), each course of treatment including daily infusions for 12 days, with a cumulative teplizumab dose of 10000 ug/m$^2$ for each course of treatment. In some embodiments, teplizumab is administered via IV infusion in two courses, with the first course starting on Day 1 (Week 1) and the second course on approximately Day 182 (Week 26), each course of treatment including daily infusions for 12 days, with a cumulative teplizumab dose of 10500 ug/m$^2$ for each course of treatment. In some embodiments, teplizumab is administered via IV infusion in two courses, with the first course starting on Day 1 (Week 1) and the second course on approximately Day 182 (Week 26), each course of treatment including daily infusions for 12 days, with a cumulative teplizumab dose of 11000 ug/m$^2$ for each course In some embodiments, teplizumab is administered via IV infusion in two courses, with the first course starting on Day 1 (Week 1) and the second course on approximately Day 182 (Week 26), each course of treatment including daily infusions for 12 days, with a cumulative teplizumab dose of 11500 ug/m$^2$ for each course of treatment. of treatment. In some embodiments, teplizumab is administered via IV infusion in two courses, with the first course starting on Day 1 (Week 1) and the second course on approximately Day 182 (Week 26), each course of treatment including daily infusions for 12 days, with a cumulative teplizumab dose of 12000 ug/m$^2$ for each course of treatment. In some embodiments, teplizumab is administered via IV infusion in two courses, with the first course starting on Day 1 (Week 1) and the second course on approximately Day 182 (Week 26), each course of treatment including daily infusions for 12 days, with a cumulative teplizumab dose of 12500 ug/m$^2$ for each course of treatment. In some embodiments, teplizumab is administered via IV infusion in two courses, with the first course starting on Day 1 (Week 1) and the second course on approximately Day 182 (Week 26), each course of treatment including daily infusions for 12 days, with a cumulative teplizumab dose of 13000 ug/m$^2$ for each course of treatment. In some embodiments, teplizumab is administered via IV infusion in two courses, with the first course starting on Day 1 (Week 1) and the second course on approximately Day 182 (Week 26), each course of treatment including daily infusions for 12 days, with a cumulative teplizumab dose of 13500 ug/m$^2$ for each course of treatment. In some embodiments, teplizumab is administered via IV infusion in two courses, with the first course starting on Day 1 (Week 1) and the second course on approximately Day 182 (Week 26), each course of treatment including daily infusions for 12 days, with a cumulative teplizumab dose of 14000 ug/m$^2$ for each course of treatment. In some embodiments, the 12 days course has a 2-day ramp-up phase and a 10-day fixed-, maximal dosing period. In some embodiments, 106 ug/m$^2$ teplizumab is administered on day 1, 425 ug/m$^2$ teplizumab teplizumab is administered on day 2, and 850 ug/m$^2$ teplizumab is administered on each of days 3-12

In other embodiments, the course of dosing can be repeated at 2 month, 4 month, 5 month, 6 month, 8 month, 9 month, 10 month, 12 month, 15 month, 18 month, 24 month, 30 month, or 36 month intervals. In some embodiments, efficacy of the treatment with the anti-CD3 antibody such as teplizumab is determined as described herein, or as is known in the art, at 2 months, 4 months, 5 month, 6 months, 9 months, 12 months, 15 months, 18 months, 24 months, 30 months, or 36 months subsequent to the previous treatment.

In some embodiments, a subject is administered one or more doses, preferably 12 daily doses, of the anti-CD3 antibody such as teplizumab at about 5-1200 ug/m$^2$, preferably, 106-850 ug/m$^2$ to treat, or slow the progression of or ameliorate one or more symptoms of T1D.

In some embodiments, the subject is administered a treatment regimen comprising two courses of daily doses of an effective amount of the anti-CD3 antibody such as teplizumab, wherein the course of treatment is administered over 2 days, 3 days, 4 days, 5 days, 6 days, 7 days, 8 days, 9 days, 10 days, 11 days or 12 days. In some embodiments, the treatment regimen comprises administering doses of the effective amount every day, every 2nd day, every 3rd day or every 4th day.

In some embodiments, a subject is administered a treatment regimen comprising one or more doses of a prophylactically effective amount of the anti-CD3 antibody such as teplizumab, wherein the prophylactically effective amount is 200 ug/kg/day, 175 ug/kg/day, 150 ug/kg/day, 125 ug/kg/day, 100 ug/kg/day, 95 ug/kg/day, 90 ug/kg/day, 85 ug/kg/day, 80 ug/kg/day, 75 ug/kg/day, 70 ug/kg/day, 65 ug/kg/day, 60 ug/kg/day, 55 ug/kg/day, 50 ug/kg/day, 45 ug/kg/day, 40 ug/kg/day, 35 ug/kg/day, 30 ug/kg/day, 26 ug/kg/day, 25 ug/kg/day, 20 ug/kg/day, 15 ug/kg/day, 13 ug/kg/day, 10 ug/kg/day, 6.5 ug/kg/day, 5 ug/kg/day, 3.2 ug/kg/day, 3 ug/kg/day, 2.5 ug/kg/day, 2 ug/kg/day, 1.6 ug/kg/day, 1.5 ug/kg/day, 1 ug/kg/day, 0.5 ug/kg/day, 0.25 ug/kg/day, 0.1 ug/kg/day, or 0.05 ug/kg/day; and/or wherein the prophylactically effective amount is 1200 ug/m$^2$/day, 1150 ug/m$^2$/day, 1100 ug/m$^2$/day, 1050 ug/m$^2$/day, 1000 ug/m$^2$/day, 950 ug/m$^2$/day, 900 ug/m$^2$/day, 850 ug/m$^2$/day, 800 ug/m$^2$/day, 750 ug/m$^2$/day, 700 ug/m$^2$/day, 650 ug/m$^2$/day, 600 ug/m$^2$/day, 550 ug/m$^2$/day, 500 ug/m$^2$/day, 450 ug/m$^2$/day, 400 ug/m$^2$/day, 350 ug/m$^2$/day, 300 ug/m$^2$/day, 250 ug/m$^2$ day, 200 ug/m$^2$/day, 150 ug/m$^2$/day, 100 ug/m$^2$/day, 50 ug/m$^2$/day, 40 ug/m$^2$ day, 30 ug/m$^2$/day, 20 ug/m$^2$/day, 15 ug/m$^2$/day, 10 ug/m$^2$/day, or 5 ug/m$^2$/day.

In some embodiments, the intravenous dose of 1200 ug/m$^2$ or less, 1150 ug/m$^2$ or less, 1100 ug/m$^2$ or less, 1050 ug/m$^2$ or less, 1000 ug/m$^2$ or less, 950 ug/m$^2$ or less, 900 ug/m$^2$ or less, 850 ug/m$^2$ or less, 800 ug/m$^2$ or less, 750 ug/m$^2$ or less, 700 ug/m$^2$ or less, 650 ug/m$^2$ or less, 600 ug/m$^2$ or less, 550 ug/m$^2$ or less, 500 ug/m$^2$ or less, 450 ug/m$^2$ or less, 400 ug/m$^2$ or less, 350 ug/m$^2$ or less, 300 ug/m$^2$ or less, 250 ug/m$^2$ or less, 200 ug/m$^2$ or less, 150 ug/m$^2$ or less, 100 ug/m$^2$ or less, 50 ug/m$^2$ or less, 40 ug/m$^2$ or less, 30 ug/m$^2$ or less, 20 ug/m$^2$ or less, 15 ug/m$^2$ or less, 10 ug/m$^2$ or less, or 5 ug/m$^2$ or less of the anti-CD3 antibody such as teplizumab is administered over about 24 hours, about 22 hours, about 20 hours, about 18 hours, about 16 hours, about 14 hours, about 12 hours, about 10 hours, about 8 hours, about 6 hours, about 4 hours, about 2 hours, about 1.5 hours, about 1 hour, about 50 minutes, about 40 minutes, about 30 minutes, about 20 minutes, about 10 minutes, about 5 minutes, about 2 minutes, about 1 minute, about 30 seconds or about 10 seconds to prevent, treat or ameliorate one or more symptoms of type 1 diabetes. The total dosage over the duration of the regimen is preferably a total of less than about 14000 ug/m$^2$, 13500 ug/m$^2$, 13000 ug/m$^2$, 12500 ug/m$^2$, 12000 ug/m$^2$, 11500 ug/m$^2$, 11000 ug/m$^2$, 10500 ug/m$^2$, 10000 ug/m$^2$, 9500 ug/m$^2$, 9000 ug/m$^2$, 8000 ug/m$^2$, 7000 ug/m$^2$, 6000 ug/m$^2$, and may be less than 5000 ug/m$^2$, 4000 ug/m$^2$, 3000 ug/m$^2$, 2000 ug/m$^2$, or 1000 ug/m$^2$. In some embodiments, the daily dosage administered in the regimen is from about 100 ug/m$^2$ to about 200 ug/m$^2$, about 100 ug/m$^2$ to about 500 ug/m$^2$, about 100 ug/m$^2$ to about 1000 ug/m$^2$, or about 500 ug/m$^2$ to about 1000 ug/m$^2$.

In some embodiments, the dose escalates over the first three, first 1/4 of the doses (e.g., over the first 3 days of a 12-day regimen of one dose per day) of the treatment regimen until the daily effective amount of the anti-CD3 antibody such as teplizumab is achieved. In some embodiments, a subject is administered a treatment regimen comprising one or more doses of an effective amount of the anti-CD3 antibody such as teplizumab, wherein the effective amount is increased by, e.g., 0.01 ug/kg, 0.02 ug/kg, 0.04 ug/kg, 0.05 ug/kg, 0.06 ug/kg, 0.08 ug/kg, 0.1 ug/kg, 0.2 ug/kg, 0.25 ug/kg, 0.5 ug/kg, 0.75 ug/kg, 1 ug/kg, 1.5 ug/kg, 2 ug/kg, 4 ug/kg, 5 ug/kg, 10 ug/kg, 15 ug/kg, 20 ug/kg, 25 ug/kg, 30 ug/kg, 35 ug/kg, 40 ug/kg, 45 ug/kg, 50 ug/kg, 55 ug/kg, 60 ug/kg, 65 ug/kg, 70 ug/kg, 75 ug/kg, 80 ug/kg, 85 ug/kg, 90 ug/kg, 95 ug/kg, 100 ug/kg, or 125 ug/kg each day; or increased by, e.g., 100 ug/m$^2$, 150 ug/m$^2$, 200 ug/m$^2$, 250 ug/m$^2$, 300 ug/m$^2$, 350 ug/m$^2$, 400 ug/m$^2$, 450 ug/m$^2$, 500 ug/m$^2$, 550 ug/m$^2$, 600 ug/m$^2$, or 650 ug/m$^2$, each day as treatment progresses. In some embodiments, a subject is administered a treatment regimen comprising one or more doses of an effective amount of the anti-CD3 antibody such as teplizumab, wherein the effective amount is increased by a factor of 1.25, a factor of 1.5, a factor of 2, a factor of 2.25, a factor of 2.5, or a factor of 5 until the daily effective amount of the anti-CD3 antibody such as teplizumab is achieved.

In some embodiments, a subject is intramuscularly administered one or more doses of a 200 ug/kg or less, preferably 175 ug/kg or less, 150 ug/kg or less, 125 ug/kg or less, 100 ug/kg or less, 95 ug/kg or less, 90 ug/kg or less, 85 ug/kg or less, 80 ug/kg or less, 75 ug/kg or less, 70 ug/kg or less, 65 ug/kg or less, 60 ug/kg or less, 55 ug/kg or less, 50 ug/kg or less, 45 ug/kg or less, 40 ug/kg or less, 35 ug/kg or less, 30 ug/kg or less, 25 ug/kg or less, 20 ug/kg or less, 15 ug/kg or less, 10 ug/kg or less, 5 ug/kg or less, 2.5 ug/kg or less, 2 ug/kg or less, 1.5 ug/kg or less, 1 ug/kg or less, 0.5 ug/kg or less, or 0.2 ug/kg or less of the anti-CD3 antibody such as teplizumab to treat or ameliorate one or more symptoms of T1D.

In some embodiments, a subject is subcutaneously administered one or more doses of a 200 ug/kg or less, preferably 175 ug/kg or less, 150 ug/kg or less, 125 ug/kg or less, 100 ug/kg or less, 95 ug/kg or less, 90 ug/kg or less, 85 ug/kg or less, 80 ug/kg or less, 75 ug/kg or less, 70 ug/kg or less, 65 ug/kg or less, 60 ug/kg or less, 55 ug/kg or less, 50 ug/kg or less, 45 ug/kg or less, 40 ug/kg or less, 35 ug/kg or less, 30 ug/kg or less, 25 ug/kg or less, 20 ug/kg or less, 15 ug/kg or less, 10 ug/kg or less, 5 ug/kg or less, 2.5 ug/kg or less, 2 ug/kg or less, 1.5 ug/kg or less, 1 ug/kg or less, 0.5 ug/kg or less, or 0.2 ug/kg or less of the anti-CD3 antibody such as teplizumab to treat or ameliorate one or more symptoms of T1D.

In some embodiments, a subject is intravenously administered one or more doses of a 100 ug/kg or less, preferably 95 ug/kg or less, 90 ug/kg or less, 85 ug/kg or less, 80 ug/kg or less, 75 ug/kg or less, 70 ug/kg or less, 65 ug/kg or less, 60 ug/kg or less, 55 ug/kg or less, 50 ug/kg or less, 45 ug/kg or less, 40 ug/kg or less, 35 ug/kg or less, 30 ug/kg or less, 25 ug/kg or less, 20 ug/kg or less, 15 ug/kg or less, 10 ug/kg or less, 5 ug/kg or less, 2.5 ug/kg or less, 2 ug/kg or less, 1.5 ug/kg or less, 1 ug/kg or less, 0.5 ug/kg or less, or 0.2 ug/kg or less of the anti-CD3 antibody such as teplizumab to treat or ameliorate one or more symptoms of T1D. In some embodiments, the intravenous dose of 100 ug/kg or less, 95 ug/kg or less, 90 ug/kg or less, 85 ug/kg or less, 80 ug/kg or less, 75 ug/kg or less, 70 ug/kg or less, 65 ug/kg or less, 60 ug/kg or less, 55 ug/kg or less, 50 ug/kg or less, 45 ug/kg or less, 40 ug/kg or less, 35 ug/kg or less, 30 ug/kg or less, 25 ug/kg or less, 20 ug/kg or less, 15 ug/kg or less, 10 ug/kg or less, 5 ug/kg or less, 2.5 ug/kg or less, 2 ug/kg or less, 1.5 ug/kg or less, 1 ug/kg or less, 0.5 ug/kg or less, or 0.2 ug/kg or less of the anti-CD3 antibody such as teplizumab, is administered over about 6 hours, about 4 hours, about 2 hours, about 1.5 hours, about 1 hour, about 50 minutes, about 40 minutes, about 30 minutes, about 20 minutes, about 10 minutes, about 5 minutes, about 2 minutes, about 1 minute, about 30 seconds or about 10 seconds to treat or ameliorate one or more symptoms of T1D.

In some embodiments, a subject is orally administered one or more doses of a 100 ug/kg or less, preferably 95 ug/kg or less, 90 ug/kg or less, 85 ug/kg or less, 80 ug/kg or less, 75 ug/kg or less, 70 ug/kg or less, 65 ug/kg or less, 60 ug/kg or less, 55 ug/kg or less, 50 ug/kg or less, 45 ug/kg or less, 40 ug/kg or less, 35 ug/kg or less, 30 ug/kg or less, 25 ug/kg or less, 20 ug/kg or less, 15 ug/kg or less, 10 ug/kg or less, 5 ug/kg or less, 2.5 ug/kg or less, 2 ug/kg or less, 1.5 ug/kg or less, 1 ug/kg or less, 0.5 ug/kg or less, or 0.2 ug/kg or less of the anti-CD3 antibody such as teplizumab to treat or ameliorate one or more symptoms of T1D. In some embodiments, the oral dose of 100 ug/kg or less, 95 ug/kg or less, 90 ug/kg or less, 85 ug/kg or less, 80 ug/kg or less, 75 ug/kg or less, 70 ug/kg or less, 65 ug/kg or less, 60 ug/kg or less, 55 ug/kg or less, 50 ug/kg or less, 45 ug/kg or less, 40 ug/kg or less, 35 ug/kg or less, 30 ug/kg or less, 25 ug/kg or less, 20 ug/kg or less, 15 ug/kg or less, 10 ug/kg or less, 5 ug/kg or less, 2.5 ug/kg or less, 2 ug/kg or less, 1.5 ug/kg or less, 1 ug/kg or less, 0.5 ug/kg or less, or 0.2 ug/kg or less of the anti-CD3 antibody such as teplizumab is administered over about 6 hours, about 4 hours, about 2 hours, about 1.5 hours, about 1 hour, about 50 minutes, about 40 minutes, about 30 minutes, about 20 minutes, about 10 minutes, about 5 minutes, about 2 minutes, about 1 minute, about 30 seconds or about 10 seconds to treat or ameliorate one or more symptoms of T1D.

In some embodiments in which escalating doses are administered for the first days of the dosing regimen, the dose on day 1 of the regimen is 100-250 ug/m$^2$/day, preferably 106 ug/m$^2$/day and escalates to the daily dose as recited immediately above by day 2, and 3. For example, on day 1, the subject is administered a dose of approximately 106 ug/m$^2$/day, on day 2 approximately 425 ug/m$^2$/day, and on subsequent days of the regimen (e.g., days 3-12) 850 ug/m$^2$/day. In some embodiments, on day 1, the subject is administered a dose of approximately 211 ug/m$^2$/day, on day 2 approximately 423 ug/m$^2$/day, on day 3 and subsequent days of the regimen (e.g., days 3-12) approximately 840 ug/m$^2$/day.

In some embodiments, to reduce the possibility of cytokine release and other adverse effects, the first 1, 2, or 3 doses or all the doses in the regimen are administered more slowly by intravenous administration. For example, a dose of 106 ug/m$^2$/day may be administered over about 5 minutes, about 15 minutes, about 30 minutes, about 45 minutes, about 1 hour, about 2 hours, about 4 hours, about 6 hours, about 8 hours, about 10 hours, about 12 hours, about 14 hours, about 16 hours, about 18 hours, about 20 hours, and about 22 hours. In some embodiments, the dose is administered by slow infusion over a period of, e.g., 20 to 24 hours. In some embodiments, the dose is infused in a pump, preferably increasing the concentration of antibody administered as the infusion progresses.

In some embodiments, a set fraction of the doses for the 106 ug/m$^2$/day to 850 ug/m$^2$/day regimen described above is administered in escalating doses.

In some embodiments, the anti-CD3 antibody such as teplizumab is not administered by daily doses over a number of days, but is rather administered by infusion in an uninterrupted manner over 4 hours, 6 hours, 8 hours, 10 hours, 12 hours, 15 hours, 18 hours, 20 hours, 24 hours, 30 hours or 36 hours. The infusion may be constant or may start out at a lower dosage for, for example, the first 1, 2, 3, 5, 6, or 8 hours of the infusion and then increase to a higher dosage thereafter. Over the course of the infusion, the patient receives a dose equal to the amount administered in the 5 to 20-day regimens set forth above. For example, a dose of approximately 150 ug/m$^2$, 200 ug/m$^2$, 250 ug/m$^2$, 500 ug/m$^2$, 750 ug/m$^2$, 1000 ug/m$^2$, 1500 ug/m$^2$, 2000 ug/m$^2$, 3000 ug/m$^2$, 4000 ug/m$^2$, 5000 ug/m$^2$, 6000 ug/m$^2$, 7000 ug/m$^2$, 8000 ug/m$^2$, 9000 ug/m$^2$, 9500 ug/m$^2$, 10000 ug/m$^2$, 10500 ug/m$^2$, 11000 ug/m$^2$, 11500 ug/m$^2$, 12000 ug/m$^2$, 12500 ug/m$^2$, 13000 ug/m$^2$, 13500 ug/m$^2$ or 14000 ug/m$^2$ can be administered. In particular, the speed and duration of the infusion is designed to minimize the level of free anti-CD3 antibody such as teplizumab in the subject after administration. In some embodiments, the level of free anti-CD3 antibody such as teplizumab should not exceed 200 ng/ml free antibody. In addition, the infusion is designed to achieve a combined T cell receptor coating and modulation of at least 50%, 60%, 70%, 80%, 90%, 95% or of 100%.

In some embodiments, the anti-CD3 antibody such as teplizumab is administered chronically to treat, or slow the progression, or ameliorate one or more symptoms of type 1 diabetes. For example, in some embodiments, a low dose of the anti-CD3 antibody such as teplizumab is administered once a month, twice a month, three times per month, once a week or even more frequently either as an alternative to the 6 to 14-day dosage regimen discussed above or after administration of such a regimen to enhance or maintain its effect. Such a low dose may be anywhere from 1 ug/m$^2$ to 100 ug/m$^2$, such as approximately 5 ug/m$^2$, 10 ug/m$^2$, 15 ug/m$^2$, 20 ug/m$^2$, 25 ug/m$^2$, 30 ug/m$^2$, 35 ug/m$^2$, 40 ug/m$^2$, 45 ug/m$^2$, or 50 ug/m$^2$.

In some embodiments, the subject may be re-dosed at some time subsequent to administration of the two course anti-CD3 antibody such as teplizumab dosing regimen, for example, based upon one or more physiological or biomarker parameters or may be done as a matter of course. Such redosing may be administered and/or the need for such redosing evaluated 2 months, 4 months, 6 months, 8 months, 9 months, 1 year, 15 months, 18 months, 2 years, 30 months or 3 years after administration of a dosing regimen and may include administering a course of treatment every 6 months, 9 months, 1 year, 15 months, 18 months, 2 years, 30 months or 3 years indefinitely.

In some embodiments, before and/or after (e.g., at 1-6 month interval, or 2-5 month interval, or about 3 month interval) the administration of a 12-day course of teplizumab, the level (or relative amounts) of phenotypically exhausted T cells, such as TIGIT+KLRG1+CD8+CD3+ cells with respect to all CD3+ T cells is determined, for example by flow cytometry. In some embodiments, the level of the TIGIT+KLRG1+CD8+CD3+ T-cells can be monitored for example by flow cytometry. In some embodiments, an additional 12-day course of anti-CD3 antibody, such as teplizumab, is administered when the level of the TIGIT+ KLRG1+CD8+CD3+ T-cells corresponds to (e.g., returns to) the baseline level. In some embodiments, the determining of TIGIT+KLRG1+CD8+CD3+ T-cells is about 3 months (or about 1-6 months) after the administration of the second 12-day course. In some embodiments, if the subject has more than about 10% TIGIT+KLRG1+CD8+ T-cells in all CD3+ T cells, the monitoring can be annual. In some embodiments, if the subject has less than about 10% TIGIT+ KLRG1+CD8+ T-cells in all CD3+ T cells, the monitoring can be every about 3-6 months.

In some embodiments, the re-dosing comprises administering additional (e.g., second, third, or beyond) 12-day course(s) of teplizumab each at a total dose of more than about 9000 µg/m² as described herein. In some embodiments, the additional 12-day course of teplizumab comprises a first dose of 106 µg/m² teplizumab on day 1, a second dose of 425 µg/m² teplizumab on day 2, and one dose of 850 µg/m² on each of days 3-12, and wherein the total dose is approximately 9031 µg/m². In other embodiments the additional 12-day course of teplizumab comprises a first dose of 211 µg/m² teplizumab on day 1, a second dose of 423 µg/m² teplizumab on day 2, and one dose of 840 µg/m² on each of days 3-12, and wherein the total dose is approximately 9034 µg/m².

In some embodiments, the additional (e.g., second, third, or beyond) 12-day course of anti-CD3 antibody, such as teplizumab, can be administered about 12 month to about a 24 month after the administering of the prior 12-day course, for example 12, 13, 14, 15, 16, 17, 19, 20, 21, 22, 23 or 24 months.

In some embodiments, the anti-CD3 antibody such as teplizumab is administered to achieve, or maintain a level of glycosylated hemoglobin (HA1 or HA1c) less than 8%, less than 7.5%, less than 7%, less than 6.5%, less than 6%, less than 5.5% or 5% or less. At the initiation of treatment, patients have a HA1 or HA1c level of less than 8%, less than 7.5%, less than 7%, less than 6.5%, less than 6%, or, more preferably, from 4%-6% (preferably measured in the absence of other treatment for diabetes, such as administration of exogenous insulin). Such patients preferably have retained at least 95%, 90%, 80%, 70%, 60%, 50%, 40% 30% or 20% of beta-cell function prior to initiation of treatment. In some embodiments, the administration of the anti-CD3 antibodies prevents damage, thereby slowing progression of the disease and reducing the need for insulin administration. In some embodiments, the methods of treatment provided herein result in a level of HA1 or HA1c is 7% or less, 6.5% or less, 6% or less, 5.5% or less, or 5% or less 6 months, 9 months, 12 months, 15 months, 18 months, or 24 months after the previous treatment. In some embodiments, the administration of the anti-CD3 antibodies according to the methods provided herein decreases the average level of HA1 or HA1c in the patient by about 5%, about 10%, about 15%, about 20%, about 25%, about 30%, about 35%, about 40%, about 45%, about 50%, about 55%, about 60%, about 65% or about 70% as compared to pre-treatment levels at 6 months, 9 months, 12 months, 15 months, 18 months, or 24 months after the previous treatment. In some embodiments, the administration of the anti-CD3 antibodies according to the methods provided herein results in an average level of HA1 or HA1c in the patient that only increases by about 0.5%, about 1%, about 2.5%, about 5%, about 10%, about 15%, about 20%, about 25%, about 30%, about 35%, about 40%, about 45%, or about 50% as compared to pre-treatment levels at 6 months, 9 months, 12 months, 15 months, 18 months, or 24 months after the previous treatment.

In some embodiments, administration of the anti-CD3 antibodies, in particular teplizumab according to the methods provided herein slows the loss of β cells and/or preserves β cell function (as evidenced by e.g., C-peptide levels, episodes of hypo- or hyper-glycemia, time in range (of glycemia), insulin use, or other assessment method known in the art) over 12 months, 13 months, 14 months, 15 months, 16 months, 17 months, 18 months, 19 months, 20 months, 21 months, 22 months, 2 months, 24 month or more in children and adolescents 8-17 years old who have been diagnosed with T1D in the previous 6 weeks. In some embodiments, administration of the anti-CD3 antibodies, in particular teplizumab according to the methods provided herein slows the loss of β cells and/or preserves β cell function over 18 months (78 weeks) in children and adolescents 8-17 years old who have been diagnosed with T1D in the previous 6 weeks.

Some embodiments relate to Teplizumab for use in a method of treating clinical type 1 diabetes (T1D), comprising administering to a subject in need thereof a 12-day course of the teplizumab at a total dose of more than about 9000 µg/m².

In some embodiments, the total dose is between about 9000 and about 9500 µg/m². In some embodiments, the total dose is between about 9000 and about 14000 µg/m².

In some embodiments, the 12-day course comprises a first dose of 106 µg/m² teplizumab on day 1, a second dose of 425 µg/m² teplizumab on day 2, and one dose of 850 µg/m² on each of days 3-12, and wherein the total dose is approximately 9031 µg/m².

In some embodiments, the 12-day course comprises a first dose of 211 µg/m² teplizumab on day 1, a second dose of 423 µg/m² teplizumab on day 2, and one dose of 840 µg/m² on each of days 3-12, and wherein the total dose is approximately 9034 µg/m².

In some embodiments, the method can include administering a first and a second 12-day courses of teplizumab. In some embodiments, the first and the second 12-day courses are administered at about 1-6 months, about 2-5 months or about 3 months interval.

In some embodiments, the method can include administering to the subject in need thereof a third or more 12-day course of teplizumab, each course at a total dose of more than about 9000 µg/m².

In some embodiments, the third or more 12-day course of teplizumab comprises a first dose of 106 µg/m² teplizumab on day 1, a second dose of 425 µg/m² teplizumab on day 2, and one dose of 850 µg/m² on each of days 3-12, and wherein the total dose of each course is approximately 9031 µg/m².

In some embodiments, the third or more 12-day course of teplizumab comprises a first dose of 211 µg/m² teplizumab on day 1, a second dose of 423 µg/m² teplizumab on day 2, and one dose of 840 µg/m² on each of days 3-12, and wherein the total dose of each course is approximately 9034 µg/m².

In some embodiments, the third or more 12-day course of teplizumab is administered at about a 12 month to about a 24-month interval.

In some embodiments, the method can further include determining, after the administration of each 12-day course, a baseline of a level of TIGIT+KLRG1+CD8+ cells with respect to all CD3+ T cells, monitoring the level of the TIGIT+KLRG1+CD8+CD3+ T-cells and administering an additional 12-day course of teplizumab when the level of the TIGIT+KLRG1+CD8+CD3+ T-cells returns to the baseline level. In some embodiments, the determining of TIGIT+KLRG1+CD8+CD3+ T-cells is by flow cytometry. In some embodiments, the monitoring of TIGIT+KLRG1+CD8+CD3+ T-cells is by flow cytometry. In some embodiments, the determining of TIGIT+KLRG1+CD8+CD3+ T-cells is about 1-6 months, about 2-5 months, or about 3 months after the administration of each 12-day course. In some embodiments, if the subject has more than about 10% TIGIT+KLRG1+CD8+ T-cells in all CD3+ T cells, subsequent monitoring is annual. In some embodiments, if the subject has less than about 10% TIGIT+KLRG1+CD8+ T-cells in all CD8+ T cells, subsequent monitoring is every about 3-6 months.

In some embodiments, the subject in need thereof has been diagnosed with T1D within 6 weeks prior to the administrating step.

In some embodiments, the administrating step results in reduction by at least 10% of insulin use, HbA1c levels, hypoglycemic episodes, or combinations thereof as compared to pre-treatment levels.

In some embodiments, each dose is administered parenterally.

In some embodiments, each dose is administered by intravenous infusion.

In some embodiments, the subject in need thereof is about 8 to 17 years old.

In some embodiments, the subject in need thereof have a peak C-peptide level of ≥0.2 pmol/mL during a mixed meal tolerance test (MMTT).

In some embodiments, the subject receiving teplizumab has a higher mean C-peptide value compared with a control receiving placebo.

In some embodiments, the method further includes assessing the area under the time-concentration curve (AUC) of C-peptide following a mixed meal tolerance test (MMTT), at 78 weeks.

In some embodiments, the subject in need thereof has at least 20% of beta-cell function prior the administration of the first dose.

In some embodiments, the reduction of insulin use, HbA1c levels, hypoglycemic episodes, or combinations thereof is over a period of 12 months or more.

Some aspects relate to a method of treating clinical type 1 diabetes (T1D), comprising administering to a subject in need thereof a 12-day course of teplizumab at a total dose of more than about 9000 μg/m². Some aspects relate to teplizumab for use in a method of treating clinical type 1 diabetes (T1D), comprising administering to a subject in need thereof a 12-day course of the teplizumab at a total dose of more than about 9000 μg/m².

In some embodiments, a method of treating clinical type 1 diabetes (T1D) is provided comprising administering to a subject in need thereof a 12-day course of teplizumab at a total dose of from about 9000 to about 9500 μg/m². In some embodiments, a method of treating clinical type 1 diabetes (T1D) is provided comprising administering to a subject in need thereof a 12-day course of teplizumab at a total dose of from about 9000 to about 14000 μg/m².

EXAMPLES

Example 1. Teplizumab Population Pharmacokinetic Simulations

Introduction

Teplizumab is a 150 kD monoclonal antibody that binds the CD3-8 epitope of the T cell receptor (TCR) complex. The primary mechanism of action of the antibody involves binding the CD3 antigen target on T cells. A population pharmacokinetic (PK) model that describes teplizumab concentrations following IV administration was developed. Teplizumab PK was described by a Quasi-Steady-State (QSS) approximation of the Target-Mediated Drug Disposition (TMDD) model. The aim of this investigation was to use the model to simulate and compare concentration-time profiles of teplizumab following several dosing regimens of interest.

Objectives

The objectives of the analysis were:
To apply the previously developed population PK model to simulate the following three dosing regimens:
  "Herold Dosing Regimen": Day 1:51 μg/m²; Day 2:103 μg/m²; Day 3:207 μg/m²; Day 4:413 μg/m²; Days 5-14:826 μg/m²;
  Regimen 1: Day 1:211 μg/m²; Day 2:423 μg/m²; Days 3-12:840 μg/m²;
  Regimen 2: Day 1:106 μg/m²; Day 2:425 μg/m²; Day 3-12:850 μg/m².
To illustrate and compare concentration-time courses of teplizumab for the 3 dosing regimens listed above.

Subjects and Methods

Dosing Regimens
The Herold regimen is a 14-day course of teplizumab consisting of daily intravenous (IV) infusions (over at least 30 minutes) of 51 μg/m², 103 μg/m², 207 μg/m², and 413 μg/m² on Study Days 1-4, respectively, and an infusion of 826 μg/m² on each of Study Days 5-14. The total dose for a 14-day course is approximately 9034 μg/m². For subjects with body surface area (BSA) of 1.92 m², this dosing schedule delivers approximately 17 mg of teplizumab. The maximum amount of drug delivered at steady-state was designed to provide coating of 50% to 80% of the available CD3 on T cells, with no large excesses of free, unbound drug (projected to be <200 ng/ml at steady-state).

The new Regimen 1 is a 12-day course of teplizumab consisting of daily IV infusion (over at least 30 minutes) of 211 μg/m² and 423 μg/m² on Study Days 1 and 2, respectively, and an infusion of 840 μg/m² on each of Study Days 3-12. The total dose for a 12-day course is approximately 9034 μg/m².

The new Regimen 2 is a 12-day course of teplizumab consisting of daily IV infusion (over at least 30 minutes) of 106 μg/m² and 425 μg/m² on Study Days 1 and 2, respectively, and an infusion of 850 μg/m² on each of Study Days 3-12. The total dose for a 12-day course is approximately 9031 μg/m².

As evident, the same total dose is to be delivered by all three regimens, but in Regimens 1 and 2, delivery is over 12 days rather than 14 days of the original Herold regimen.
Simulations The final model of the previous analysis was used for simulations. Concentration-time courses were simulated for 40 days (Day 0 to Day 40), with 10 time points each day. The model included the study effect as patients from Protégé Encore study were found to have higher clearance and central volume than patients from Protégé study. Therefore, the simulations were conducted separately for these 2 studies. Covariate values of four typical patients were used for simulations, specifically:

Adult patients with no detected anti-drug antibodies [ADA]: 18 years old, 60 kg males with BSA of 1.67 m$^2$;

Adult patients with high level of ADAs: 18 years old, 60 kg males with BSA of 1.67 m$^2$;

Pediatric patients with no detected ADA: 13 years old, 45 kg males with BSA of 1.33 m$^2$;

Pediatric patients with high level of ADAs: 13 years old, 45 kg males with BSA of 1.33 m$^2$.

For each of these patients, population predictions of concentrations over time were computed for each of 3 dosing regimens, and were then compared graphically. Then, the parameters of 1000 similar patients were simulated using the model-estimated inter-individual variability, and individual concentration-time courses were computed using the model. Median and 90% prediction intervals of simulated concentrations at each time point were computed for each regimen, and were compared graphically. In addition, mean and standard deviations of the simulated values at 1 day after the last dose were computed and compared.
Software The simulations were conducted using the NONMEM software, Version 7.4.1 (ICON Development Solutions). Computer resources included personal computers with Intel® processors, Windows 7 Professional or later operating system and Intel® Visual Fortran Professional Compiler (Version 11.0). Graphical and all other statistical analyses, including evaluation of NONMEM outputs were performed using R version 3.4.4 for Windows (R project).

Results

Figures 1A, 1B, 1C, 1D, 1E, 1F:
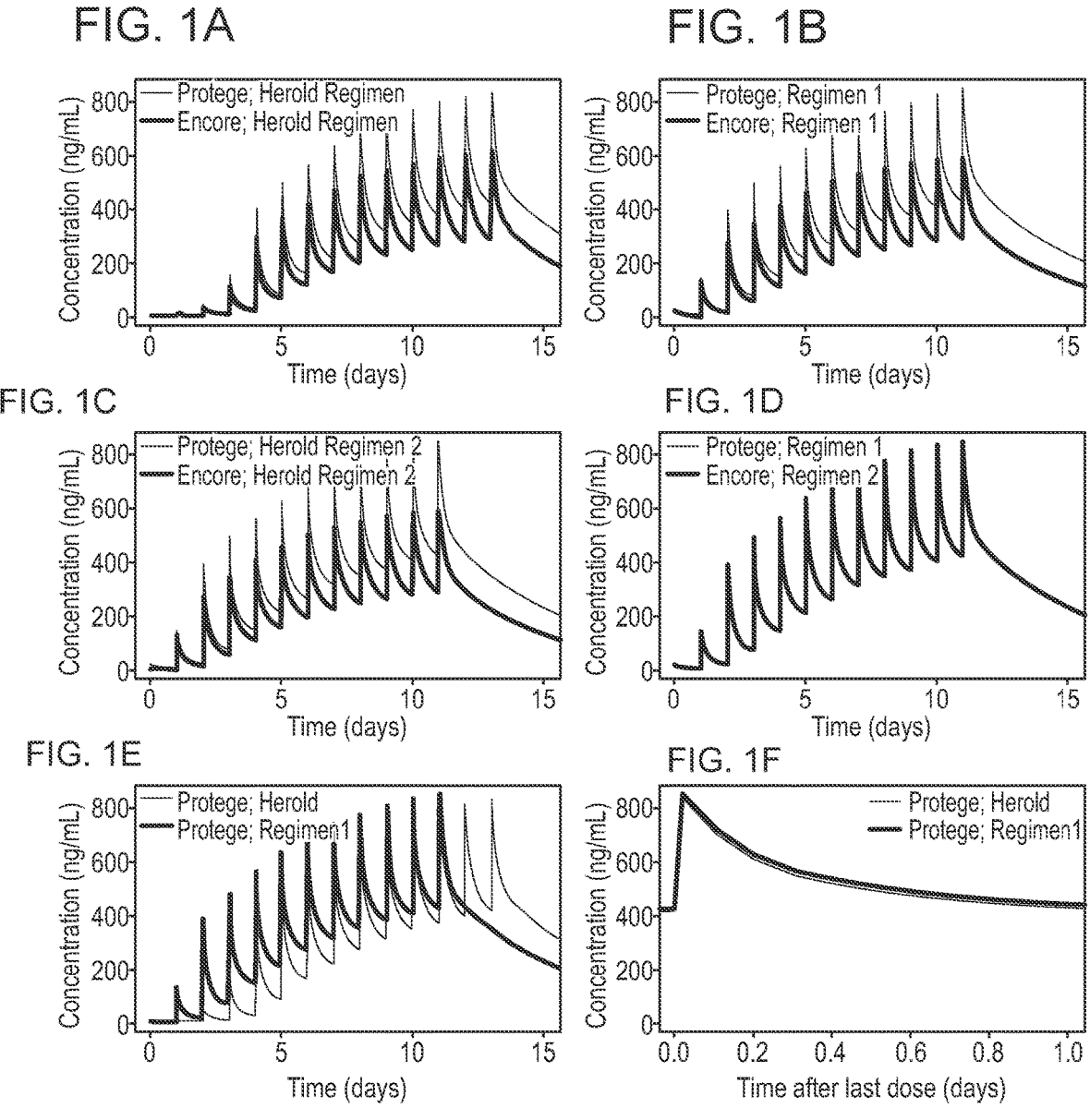
FIGS. 1A-IF are graphs showing Simulated Concentrations versus Time Profiles for Three Dosing Regimens: Population Predictions for a Typical Male Patient with WT=60 kg, Age=18 years, BSA=1.67 m², and no Detected ADAs.
Figure 2:
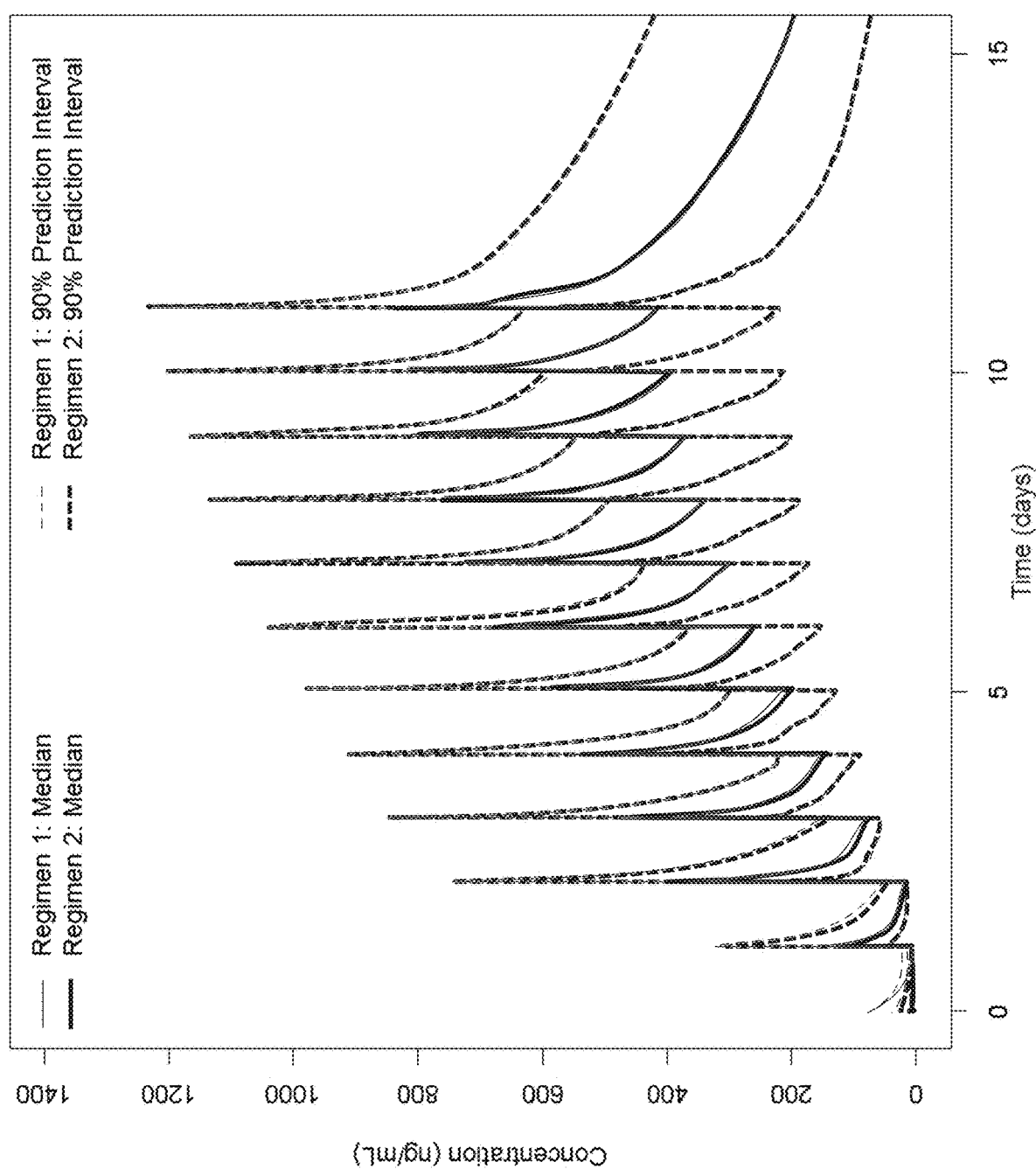
FIG. 2 is a graph showing Comparison of Concentrations versus Time Profiles for Dosing Regimens 1 and 2: Model-based Simulations for a Typical Male Patients with WT=60 kg, Age=18 years, BSA=1.67 m², and no Detected ADAs.
Figure 3:
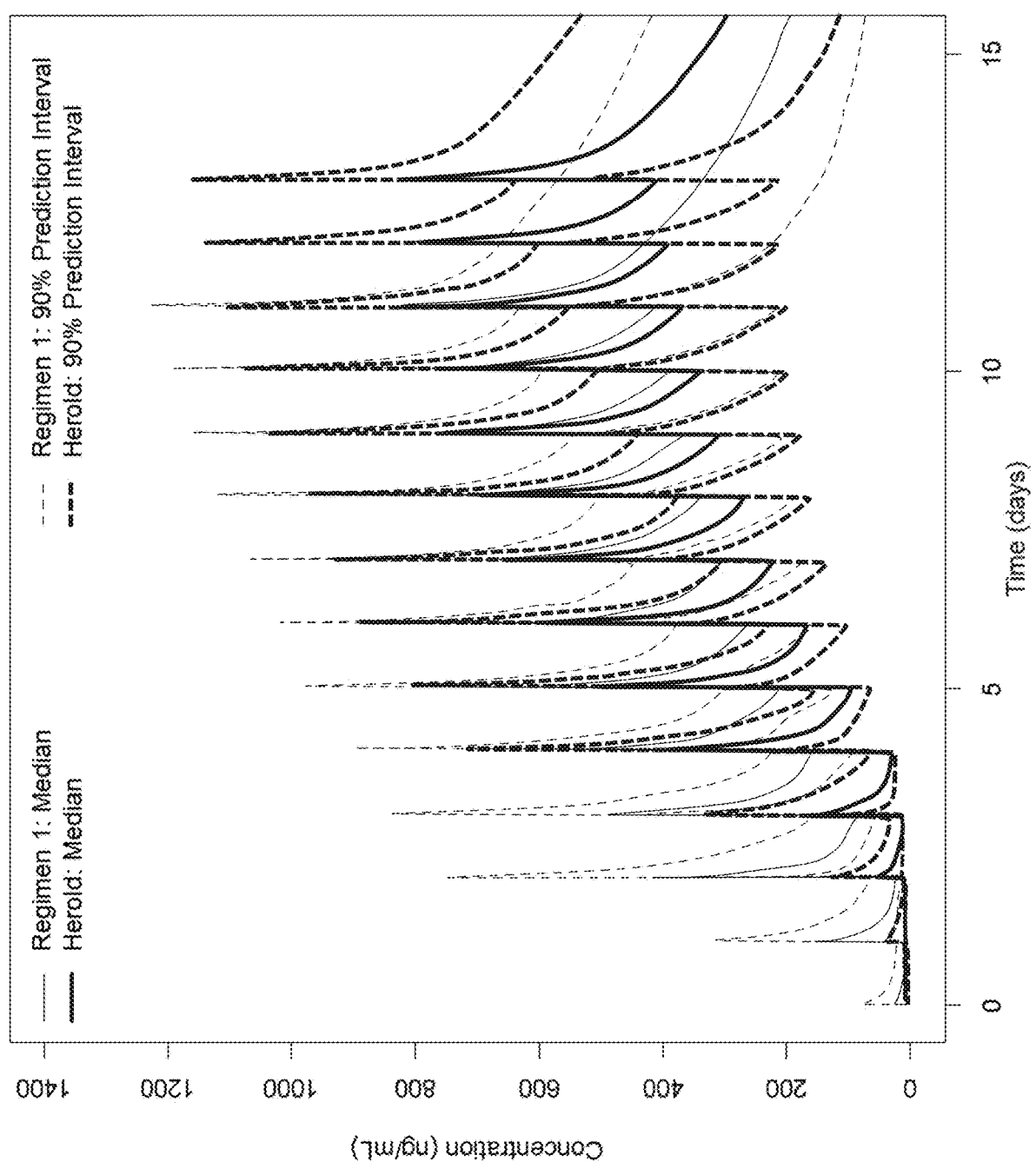
FIG. 3 is a graph showing Comparison of Concentrations versus Time Profiles for Herold Dosing Regimen and Dosing Regimen 1: Model-based Simulations for a Typical Male Patients with WT=60 kg, Age=18 years, BSA=1.67 m², and no Detected ADAs.
Figure 4:
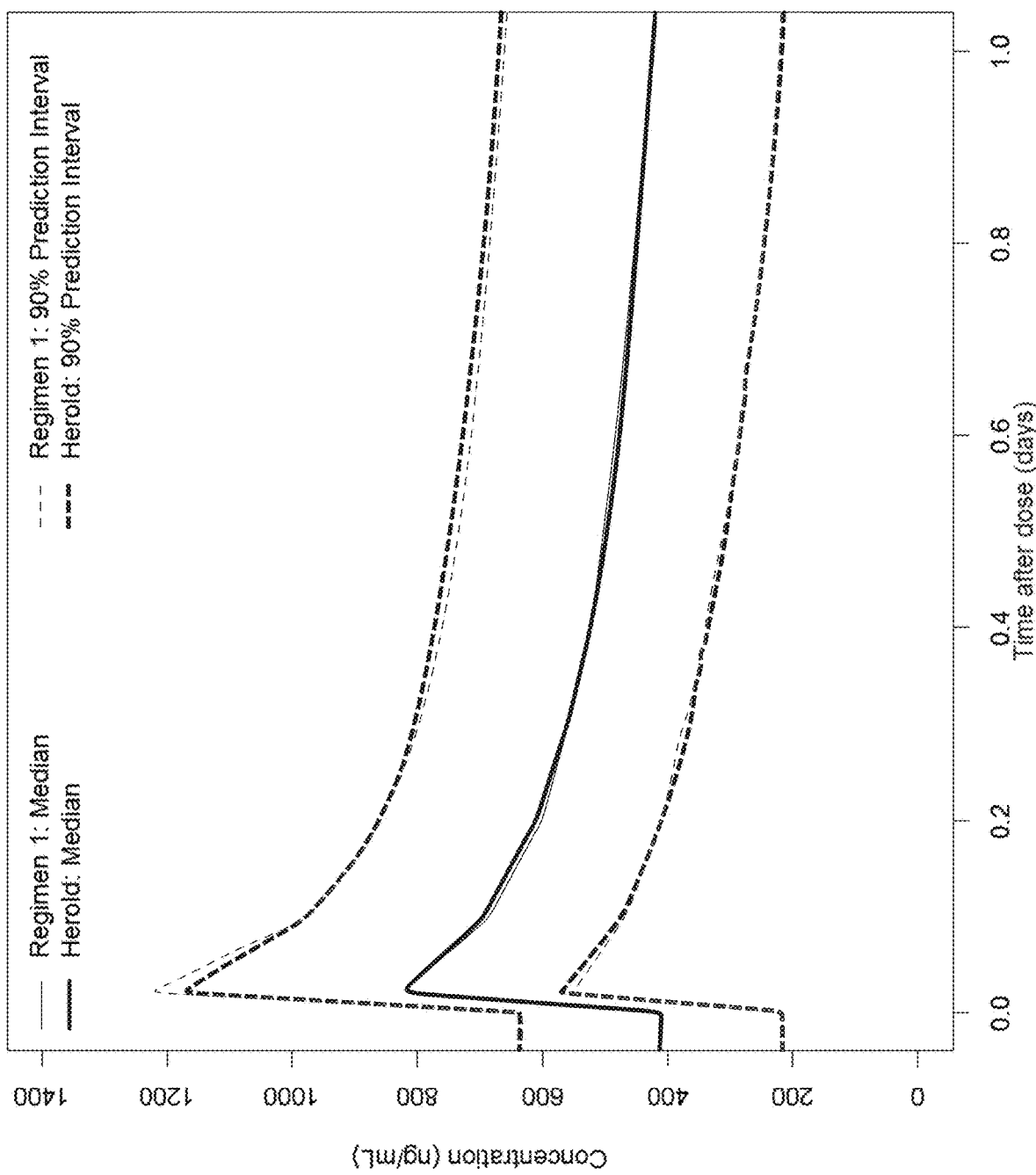
FIG. 4 is a graph showing Comparison of Concentrations versus Time Profiles on the last dosing day for Herold Dosing Regimen and Dosing Regimen 1: Model-based Simulations for a Typical Male Patients with WT=60 kg, Age=18 years, BSA=1.67 m², and no Detected ADAs.
Figures 5A, 5B, 5C, 5D, 5E, 5F:
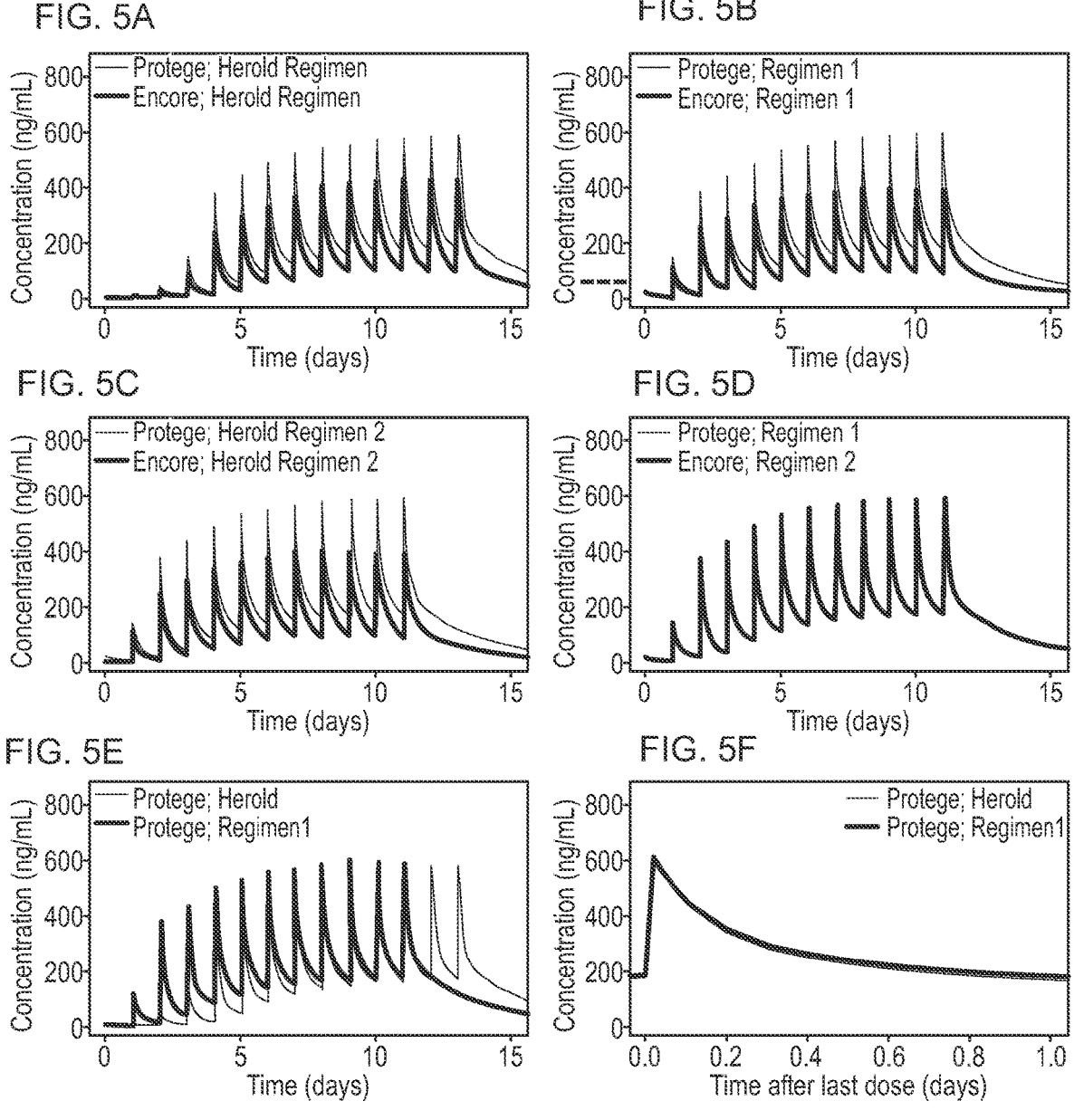
FIGS. 5A-5F are graphs showing Simulated Concentrations versus Time Profiles For Three Dosing Regimens: Population Predictions for a Typical Male Patient with WT=60 kg, Age=18 years, BSA=1.67 m², and High Level of Detected ADAs.
Figure 6:
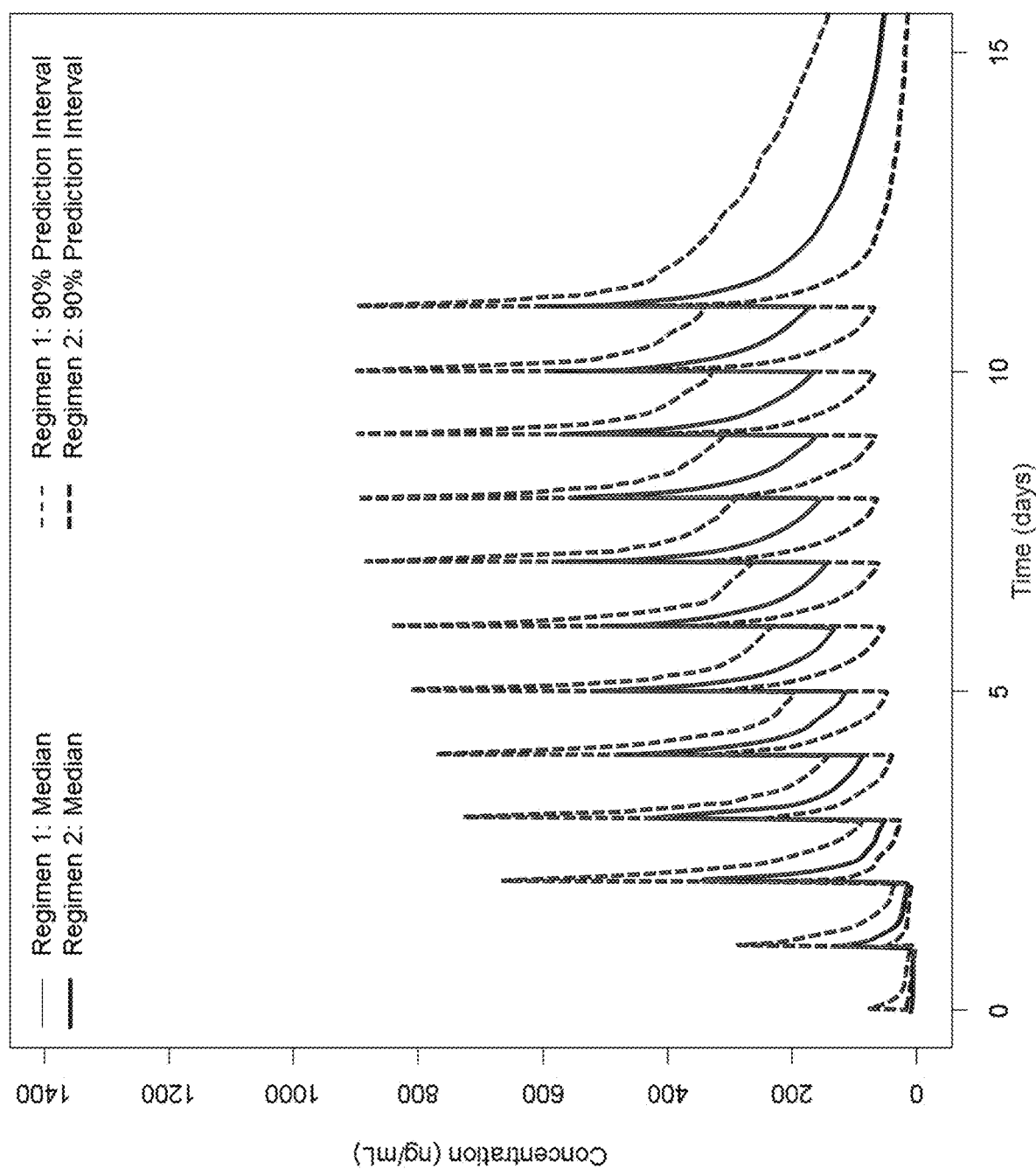
FIG. 6 is a graph showing Comparison of Concentrations versus Time Profiles for Dosing Regimens 1 and 2: Model-based Simulations for Typical Male Patient with WT=60 kg, Age=18 years, BSA=1.67 m², and High Level of Detected ADAs.
Figure 7:
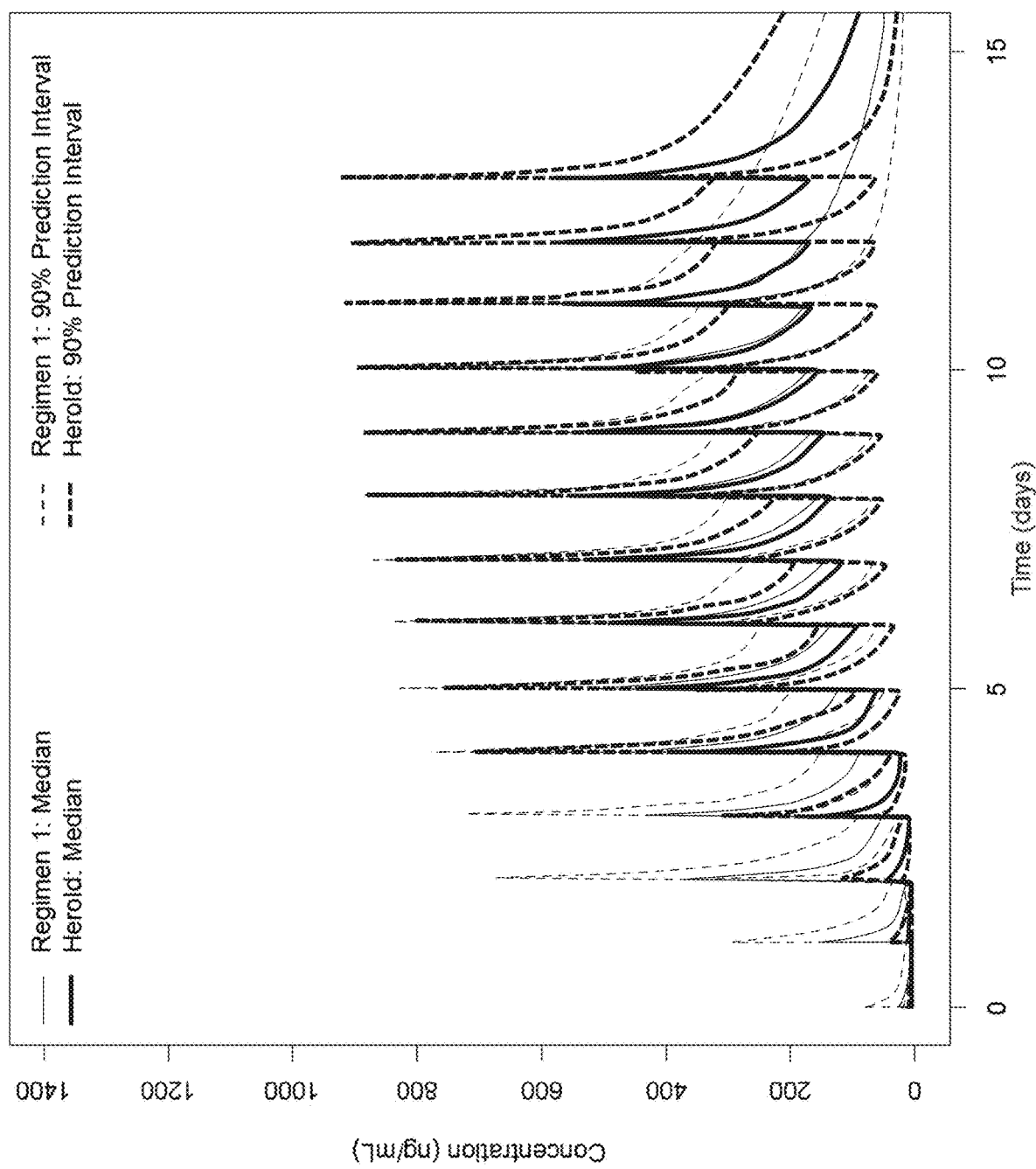
FIG. 7 is a graph showing Comparison of Concentrations versus Time Profiles for Herold Dosing Regimen and Dosing Regimen 1: Model-based Simulations for Typical Male Patients with WT=60 kg, Age=18 years, BSA=1.67 m², and High Level of Detected ADAs.
Figure 8:
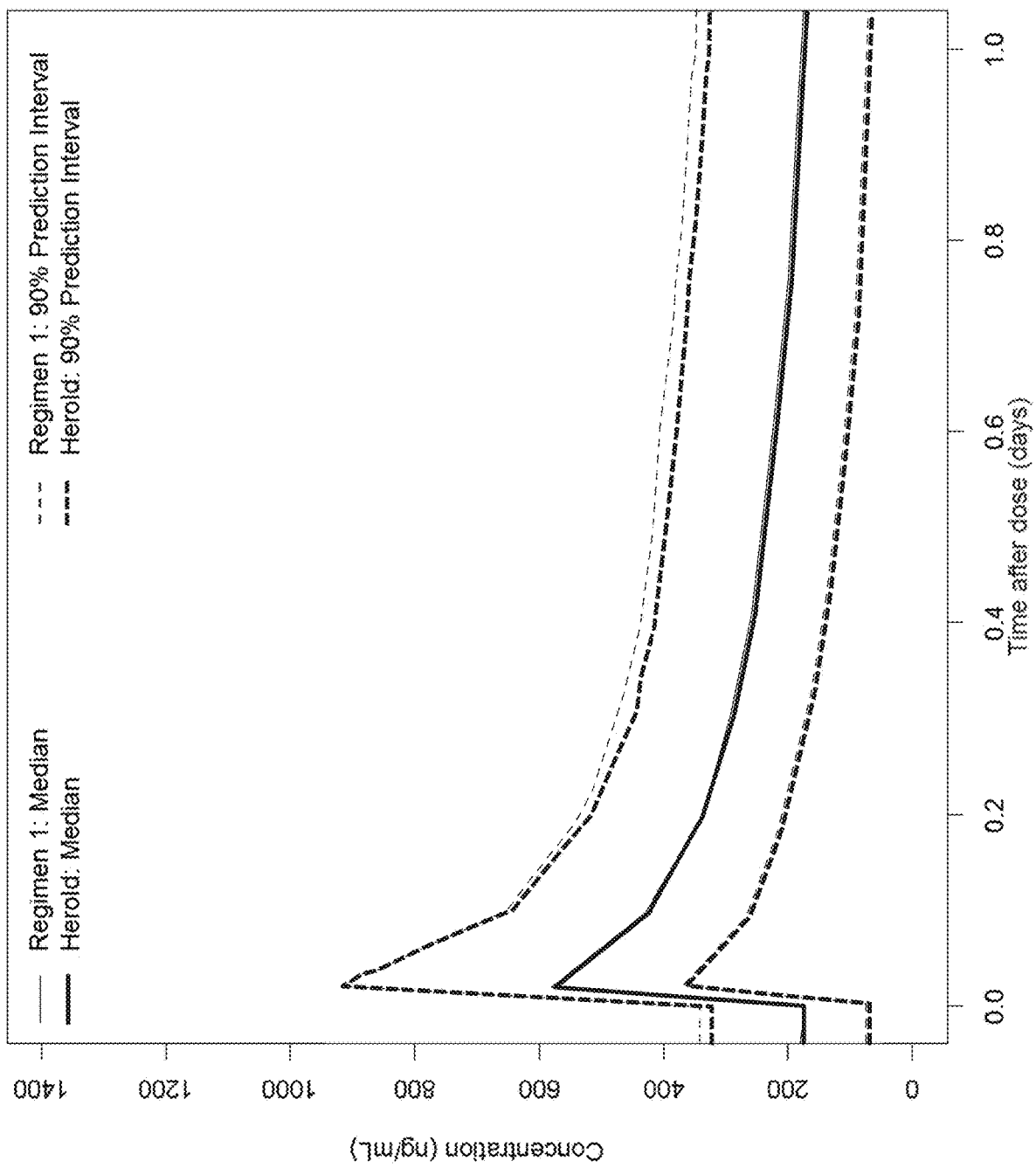
FIG. 8 is a graph showing Comparison of Concentrations versus Time Profiles on the last dosing day for Herold Dosing Regimen and Dosing Regimen 1: Model-based Simulations for Typical Male Patients with WT=60 kg, Age=18 years, BSA=1.67 m², and High Level of Detected ADAs.
Figures 9A, 9B, 9C, 9D, 9E, 9F:
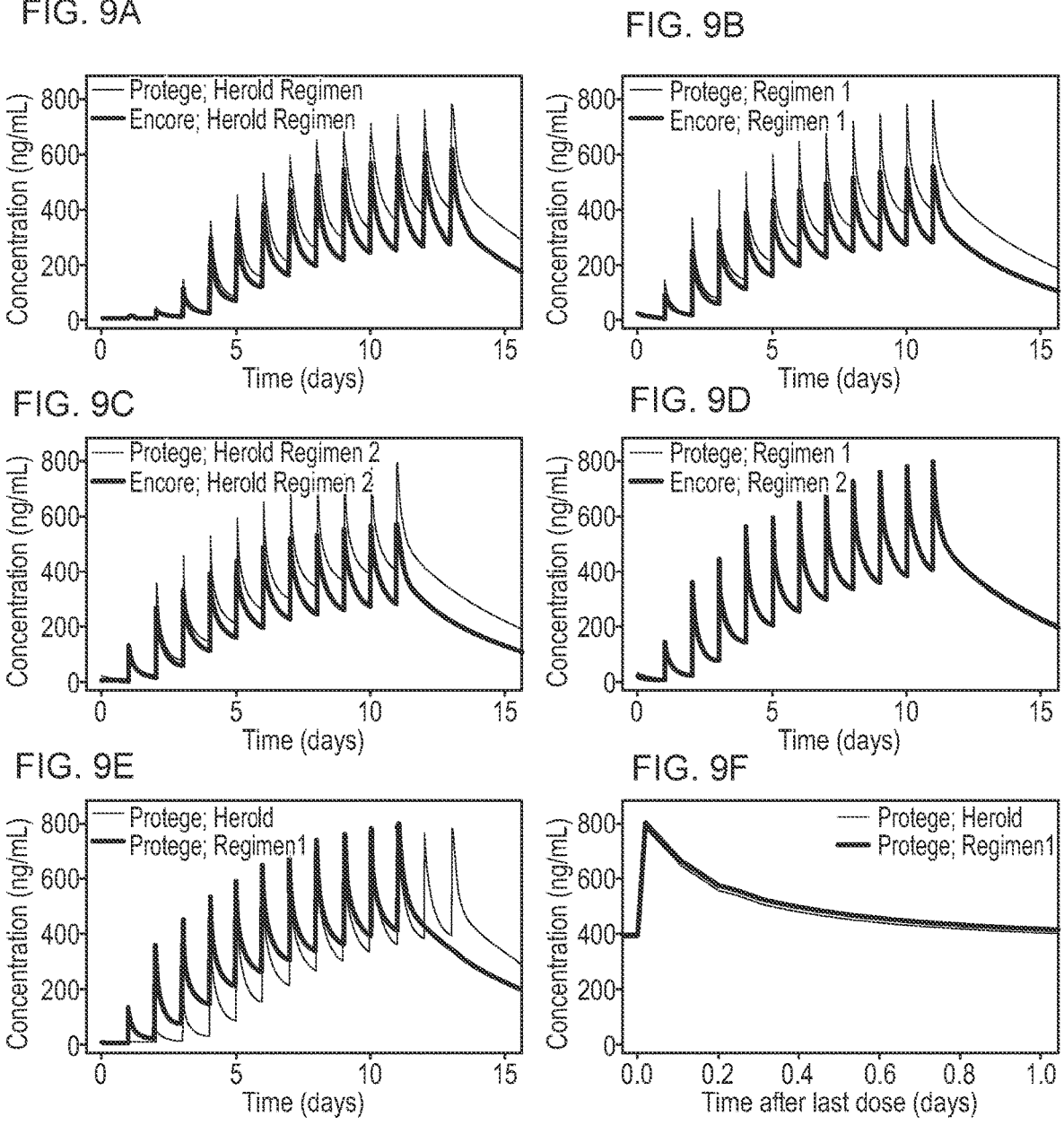
FIGS. 9A-9F are graphs showing Simulated Concentrations versus Time Profiles For Three Dosing Regimens: Population Predictions for a Typical Male Patient with WT=45 kg, Age=13 years, BSA=1.33 m², and no Detected ADAs.
Figure 10:
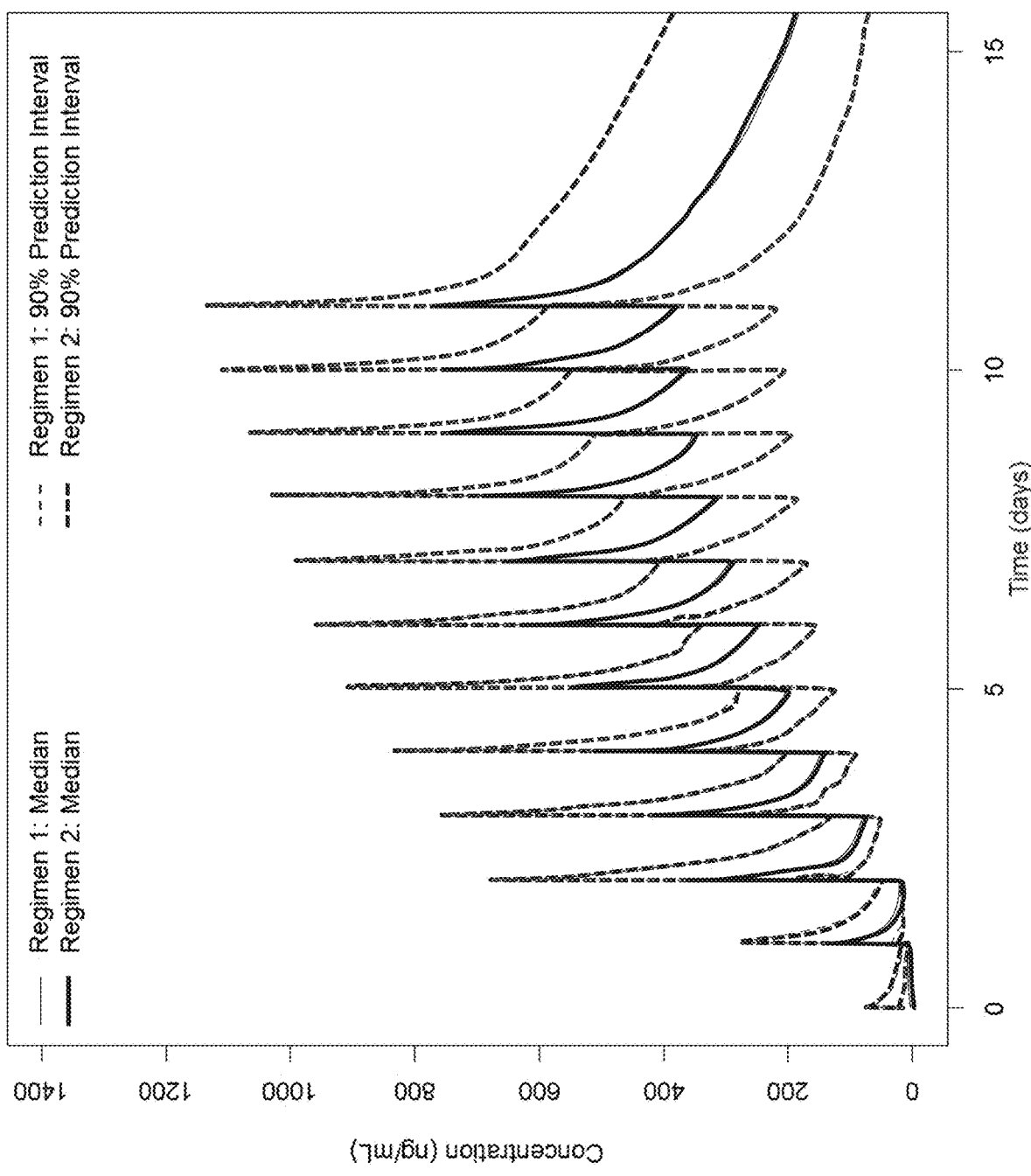
FIG. 10 is a graph showing Comparison of Concentrations versus Time Profiles for Dosing Regimens 1 and 2.

The results of the simulations for typical adult patients with no detected ADAs are shown in FIGS. 1A-1F. Concentrations in the Protégé study were predicted to be higher than in the Encore study for all dosing regimens. The concentrations in Dosing Regimens 1 and 2 were nearly indistinguishable except for minor differences during the first two days of dosing. During the first 12 days of dosing, concentrations in the Herold dosing regimen were lower compared to Dosing regimens 1 and 2, but they were nearly identical following the last dose (on Day 14 for the Herold regimen, and Day 12 for Regimens 1 and 2). The simulations that included inter-individual variability (FIGS. 2-4, Table 1) confirmed these observations. Table 1 illustrates mean and standard deviation of predicted concentrations (ng/mL) over 1000 simulated subjects from Protégé study

TABLE 1

Teplizumab Concentration Predictions: $C_{trough}$ 1 day After the Last Dose

| Patient Population | Dosing Regimen | Time Point | Mean (standard deviation) | |
| --- | --- | --- | --- | --- |
| | | | Excludes residual error | Includes residual error |
| Age = 18 years, WT = | Herold regimen | 14 days | 425 (130) | 426 (220) |
| 60 kg, BSA = 1.67 m$^2$ male | Regimen 1 | 12 days | 432 (133) | 432 (224) |
| subjects with no ADA | Regimen 2 | 12 days | 435 (134) | 435 (225) |
| detected | | | | |
| Age = 18 years, WT = | Herold regimen | 14 days | 184 (82) | 183 (113) |
| 60 kg, BSA = 1.67 m$^2$ male | Regimen 1 | 12 days | 189 (84) | 197 (123) |
| subjects with extremely | Regimen 2 | 12 days | 191 (85) | 199 (124) |
| high ADA levels | | | | |
| (HAHA2 = 10) | | | | |
| Age = 13 years, WT = | Herold regimen | 14 days | 394 (120) | 393 (206) |
| 45 kg, BSA = 1.33 m$^2$ male | Regimen 1 | 12 days | 410 (123) | 403 (210) |
| subjects with no ADA | Regimen 2 | 12 days | 413 (123) | 406 (211) |
| detected | | | | |
| Age = 13 years, WT = | Herold regimen | 14 days | 171 (79) | 174 (112) |
| 45 kg, BSA = 1.33 m$^2$ male | Regimen 1 | 12 days | 173 (77) | 173 (107) |
| subjects with extremely | Regimen 2 | 12 days | 175 (78) | 175 (108) |
| high ADA levels | | | | |
| (HAHA2 = 10) | | | | |

The results of the simulations for typical adult patients with high level of detected ADAs are shown in FIGS. 5A-8. As expected, overall teplizumab levels are much lower for subjects with very high immunogenic response, but the conclusions about differences between the three investigated dosing regimens still hold.

The results of the simulations for typical pediatric patients are shown in FIGS. 9-16. They are very similar to those for adult patients, indicating the BSA-proportional dosing provides similar exposure for pediatric and adult populations.

FIGS. 17-24 show concentration profiles comparing Herold Regimen and Regimen 2 for a longer time period and Table 2-Table 3 summarized Cmax and AUC from 0 to 42 days in the simulations. Figures show that by day 42 concentrations are very low, so values for $AUC_{0-42}$ are essentially the same as for AUCinfinity. Table 2 illustrates mean and standard deviation of predicted maximum concentrations (ng/ml) over 1000 simulated subjects using Protégé Model 205. Table 3 illustrates mean and standard deviation of predicted AUC from 0 to 42 days (ng/mL*day) over 1000 simulated subjects using Protégé Model 205

TABLE 2

Teplizumab Concentration Predictions: $C_{max}$

| Patient Population | Dosing Regimen | Mean (standard deviation) | |
| --- | --- | --- | --- |
| | | Excludes residual error | Includes residual error |
| Age = 18 years, WT = 60 kg, BSA = 1.67 m² male subjects with no ADA detected | Herold regimen | 849 (205) | 850 (405) |
| | Regimen 1 | 855 (200) | 856 (399) |
| | Regimen 2 | 863 (202) | 864 (402) |
| Age = 18 years, WT = 60 kg, BSA = 1.67 m² male subjects with extremely high ADA levels (HAHA2 = 10) | Herold regimen | 609 (178) | 612 (304) |
| | Regimen 1 | 607 (175) | 610 (318) |
| | Regimen 2 | 614 (177) | 617 (321) |
| Age = 13 years, WT = 45 kg, BSA = 1.33 m² male subjects with no ADA detected | Herold regimen | 788 (189) | 785 (377) |
| | Regimen 1 | 792 (199) | 798 (386) |
| | Regimen 2 | 799 (200) | 806 (389) |
| Age = 13 years, WT = 45 kg, BSA = 1.33 m² male subjects with extremely high ADA levels (HAHA2 = 10) | Herold regimen | 559 (159) | 566 (292) |
| | Regimen 1 | 561 (151) | 552 (271) |
| | Regimen 2 | 568 (153) | 558 (274) |

TABLE 3

Teplizumab Concentration Predictions: $AUC_{0-42}$

| Patient Population | Dosing Regimen | $AUC_{0-42}$ Mean (standard deviation) |
| --- | --- | --- |
| Age = 18 years, WT = 60 kg, BSA = 1.67 m² male subjects with no ADA detected | Herold regimen | 6548 (819) |
| | Regimen 1 | 6662 (2085) |
| | Regimen 2 | 6659 (2084) |
| Age = 18 years, WT = 60 kg, BSA = 1.67 m² male subjects with extremely high ADA levels (HAHA2 = 10) | Herold regimen | 3082 (630) |
| | Regimen 1 | 3099 (1044) |
| | Regimen 2 | 3098 (1044) |
| Age = 13 years, WT = 45 kg, BSA = 1.33 m² male subjects with no ADA detected | Herold regimen | 5939 (750) |
| | Regimen 1 | 6032 (1936) |
| | Regimen 2 | 6029 (1935) |

TABLE 3-continued

Teplizumab Concentration Predictions: $AUC_{0-42}$

| Patient Population | Dosing Regimen | $AUC_{0-42}$ Mean (standard deviation) |
| --- | --- | --- |
| Age = 13 years, WT = 45 kg, BSA = 1.33 m² male subjects with extremely high ADA levels (HAHA2 = 10) | Herold regimen | 2830 (557) |
| | Regimen 1 | 2837 (902) |
| | Regimen 2 | 2836 (902) |

Conclusions

The simulations indicated that:

Predicted concentrations of teplizumab are nearly identical for 2 suggested dosing regimens (Regimen 1 and Regimen 2) except for the first day of dosing;

Predicted concentrations of teplizumab increase faster during dosing for Regimens 1 and 2 compared to Herold regimen, but they are nearly identical for all regimens at the last day of dosing;

Predicted concentrations of teplizumab at 1 day after the last dose are nearly identical for all 3 regimens;

BSA-proportional dosing provides homogeneous exposure levels for adult and pediatric subjects with different body size measures.

Example 2. A Phase 3, Randomized, Double-Blind, Multinational, Placebo-Controlled Study to Evaluate Efficacy and Safety of Teplizumab (PRV-031), a Humanized, FcR Non-Binding, Anti-CD3 Monoclonal Antibody, in Children and Adolescents with Newly Diagnosed Type 1 Diabetes (T1D)

Teplizumab (also known as PRV-031, hOKT3γ1 [Ala-Ala], and MGA031) is a humanized 150-kilodalton monoclonal antibody (mAb) that binds to the CD3-ε epitope of the T cell receptor. Teplizumab was developed when preclinical studies demonstrated that targeting T cells (the cells that are instrumental in initiating and coordinating the autoimmune process responsible for type 1 diabetes [T1D] mellitus) via this mechanism altered diabetes immunopathogenesis and prevented and reversed disease in relevant animal models. The goal of this study is to evaluate teplizumab in children and adolescents very recently diagnosed with T1D. Teplizumab holds the promise to be the first disease modifying therapy available to improve both the medical management and overall outlook in those who suffer the most devastating short- and long-term consequences of this disease.

Hypothesis

The hypothesis of this study is that teplizumab is safe, well-tolerated, and effective in slowing the loss of β cells and maintaining a clinically relevant level of β cell function in children and adolescents newly diagnosed with T1D while improving key aspects of T1D clinical management over an 18-month period.

Objectives

The primary objective is:

To determine whether two courses of teplizumab administered 6 months apart slow the loss of β cells and preserve β cell function over 18 months (78 weeks) in children and adolescents 8-17 years old who have been diagnosed with T1D in the previous 6 weeks.

The secondary objectives are:

To evaluate participant improvements in key clinical parameters of diabetes management, including insulin use, glycemic control (including hemoglobin A1c [HbA1c] and time in glycemic target range [T1R]), and clinically important hypoglycemic episodes.

To determine the safety and tolerability of two courses of teplizumab, administered intravenously (IV) 6 months apart To evaluate the pharmacokinetics (PK) and immunogenicity of two courses of IV teplizumab The exploratory objectives are:

To assess β cell function and T1D-focused clinical parameters.

To evaluate immunologic, endocrinologic, molecular, and genetic markers

Endpoints

1. The Primary Endpoint is:

The area under the time-concentration curve (AUC) of C-peptide after a 4-hour (4 h) mixed meal tolerance test (MMTT), a measure of endogenous insulin production and β cell function, at Week 78.

2. The Secondary Endpoints are as Follows:

A. Key Clinical Endpoints:

Exogenous insulin use: defined as a daily average in units per kilogram per day (U/kg/d), at Week 78

HbA1c levels: expressed in % and mmol/mol, at Week 78

T1R: expressed as a daily average of the percentage of time in a 24-hour day a participant's blood glucose (BG) is >70 but ≤180 mg/dl (>3.9 to ≤10.0 mmol/L), assessed using continuous glucose monitoring (CGM), at Week 78

Clinically important hypoglycemic episodes: defined as the total number of episodes of a BG reading of <54 mg/dL (3.0 mmol/L) and/or episodes of severe cognitive impairment requiring external assistance for recovery, from randomization through Week 78

B. Safety Endpoints:

Incidence of treatment-emergent adverse events (TEAEs), adverse events of special interest (AESIs), and serious adverse events (SAEs)

Incidence of treatment-emergent infections of special interest, including but not limited to tuberculosis, an infection requiring IV antimicrobial treatment or hospitalization, Epstein-Barr virus (EBV) and cytomegalovirus (CMV) infection, or significant viremia (ie, DNA-based polymerase chain reaction viral load >10,000 copies per mL or $10^6$ cells), and herpes zoster Incidence and severity of immediate or delayed study drug infusion-related reactions, such as hypersensitivity reactions, pain requiring interruption or discontinuation of infusions, cytokine release syndrome, and serum sickness C. PK and Immunogenicity Endpoints:

Teplizumab serum concentrations

Incidence and titers of anti-teplizumab antibodies after treatment courses

3. The Exploratory Endpoints are as Follows:

A. Assessments of β Cell Function and Health Throughout the Study:

4 h MMTT C-peptide AUC.

Participants with the recognized clinically significant stimulated peak C-peptide of ≥0.2 pmol/mL during 4 h and 2-hour (2 h) MMTTs Proinsulin-to-C-peptide ratios, a measure of β cell endoplasmic reticulum stress and dysfunction B. T1D-Focused Clinical Endpoints During the Study Unless Otherwise Noted:

Exogenous insulin use (in U/kg/day).

HbA1c levels

Participants with poor glycemic control, defined as HbA1c of ≥9%

The number of participants who do not require exogenous insulin because they are able to achieve local, regional, or national age-based glycemic management goals for HbA1c and/or routine blood glucose levels Evaluations of glycemic control based on BG values obtained from intermittent (ie, spot-check, fingerstick) glucometer readings Evaluations of glycemic control based on BG values obtained from CGM readings, including but not limited to T1R; time in hyperglycemia and hypoglycemia ranges; daily, daytime, and nighttime average BG levels and estimated HbA1c; and glycemic variability Clinically important hypoglycemic episodes from randomization through Week 39 and from Week 39 through Week 78

Incidence of "typical" hypoglycemia, defined as BG levels ≥54 mg/dl (3.0 mmol/L) but <70 mg/dL (3.9 mmol/L) and/or non-severe clinical episodes Incidence of diabetic ketoacidosis (DKA) requiring medical attention, defined as a hyperglycemic episode with serum or urine ketones elevated beyond upper limit of normal (ULN) along with serum bicarbonate <15 mmol/L or blood pH<7.3, or both, and resulting in outpatient, emergency room visit or hospitalization Patient-reported outcomes measured by instruments, such as Quality of Life Inventory™ (PedsQL) Diabetes Module, the Hypoglycemia Fear Scale (HFS), and the Diabetes Treatment Satisfaction Questionnaire (DTSQ)

Impact on family life, measured by the parent-reported PedsQL Family Impact questionnaire C. Composite Clinical Endpoints:

Participants with both HbA1c in the American Diabetic Association (ADA) target range (ie, <7.5%) and exogenous insulin dose in specific ranges (<0.25, 0.25 to <0.50, 0.50 to <0.75, 0.75 to <1.0, 1.0 to <1.25, and ≥1.25 U/k/d)

Participants with both HbA1c of <6.5% and <7.0% and exogenous insulin dose of <0.5 U/kg/day or 0.25 U/kg/day D. Other Endpoints During the Study:

Number, type, and titer of T1D autoantibodies

Association of human leukocyte antigen (HLA) type with clinical, metabolic and immune assessments Overview of Study Design This is a Phase 3, randomized, double-blind, placebo-controlled, multinational, multicenter study. Approximately 300 participants are enrolled and randomly assigned at a ratio of 2:1 to either the teplizumab group (N=200) or the placebo group (N=100).

To minimize bias in treatment assignment, potential confounders, and enhance the validity of statistical analysis, participants are randomized at a 2:1 ratio using randomly permuted blocks and stratification based on the following criteria:

Peak C-peptide level at screening: within the range of 0.2 (inclusion criterion) to 0.7 pmol/mL (inclusive) versus >0.7 pmol/mL Age at randomization: within the range of 8 to 12 years (inclusive) versus >12 to 17 years Teplizumab or matching placebo are administered via IV infusion in two courses, with the first course starting on Day 1 (Week 1) and the second course approximately 6 months later at Day 182 (Week 26). Each course of treatment include daily infusions for 12 days.

The total study duration for each participant is up to 84 weeks. This includes a screening period of up to 6 weeks and a post-randomization period of 78 weeks. The treatment period includes two 12-day treatment courses separated by 6 months and a post-treatment observation period of approximately 52 weeks.

Study Population

This study enrolls male and female participants 8 to 17 years of age with new-onset T1D who are able to be randomized and initiate study treatment within 6 weeks of their diagnosis. To be eligible for randomization, participants must be positive for at least one T1D-associated autoantibody and have a peak stimulated C-peptide of ≥0.2 pmol/mL at screening. They must also meet all of the specific inclusion criteria and none of the exclusion criteria.

Dosage and Administration

On the day of randomization (Day 1), each participant receives the first dose of the study drug in the first 12-day treatment course, as shown in the table below. On approximately Day 182, each participant receives the first dose of the second 12-day course. The study drugs (teplizumab or placebo) are administered via IV infusion at the study site or other qualified facility by study-approved personnel. The doses of study drug is calculated based on the participant's body surface area (BSA) measured on the first day of each treatment course. No dose adjustment is permitted.

TABLE 4

| Treatment name | Teplizumab | Placebo |
| --- | --- | --- |
| Description | Sterile solution for injection | Sterile solution for injection |
| Doses in each course | Day 1: 106 µg/m$^2$<br>Day 2: 425 µg/m$^2$<br>Days 3-12: 850 µg/m$^2$<br>Total per course: 9.0 mg/m$^2$ | Matching volumes to active drug |
| Frequency | Two courses starting at Week 1 and Week 26 | Two courses starting at Week 1 and Week 26 |
| Delivery method | IV infusion | IV infusion |

Key Evaluations

MMTT: In order to quantitate endogenous β cell function, participants undergo standardized provocative metabolic testing for C-peptide (a 1:1 by-product of insulin production). Participants consume a fixed amount of a beverage with known amounts of carbohydrates, fats, and protein. Following consumption, BG, insulin, and C-peptide levels are measured over time. A 2 h MMTT is conducted at screening, and 4 h MMTTs is conducted at randomization and Weeks 26, 52, and 78 for key endpoint assessments.

HbA1c: This is the percent of red blood cells (measured as hemoglobin) that has become non-enzymatic glycated proportional to blood glucose levels. This indicates, on average, approximately a 3-month average of blood glucose values. It is a key clinical target in the management of T1D.

Insulin use: As an average over 7 days of data collected before each specified visit to quantify exogenously injected insulin.

Hypoglycemia: Clinically important and potentially life-threating hypoglycemia is the result of insulin therapy and more likely to occur in patients who are attempting to achieve glycemic control goals. This study ask participants to record information regarding BG levels of <70 mg/dL (3.9 mmol/L) and/or events that are consistent with hypoglycemia. A particular focus is on clinically significant hypoglycemic events that are defined as a reliable glucose reading of <54 mg/dL (3.0 mmol/L) and/or severe cognitive impairment and/or physical status requiring external assistance for recovery.

Glucose Monitoring: Intermittent glucose monitoring (e.g, spot-check or fingerstick) performed by participants or caregivers multiple times a day as a necessary part of glycemic management to gauge insulin dosing and assist in diet and activity. All participants are to bring in their glucometers at all visits for review. In addition to data regarding glycemic control, at specified times during the study, participants report their daily before-meal and before-bedtime BG readings and have glucose levels assessed for 2-week intervals using CGM.

Quality of Life Questionnaires: Surveys is used to assess the general health and wellbeing of participants and the effects of teplizumab, such as the PedsQL Diabetes Module, HFS, DTSQ, and parent-reported PedsQL Family Impact Module.

Pharmacokinetic and Immunogenicity Evaluations: Teplizumab concentrations are analyzed in blood samples collected at specified time points throughout the study. Anti-teplizumab antibodies are determined, including those that are neutralizing antibodies (NAbs).

A diagram of the study design is provided in FIG. 25.

The study focuses on individuals who have a significant amount of β cell functional capacity. It is recognized that β cells continue to be lost following T1D diagnosis. To maximize the effect of β cell preservation in patients with a recoverable level endogenous insulin production, this study recruits participants within 6 weeks from T1D diagnosis and a peak C-peptide level of ≥0.2 pmol/mL during a mixed meal tolerance test (MMTT). The value of 0.2 pmol/mL was chosen as it is a key and accepted threshold of C-peptide correlated with clinically important lower rates of T1D-associated short- and long-term complications (Lachin 2014, Palmer 2001, Palmer 2009).

The total study duration for each participant is up to 84 weeks. This includes a screening period of up to 6 weeks and a post-randomization period of 78 weeks. The post-randomization period includes two 12-day treatment courses separated by 6 months and a post-treatment observation period of approximately 52 weeks. The final visit takes place at Week 78.

The overall study length and timepoints for key assessments were chosen due to the natural course of remaining β cell loss following the diagnosis of T1D and study goals to demonstrate durability of effect and to confirm post-treatment safety profiles of teplizumab. At the time of diagnosis there can be substantial β cell reserves, often estimated at 10-20% but in some cases over 40% of normal β cell mass (Matveyenko 2008, Campbell-Thompson 2016). At T1D diagnosis, the majority of this reserve appears to be functionally impaired due to metabolic or immunologic (i.e, cytokine induced) stress. With exogenous insulin treatment and correction of pH, electrolyte and fluid disturbances (ie, DKA) that are often present at diagnosis, some β cell function may return for days, weeks or many months. This observation is often referred to as the "Honeymoon period" where insulin requirements can be substantially reduced and at times independence from exogenous insulin can be achieved. These effects are transient and over time, usually within a year from diagnosis, inevitably full insulin replacement is required due to autoimmune elimination of these remaining β cells. Due to the known individual variability in the natural history of β cell loss, the effect of disease modifying therapies intended to preserve β cell function is difficult to distinguish from the Honeymoon period effects during the first 12 months of T1D diagnosis.

The 18-month time point for the primary and key secondary clinical endpoints provide key data needed for the acceptance of teplizumab as a T1D disease modifying therapy into regular medical practice and is consistent with existing guidelines for endpoints recommended by the EMA and FDA. Data from T1D natural history studies and interventional trials show that β cell loss in those with T1D can be quite variable, especially within the weeks to months following diagnosis. As this study is enrolling participants in close proximity to T1D diagnosis (i.e. within 6 weeks) who are younger, there may be the added complexity of the consideration of the Honeymoon phenomenon (or spontaneous, transient partial remission)—that may last up to ~1 year in the study population (Abdul-Rasoul 2006). The 18-month timing of the primary and key secondary clinical endpoints allows for a substantial amount of the inherent, natural metabolic variability due to different trajectories of β cell loss and/or transiently enhanced β cell function due to the Honeymoon phenomenon to be minimized-so that the true effect on teplizumab on β cell function and clinical parameters can be differentiated from chance.

Other key assessments are done at randomization, Week 26 (6 months) and Week 52 (12 months) to better understand natural history of β cell decline and the effect of teplizumab in this specific study population.

In addition, the primary and key clinical endpoints are assessed approximately 1 year after the last dose of study drug administration. The length of effect is recognized as an important property of an intermittent disease modifying therapy for T1D. A 12-month off-therapy period whilst maintaining positive metabolic and clinical effects can, at this time, be considered a reasonable time frame to substantiate an assertion of a metabolically and clinically relevant durable benefit.

Throughout this study, participants are assessed regularly via in-person interviews and physical exams, self-reports, and laboratory examinations. Assessments occur daily during the two 12-day treatment courses and regularly during the 6-month interval between courses and the 12 months following the second treatment course. The on- and off-therapy observation times in this study are well within, if not significantly beyond, the periods traditionally used to assess for safety and side effects for immune therapies approved for other autoimmune conditions, including those for pediatric indications. In doses and regimens similar to that being used in this study, teplizumab has overall been well tolerated with minimal side effects and no signals of significant short- or long-term adverse effects. It is anticipated that with additional, confirmatory data from this study, the side-effect profile of teplizumab will continue to be considered acceptable for its integration into care plans for children and adolescents newly diagnosed with T1D.

In some embodiments, T1D diagnosis is according to ADA criteria. In some embodiments, the patient diagnosed with T1D has a positive result on testing for at least one of the following T1D-related autoantibodies: Glutamic acid decarboxylase 65 (GAD65) autoantibodies, Islet antigen 2 (IA-2) autoantibodies, Zinc transporter 8 (ZnT8) autoantibodies Islet cell cytoplasmic autoantibodies (ICA) or Insulin autoantibodies (if testing obtained within the first 14 days of insulin treatment).

At the beginning of each 12-day course of study drug administration (Day 1 and Day 182), the participant's current BSA is calculated using the Mosteller formula, BSA=square root [height (cm)×weight (kg)/3600], using the height and weight of the obtained on that day.

Teplizumab and placebo are prepared according to the Pharmacy Manual provided to the site.

Polyvinyl chloride (PVC) infusion bags and tubing and normal saline should be used for study agent preparation and administration.

Two (2) mL of study drug should be drawn from the study drug vial and slowly reconstituted in 18 mL of 0.9% sodium chloride solution for injection by gentle mixing. The resulting 20 mL of 1:10 dilution is used as the initial study drug solution, which contains either placebo or teplizumab at a concentration of 100 μg/mL. This initial drug solution should then be added to a PVC infusion bag containing 25 mL 0.9% sodium chloride solution. Finally, this resulting preparation should be gently mixed before administration to the participant.

This study requires two courses of intravenous infusions and blood draws over 12 days. It is recognized that intravenous access (for infusions and blood draws for laboratory sampling) in the pediatric population that is the focus of this study may pose a challenge. Children have smaller veins than adults, veins that may be more challenging to insert catheters and they may have a significant resistance to catheter placement and/or phlebotomy.

In recognition of the above, in addition to the use of "traditional" intravenous peripheral catheters, this study permits the use of temporary, intermediate term approaches for vascular access. Specifically, "midlines" or peripherally inserted central catheter (PICC) lines may be used for study drug infusions and blood draws (if appropriate according to the properties of the access line and local, regional or national guidance).

All enrolled participants, with assistance of their healthcare providers, should receive intensive diabetes management of their T1D using approved therapies according to the recommendations of American Diabetes Association (ADA) or local, regional, or national recommendations to achieve glucose levels that appear to decrease some of the short-term and long-term sequelae of T1D. Currently the glycemic targets by the ADA are focused at management strategies to achieve a HbA1c level of <7.5% (58 mmol/mol) for individuals 17 years old and younger, and <7.0% (53 mmol/mol) 18 years and older while minimizing severe or frequent hypoglycemic events.

The glycemic goal should be attempted through proper glycemic monitoring, administration of exogenous insulin, and monitoring of activity level and diet. Exogenous insulin may include rapid, intermediate, and/or long-acting insulins, administered intermittently or via the use of a personal insulin pump. Blood glucose levels should be measured at least 4 times a day, including before meals and before bedtime.

Insulin use, including the type of products, dosages, and dosing schedules, is expected to change during the course of the study. As part of routine T1D clinical care, if the caring physician judges it to be clinically appropriate, a participant's insulin dose may be increased, reduced, or even discontinued.

If participants are not meeting the glycemic goals, the study team should contact the participant's primary clinical care team about possible adjustments in the insulin regimen, referral to a registered dietitian, or other approaches that may improve the glucose control.

Insulin Discontinuation

If a participant has achieved a HbA1c level of ≤6.5% with insulin use of ≤0.25 U/kg/day, insulin therapy can be discontinued. The participant's blood glucose and HbA1c levels should continue to be monitored per protocol, and urine ketones should be monitored once a day. During routine blood glucose monitoring, if the participant's blood glucose level exceeds 200 mg/dl (11.1 mmol/L) and/or urine ketone is moderate or greater, the participant should consult with their primary physician and/or the clinical site staff for further evaluation. If the fasting blood glucose exceeds 126 mg/dL (7 mmol/L) or HbA1c exceeds 6.5%, as documented by repeat testing, the resumption of insulin therapy should be considered.

Dosing of the study drug (teplizumab or placebo) is based on the BSA using the height and weight obtained at this visit and the Mosteller formula (BSA=square root [height (cm)× weight (kg)/3600].)

Study Visit Week 1

Patient receives premedication of an NSAID (eg, ibuprofen) (acetaminophen if NSAID is contraindicated) and an antihistamine (eg, diphenhydramine) for at least the first 5 days of the treatment course, unless contraindicated by drug allergy or sensitivity. After at least 30 minutes following the premedication administration, the infusion of study drug can begin. Because there is no preservative and drug loss may occur over time, administration of study drug should begin as soon as possible after preparation and no later than 2 hours after preparation. Study drug should be planned to be administered intravenously over 30 minutes according to standard practices, but it may be slowed if there are signs or symptoms of intolerance. When the contents of the infusion bag have been completely administered, an additional volume of saline equal to the volume contained in the infusion tubing, at the same constant rate is to be infused to ensure that all study drug has been cleared from the infusion tubing. The starting and ending times for the infusion are to be recorded.

Day 2-12: Continued Treatment Course 1 Infusions

If there are no clinical or laboratory concerns, the patient can proceed with the next infusion as described above at least 30 minutes following administration of prophylactic NSAID (acetaminophen if NSAID is contraindicated) and antihistamine. Close monitoring is to occur during the infusions and for 60 minutes following the infusions for any signs or symptoms of intolerability or infusion reactions.

Day 2-11

On Days 2-11, the patient is then able to leave the facility and return the following day for the next study drug infusion.

Days 12

The Day 12 following the completion of the final infusion for this course and at least a 30-minute observation a continuous Glucose Monitoring (CGM) sensor is applied and the participant is to be given instructions on CGM monitoring care and use.

Study Visits Weeks 4, 8, 12, and 20

The visit window for these study visits are ±4 days from the target visit day. During these visits, participants return to the site for their scheduled visit and have clinical and/or laboratory assessments conducted. Of note at Week 12, a CGM sensor is applied and the participant is to be given instructions on CGM monitoring care and use.

At the Week 20 visit, give participant instructions for Week 26 4 h MMTT including overnight fast and pre-MMTT insulin dosing.

Study Visit Week 26: 4 h MMTT and Treatment Course 2

The visit window for these study visits are ±3 days from the target visit day.

Days 182-193

Day 182 clinical and laboratory assessments (including a 4 h MMTT) and for initiation of the second course of study drug administration.

Of specific note, height and weight are to be obtained at this visit and used for the BSA based dosing calculation for course 2. Following the guidance as with study drug course 1, the patient is to be premedicated with an oral NSAID (acetaminophen if NSAID is contraindicated) and antihistamine at least 30 minutes before the first 5 study drug infusions is started (and on an as needed basis with subsequent infusions), administration of study drug should begin as soon as possible after preparation and no later than 2 hours after preparation, and an additional volume of saline equal to the volume contained in the infusion tubing is to be infused. During the infusions and for an additional 60 minutes following the infusions participants are to be monitored for signs or symptoms of infusion reactions.

On certain days, two blood draws are obtained for teplizumab serum levels. One within 30 minutes before study agent infusion and the other within 30 minutes following study agent infusion and flush.

Days 183-192 (Day 2-11 of Course 2 Dosing)

On Days 183-192, the participant may leave the facility and return the following day for the next study drug infusion.

Day 193 (Day 12 of Course 2 Dosing)

Following the completion of the final infusion for this course and at least a 30-minute observation, a CGM sensor is applied and the patient is to be given instructions on CGM monitoring care and use.

Study Visits Week 30, 34, 39, 52 and 65

The visit window for these study visits are ±4 days from the target visit day. At the Week 52 visit, a 4 h MMTT is conducted.

At the end of the Week 39, 52, and 65 visits, a CGM sensor is to be applied and additional training and instruction updates on CGM care and use is given as needed.

Study Visits Week 39 and Week 65

Give patient instructions for Week 52 and Week 78, respectively, 4 h MMTT including overnight fast and pre-MMTT insulin dosing. At the Week 65 visit, dispense to patient CGM equipment for home application to start around Week 76.

Study Visit Week 78

The visit window for this study visit is ±7 days from the target visit day. During this visit the 4 h MMTT is conducted.

Mixed Meal Tolerance Tests

A 2 h MMTT is performed at screening to determine study eligibility (based on peak C-peptide level). A 4 h MMTTs is performed at randomization and at Weeks 26, 52, and 78 to obtain 4 h C-peptide AUCs and other data. A 4 h MMTT is used at and post-randomization as it has been shown to be more precise and reliable in assessing the MMTT-induced C-peptide AUC than the 2 h MMTT (Boyle 2015, Rigby 2013, Rigby 2016). Alternatively, the 2 h-MMTT is used at screening as it is sufficient to capture the peak C-peptide level needed for study entry. Samples from these assessments are assessed for C-peptide, serum glucose, and insulin. Samples are stored for potential future evaluations including but not limited to proinsulin levels. The measurements of C-peptide and glucose in serum samples are done. MMTTs are to take place in the morning between approximately 7:00 a.m. and 10:00 a.m. after an overnight fast with strict guidance on insulin use. The 2-hour MMTT takes approximately 130 minutes to perform, and the 4-hour MMTT takes approximately 250 minutes.

Hemoglobin A1c

HbA1c is assessed as a blood test at select study visits

Insulin Use

Patient's daily insulin use is documented by the participant in an eDiary at select times for 7 days prior to randomization and at about Weeks 12, 26, 39, 52, 65 and 78 visits. The patient records all short-, intermediate- and long-acting insulin administered as intermittent injections or use with an "insulin pump" during this time. Insulin use data are not recorded on the day before or the day of the study visit. If a patient forgets to record insulin use on one or more days before a visit, they should continue to record insulin use for up to 72 hours post-dose to obtain up to 7 days of data. Every effort should be made to collect a total of 7 days of insulin use data for all the aforementioned visits except Week 78 (final visit), as patients return the eDiary at the final visit.

Episodes of Hypoglycemia

Clinically important and other non-severe and non-serious hypoglycemic episodes are recorded throughout the study by participants and through evaluation of glucometer readings.

Glucose Monitoring (1) Intermittent Glucose Monitoring (Fingerstick)

Blood glucose levels outside of MMTT and CGM are recorded and analyzed as an endpoint at various times. As part of routine care, BG levels are usually measured by a fingerstick glucometer at least 4 times a day, including before each meal and at bedtime. At screening, participants are offered a study-supplied glucometer and glucometer strips, but participants are permitted to use their own glucometers if they choose, in which case glucose monitoring strips are not be supplied. Each participant is instructed to bring their glucometer (or glucometers if they use more than one, eg, at home and in school) to each visit for review. In addition, approximately 7 times throughout the study, participants record their BG levels before breakfast, lunch, and dinner and at bedtime for 7 consecutive days in their study eDiary prior to the randomization visit and the Weeks 12, 26, 39, 52, 65, and 78 visits. Like the recording of the insulin use data, BG data on the day before and the day of the study visit are not be recorded. If a participant forgets to record fingerstick glucose measurements before a visit, they should do so for 72 hours immediately after the visit. Every effort should be made to collect a total of 7 days of BG data for all the aforementioned visits except Week 78 (final visit), as participants return the eDiary at the final visit.

(2) Continuous Glucose Monitoring

"Continuous" glucose monitors record interstitial glucose levels (which closely approximate blood glucose values) at regular intervals, eg every 5-15 minutes depending on device. Increasingly clinical studies are supporting that such measurements and their assessments provides valuable and unique insights to glycemic control in diabetes. In this study, CGM assessments are conducted to provide key secondary clinical and exploratory endpoint data to address if and how teplizumab affects glycemic control, such as glucose excursions, time in select glucose ranges, and average daily glucose values (Steck 2014, Helminen 2016, Danne 2017). A recent international consensus statement on CGM monitoring supported the use of percentages of time in ranges (target, hypoglycemia, and hyperglycemia) and measurement of glycemic variability as key diabetes control metrics in clinical trials (Danne 2017).

CGM are used to assess glycemic control approximately 7 times throughout the study: after the completion of treatment courses at randomization and Week 26; after the visit at Weeks 12, 39, 52, and 65; and before the visit at Week 78. CGM sensors are placed by qualified study staff, and education and training on CGM use and care are given. Sensors remain in place for up to 2 weeks. If during that 2-week period a sensor comes off, it can be replaced by the participant, a knowledgeable family member/guardian, or a qualified medical professional.

To reduce any confounding factors of glucose measurements during study drug infusions, CGM sensors are placed on participants after the study drug administration has completed for Course 1 and Course 2 and other clinical and laboratory assessments have been made on the days specified in the Schedule of Events tables. At the Weeks 12, 39, 52, and 65 visits, the sensor is placed on participants after all clinical and laboratory assessments and the MMTT have completed.

Study CGM readings are not intended for medical management of participant's diabetes but can be under the supervision of a participant's health care team. Of note, routine use of the personal CGM under guidance of a participant's regular healthcare provider is permitted.

Spot-check and CGM blood glucose assessments are anticipated to include but are not be limited to mean BG, glycemic variability (BG standard deviation [SD]), maximum and minimum BG values over time and incidence and/or percent time with BG >70 but ≤180 mg/dl (>3.9 but ≤10.0 mmol/L, Level 1 (>180 but ≤250 mg/dL (>10 but ≤13.9 mmol/L)) and Level 2 HYPERglycemia (>250 mg/dL (>13.9 mmol/L)) and Level 1 (≤70 but ≥54 mg/dl (≤3.9 but ≥3.0 mmol/L)) and Level 2 (<54 mg/dL (<3.0 mmol/L)) HYPOglycemia (Seaquist 2013, International Hypoglycaemia Study Group [IHSG] 2017, Agiostratidou 2017).

Example 3. Meta-Analysis of C-peptide in Five Stage 3 T1D Studies

Summary

Confirmatory evidence in the form of a meta-analysis was conducted using pooled C-peptide data from 5 supportive studies, all of which were randomized clinical studies: Protégé, Encore, Study 1, AbATE, and Delay. These 5 studies compared teplizumab to either placebo or standard of care in newly diagnosed patients with Stage 3 clinical T1D and had similar designs that allowed for cross-study comparisons (Table 5).

The meta-analysis evaluated the change from baseline in C-peptide AUC in a 4-hour mixed meal tolerance test (MMTT). Analysis of covariance (ANCOVA) was used to predict mean C-peptide values (least square means) as well as respective treatment differences. The meta-analysis had 2 components: one analysis was performed on all 5 studies through 1 year of follow-up, and a second analysis was performed on the 3 studies that had 2 years of follow-up.

In the meta-analysis of the 1-year (FIG. 26) and 2-year C-peptide data (FIG. 27), patients treated with teplizumab showed significantly higher C-peptide levels compared to control (p<0.001 for both). This effect was consistent for observed and imputed data at both 1 year and 2 years, as well as in sensitivity analyses that assigned control data to missing data in the teplizumab group.

In order to assess whether C-peptide differed between those who were free of T1D and those who developed T1D, separate plots of mean C-peptide over time were developed.

As can be seen in FIG. 28, those treated with teplizumab who remain free of T1D or ultimately develop T1D during the study had higher mean C-peptide values compared with their respective controls.

Study Design

Confirmatory evidence in the form of a meta-analysis was conducted using pooled C-peptide data from 5 supportive randomized clinical studies: Protégé, Encore, Study 1, AbATE, and Delay. C-peptide AUC levels were obtained from a 4-hour MMTT.

Table 5 shows study design features across these 5 studies in Stage 3 T1D patients. These studies were chosen because they represented all the randomized studies conducted with teplizumab in Stage 3 T1D and used either placebo or standard of care as controls. A similar 14-day escalating dose regimen was used across the studies. In Study 1, a 14-day dosing regimen based on weight was subsequently modified to a 12-day dosing regimen based on BSA. However, due to apparently more AEs occurring during the early dosing period in the 12-day regimen with a 2-day ramp-up period, a 14-day regimen with a 4-day ramp-up period was adopted in subsequent clinical studies. Patients received two 14-day treatment courses in Protégé, Encore, and AbATE, and a single course of treatment at baseline in Delay and Study 1. The Protege and Encore studies enrolled newly diagnosed patients with Stage 3 T1D in 4 treatment arms: placebo and 3 teplizumab dosing regimens (full-dose 14 days [9.0 mg/m$^2$ cumulative dose], one-third dose 14 days [~3.0 mg/m$^2$ cumulative dose] and truncated 6-days [~2.5 mg/m$^2$ cumulative dose]). In the meta-analysis, C-peptide data from the full-dose 14-day regimen was used. Study 1, AbATE, and Delay studies all used the full-dose 14-day regimen (9.0 mg/m$^2$ cumulative dose).

TABLE 5

Study Design Features Across Supportive Studies

|  | Protégé | Encore | Study 1 | AbATE | Delay |
|---|---|---|---|---|---|
| Follow-up | Baseline, Day 140, Months 12, 18, 24 | Baseline, Day 140, Months 12, 18, 24 | Baseline, Months 6, 12, 18, 24 | Baseline, Months 6, 12, 18, 24 | Baseline, Months 6, 12 |
| C-peptide endpoint status | Secondary, time not specified | Secondary, time not specified | Primary, at 2 years | Primary, at 2 years | Primary, at 1 year |
| Dosing schedule | 14 days | 14 days | 12 or 14 days | 14 days | 14 days |
| Regimen | 2 courses: Baseline, 6 months | 2 courses: Baseline, 6 months | 1 course: Baseline | 2 courses: Baseline, 12 months | 1 course: Baseline |
| Design | Randomized, double-blind | Randomized, double-blind | Randomized, open-label | Randomized, open-label | Randomized, double-blind |
| Control group | Placebo | Placebo | Standard care | Standard care | Placebo |
| Number of patients* | Placebo: 98 Teplizumab: 453 | Placebo: 62 Teplizumab: 192 | Control: 21 Teplizumab: 21 | Control: 25 Teplizumab: 52 | Placebo: 27 Teplizumab: 31 |

*Patients in the full 14-day teplizumab treatment regimen and placebo groups were included in the meta-analyses.

The patients enrolled in these studies (Table 6) were representative of the newly diagnosed T1D patient population, excluding those with significant medical history, clinical abnormalities, or active infection. Key inclusion criteria were similar across the studies. C-peptide level at study entry was ≥0.2 nmol/L in AbATE, Delay, and Study 1 and detectable levels for Protégé and Encore.

TABLE 6

| Key Inclusion Criteria Across the Supportive Studies | | | | | |
| --- | --- | --- | --- | --- | --- |
| | Protégé | Encore | Study 1 | AbATE | Delay |
| Age at entry | 8-35 years | 8-35 years | 7.5-30 years | 8-30 years | 8-30 years |
| Time of T1D diagnosis to treatment | ≤12 weeks | ≤12 weeks | ≤6 weeks | ≤8 weeks | 4-12 months |
| Autoantibodies[1] | anti-ICA512, IA-2, anti-GAD65, IAA | anti-ICA512, IA-2, anti-GAD65, IAA | anti-GAD65, anti-ICA512, IAA | ICA, anti-GAD65, anti-ICA512 | ICA, anti-GAD65, anti-ICA512 |
| C-peptide level | detectable | detectable | ≥0.2 nmol/L | ≥0.2 nmol/L | ≥0.2 nmol/L |
| Weight | ≥36 kg | ≥36 kg | N/A | ≥25 kg | ≥27.5 kg |

[1]At least 2 of these antibodies were present at study entry.
Abbreviations:
Anti-GAD65 = anti-glutamic acid decarboxylase 65 antibody,
IA-2 = islet antigen,
IAA = insulin autoantibodies,
Anti-ZnT8 = zinc transporter 8 antibody,
CI = confidence interval,
HLA = human leukocyte antigen,
anti-ICA512 = anti-islet cell antibody,
N/A = not available,
T1D = type 1 diabetes The primary endpoint of the meta-analyses was the change from baseline in C-peptide AUC in a 4-hour MMTT. Each study used the same sample collection time points during the MMTTs to calculate C-peptide AUC.

Meta-Analysis of Change from Baseline in C-Peptide AUC in a 4-Hour MMTT

Patients in the teplizumab group had greater preservation of C-peptide (ie, smaller decreases from baseline) at 1 year and 2 years of follow-up. This effect was consistent for observed data and imputed data ($p < 0.0001$ for both analyses). Furthermore, the conservative sensitivity analysis applying control-based imputation (assigning control data to missing teplizumab data) was also significant ($p < 0.0001$).

The results for the 1-year and 2-year meta-analyses are shown in forest plots in FIG. 26 and FIG. 27, respectively. Both forest plots show that the observed (existing) and imputed analyses yielded consistent effects of teplizumab in preserving C-peptide AUC levels. In the 1-year forest plot, teplizumab treatment was consistently more effective than placebo in all studies, except Encore. The result in the Encore study was expected, as the study was modified before its completion due the companion Phase 3 study, Protégé, not meeting its 1-year primary endpoint, resulting in a large amount of missing data requiring the largest amount of imputation. Approximately 75% (93/125) of the MMTTs were missing. The primary endpoint of the Protégé study was a novel unvalidated composite endpoint focused on metabolic parameters (HbA1c and insulin use).

In the forest plot of 2-year data (FIG. 27), teplizumab treatment significantly preserved C-peptide AUC levels compared with placebo in all 3 studies with 2-year data.

Example 4. Insulin Use in Five Stage 3 T1D Studies

In the same 5 studies included in the C-peptide meta-analysis in Example 3, exogenous insulin use was evaluated individually in each study. The mean insulin use over each timepoint in each study was numerically lower in teplizumab-treated patients compared to placebo (FIGS. 29a-29e). In 2 of the studies (AbATE, Study 1) the difference was statistically significant.

Specifically, in all 5 studies, the mean insulin use over each timepoint was lower in teplizumab patients compared to placebo patients (FIGS. 29a-29e). Three studies (AbATE, Delay, and Study 1) showed that teplizumab treatment consistently led to statistically significantly lower levels of insulin requirement compared with placebo (Herold et al 2013a; Herold et al 2005; Herold et al 2013b). The insulin use in the teplizumab group was also lower compared to the placebo group but did not achieve statistical significance in the Protégé and Encore studies. Thus, teplizumab treatment preserves C-peptide levels as reflected by greater endogenous insulin production and less exogenous insulin requirement.

Overall, these data support that teplizumab preserves beta cell function, as measured by C-peptide levels, and correspondingly, endogenous insulin production, resulting in a lower need for exogenous insulin.

Example 5: Clinical Pharmacokinetics and Pharmacodynamics

Mechanism of Action: Teplizumab is a humanized monoclonal antibody that targets the cluster of differentiation 3 (CD3) antigen, which is co-expressed with the T-cell receptor (TCR) on the surface of T lymphocytes. Though the mechanism of action of teplizumab for the proposed indication has not been confirmed, it appears to involve weak agonistic activity on signaling via the TCR-CD3 complex, which is thought to expand regulatory T-cells and re-establish immune tolerance.

Pharmacokinetics: FIGS. 30A-30B shows plots of predicted mean teplizumab concentrations over time using a 14-day intravenous (IV) dosing regimen with a 4-day ramp-up followed by repeated doses of 826 μg/m² on Days 5 to 14. The left panel represents a typical 60 kg male subject (FIG. 30A) and the right panel represents a typical 40 kg and 90 kg male subject (FIG. 30B). Body surface area (BSA)-based dosing normalizes the exposure across body size.

The repeated IV infusions resulted in increasing serum teplizumab levels, although steady-state PK was not achieved at the end of dosing (Day 14 with this dosing regimen). The average accumulation ratio for area under the curve (AUC) between Day 5 and Day 14 was 3.4. The predicted mean (±SD) total AUC for the 14-day dosing regimen was 6421±1940 ng·day/mL with Cmax and Cmin of 826±391 and 418±225 ng/ml, respectively, on Day 14.

Distribution: The central and peripheral volume of distribution from population PK analysis was 3.4 L and 6.9 L, respectively.

ately following IV infusion (Cmax of the commercial product was 94.5% (90% CI: 84.5 to 106) of that observed in the clinical trial drug product).

Example 6. Adverse Events

Adverse events associated with teplizumab administration are also being studied. Notably, while teplizumab does not have an overall infection safety signal to date, patients receiving the 12-day dosing regimen (1 or 2 courses) instead of 14-day regimen appear to report fewer numeric adverse events of infection, based on the data from completed studies (Table 7).

TABLE 6

| TEAEs by number of doses, SOC and preferred term (Safety population) - Event count | | | | |
|---|---|---|---|---|
| System organ class | Preferred term | All doses received (N = 6370) n (%) | 12 doses received (N = 52) n (%) | Teplizumab Full Regiman (N = 8345) n (%) |
| Skin and subcutaneous tissue disorders | Vitliligo | 0 | 0 | 1 (0.0) |
| Infections and infestations | -Total | 526 (8.3) | 2 (3.8) | 680 (7.9) |
| | Upper respiratory tract infection | 149 (2.3) | 0 | 184 (2.2) |
| | Nasopharyngitis | 44 (0.7) | 0 | 66 (0.8) |
| | Pharyngitis | 36 (0.6) | 0 | 39 (0.5) |
| | Sinusitis | 22 (0.3) | 0 | 28 (0.3) |
| | Rhinitis | 17 (0.3) | 0 | 20 (0.2) |
| | Gastrocentereritis viral | 13 (0.2) | 0 | 18 (0.2) |
| | Pharyngitis streptococcal | 12 (0.2) | 0 | 16 (0.2) |
| | Epstein-Barr viraemia | 10 (0.2) | 0 | 15 (0.2) |
| | Influenza | 14 (0.2) | 0 | 14 (0.2) |
| | Conjunctivitis | 11 (0.2) | 0 | 13 (0.2) |
| | Ear infection | 6 (0.1) | 0 | 13 (0.2) |
| | Epstein-Barr virus infection | 11 (0.2) | 1 (1.9) | 13 (0.2) |
| | Viral upper respiratory tract infection | 11 (0.2) | 0 | 12 (0.1) |
| | Gastroenteritis | 7 (0.1) | 0 | 10 (0.1) |

Note:
The denominator in percent calculation is the number of subjects in each treatment group and subgroup level for subject count and the number of events in each treatment group and subgroup level for event count.
Note:
Delay subjects initially randomized to the Placebo arm, who were later also eligible for the open-label cycle 2 administration of Teplizumab, are included only for the Teplizumab period.
Note:
Subjects were considered under 'All doses received' if they had 14 doses administered during cycle 1, or they had 14 doses administered during both cycle 1 and 2 if they participated in two cycles. If subjects had 12 doses administered during cycle 1 or the sum of doses during cycle 1 and 2 was 12, they were considered under '12 doses received'.
Note:
System organ classes (SOCs) and preferred terms are based on MedDRA version 23.0.
Note:
TEAE = Treatment-Emergent Adverse Event.

Elimination: Teplizumab clearance is not dose-proportional, likely driven by its saturable binding to CD3 receptors on the T-cell surface. Teplizumab is expected to be degraded into smaller peptide fragments by catabolic pathways. The clearance of teplizumab following the 14-day dosing regimen was estimated from population PK analysis to be 2.3 L/day, with a terminal half-life of approximately 4 days.

The planned commercial drug product is manufactured in a different facility from the clinical trial product and was not used in the clinical studies submitted to support efficacy and safety. A single-dose PK bridging study was conducted in healthy volunteers that evaluated the biocomparability of the commercial drug product with the clinical trial drug product. The mean AUC0-inf for the commercial product was less than half (48.5%, 90% CI: 43.6 to 54.1) of the AUC0-inf for the product used in the primary efficacy study. The reason for this difference seems to be faster clearance of the drug from circulation rather than differences in the strength of the product, as similar concentrations were observed immedi- Modifications and variations of the described methods and compositions of the present disclosure will be apparent to those skilled in the art without departing from the scope and spirit of the disclosure. Although the disclosure has been described in connection with specific embodiments, it should be understood that the disclosure as claimed should not be unduly limited to such specific embodiments. Indeed, various modifications of the described modes for carrying out the disclosure are intended and understood by those skilled in the relevant field in which this disclosure resides to be within the scope of the disclosure as represented by the following claims.

INCORPORATION BY REFERENCE

All patents and publications mentioned in this specification are herein incorporated by reference to the same extent as if each independent patent and publication was specifically and individually indicated to be incorporated by reference.

REFERENCES

Abdul-Rasoul M, Habib H, Al-Khouly M. "The honeymoon phase" in children with type 1 diabetes mellitus: frequency, duration, and influential factors. Pediatr Diabetes. 2006; 7(2):101-107.

Ablamunits V, Bisikirska B, Herold K C. Acquisition of regulatory function by human CD8+ T cells treated with anti-CD3 antibody requires TNF. Eur J Immunol. 2010; 40(10):2891-2901. Agiostratidou G, Anhalt H, Ball D, et al. Standardizing clinically meaningful outcome measures beyond HbA1c for type 1 diabetes: a consensus report of the American Association of Clinical Endocrinologists, the American Association of Diabetes Educators, the American Diabetes Association, the Endocrine Society, JDRF International, The Leona M. and Harry B. Helmsley Charitable Trust, the Pediatric Endocrine Society, and the T1D Exchange. Diabetes Care. 2017; 40(12):1622-1630.

Akirav E M, Kushner J A, Herold K C. β cell mass and type 1 diabetes: Going, going, gone? Diabetes. 2008; 57:2883-2888.

American Diabetes Association. 12. Children and Adolescents: Standards of medical Care in Diabetes-2018. Diabetes Care. 2018; 41(Suppl. 1):S126-S136.

Atkinson M A. Type 1 diabetes. Lancet. 2014; 383(9911): 69-82

Bisikirska B, Colgan J, Luban J, Bluestone, J A, Herold K C. TCR stimulation with modified anti-CD3 mAb expands CD8+ T cell population and induces CD8+ CD25+ Tregs. J Clin Invest. 2005; 115(10):2904-2913.

Bluestone J A, Herold K, and Eisenbarth G. Genetics, pathogenesis and clinical interventions in type 1 diabetes. Nature. 2010; 464(7293):1293-1300.

Boyle K D, Keyes-Elstein L, Ehlers M R, et al. Two- and four-hour tests differ in capture of C-peptide responses to a mixed meal in type 1 diabetes. Diabetes Care. 2016; 39:e76-78.

Bradley C, Loewenthal K, Woodcock A, et al. Development of the diabetes treatment satisfaction questionnaire (DTSQ) for teenagers and parents: the DTSQ-Teen and the DTSQ-Parent. Diabetologia. 2009; 52: (Suppl 1) S397, Abstract 1013.

Campbell-Thompson M, Fu A, Kaddis J S, et al. Insulitis and B-cell mass in the natural history of type 1 diabetes. Diabetes. 2016; 65:719-731.

Danne T, Nimri R, Battelino T, et al. International consensus on use of continuous glucose monitoring. Diabetes Care 2017; 40:1631-1640.

Diabetes Control and Complications Trial Research Group. Hypoglycemia in the Diabetes Control and Complications Trial. Diabetes. 1997; 46(2):271-286.

DiMeglio L A, Acerini C L, Codner E, et al. ISPAD Clinical Practice Consensus Guidelines 2018: Glycemic control targets and glucose monitoring for children, adolescents, and young adults with diabetes. Pediatr Diabetes. 2018 October; 19 Suppl 27:105-114.

Driscoll K A, Raymond J, Naranjo D, et al. Fear of hypoglycemia in children and adolescents and their parents with type 1 diabetes. Curr Diab Rep. 2016; 16(8):77.

European Medicines Agency. Ethical Considerations for Clinical Trials on Medicinal Products Conducted with the Paediatric Population. 2008. https://ec.europa.eu/health/sites/health/files/files/eudralex/vol-10/ethical-_considerations_en.pdf. Accessed Sep. 27, 2018.

Fonolleda M, Murillo M, Vázquez F, et al. Remission phase in paediatric type 1 diabetes: new understanding and emerging biomarkers. Horm Res Paediatr. 2017; 88(5):307-315.

Gitelman S E, Gottlieb P A, Rigby M R, et al. Antithymocyte globulin treatment for patients with recent-onset type 1 diabetes: 12-month results of a randomised, placebo-controlled, phase 2 trial. Lancet Diabetes Endocrinol. 2013; 1(4):306-16.

Gonder-Frederick L, Nyer M, Shepard J A. Assessing fear of hypoglycemia in children with Type 1 diabetes and their parents. Diabetes Manag (Lond). 2011; 1(6):627-639.

Greenbaum C J, Beam C A, Boulware D et al. Fall in C peptide during first 2 years from diagnosis: evidence of at least two distinct phases from composite type 1 diabetes TrialNet data. Diabetes. 2012; 61:2066-2073.

Hagopian W, Ferry R J Jr, Sherry N et al, Protégé Trial Investigators. Teplizumab preserves C-peptide in recent-onset type 1 diabetes: two-year results from the randomized, placebo-controlled Protégé trial. Diabetes. 2013; 62(11):3901-8. doi: 10.2337/db13-0236. Epub 2013 Jun. 25.

Helminen O, Pokka T, Tossavainen P, et al. Continuous glucose monitoring and HbA1c in the evaluation of glucose metabolism in children at high risk for type 1 diabetes mellitus. Diabetes Res Clin Pract. 2016; 120: 89-96.

Herold K C, Hagopian W, Auger J A, Poumian-Ruiz E, Taylor L, Donaldson D, Gitelman S E, Harlan D M, Xu D, Zivin R A, Bluestone J A. Anti-CD3 monoclonal antibody in new-onset type 1 diabetes mellitus. N Engl J Med. 2002 May 30; 346(22):1692-1698.

Herold K C, Gitelman S E, Umest M et al. A single course of anti-CD3 monoclonal antibody hOKT3γ1 (Ala-Ala) results in improvement in C-peptide responses and clinical parameters for at least 2 years after onset of type 1 diabetes. Diabetes. 2005; 54:1-7.

Herold K C, Gitelman S E, Ehlers M R, et al. Teplizumab (anti-CD3 mAb) treatment preserves C-peptide responses in patients with new-onset type 1 diabetes in a randomized controlled trial: metabolic and immunologic features at baseline identify a subgroup of responders. Diabetes. 2013(a); 62(11):3766-3774.

Herold K C, Gitelman S E, Willi S M, et al. Teplizumab treatment may improve C-peptide responses in participants with type 1 diabetes after the new-onset period: a randomised controlled trial. Diabetologia. 2013 (b); 56(2):391-400.

Herold K C, Bundy B N, Long S A, et al. An Anti-CD3 Antibody, Teplizumab, in Relatives at Risk for Type 1 Diabetes. N Engl J Med. 2019 Jun. 9. doi: 10.1056/NEJMoa1902226. [Epub ahead of print]

Huo L, Harding J L, Peeters A, et al. Life expectancy of type 1 diabetic patients during 1997-2010: a national Australian registry-based cohort study. Diabetologia. 2016; 59(6):1177-85. International Hypoglycaemia Study Group. Glucose Concentrations of Less Than 3.0 mmol/L (54 mg/dL) Should Be Reported in Clinical Trials: A Joint Position Statement of the American Diabetes Association and the European Association for the Study of Diabetes. Diabetes Care. 2016; dc162215.

Joint Commission. High Alert Medications and Patient Safety. Sentinel Event Alert. Issue 11. November 19,1999. https://www.jointcommission.org/assets/1/18/SEA_11.pdf. Accessed Aug. 21, 2018.

Karvonen M, Viik-Kajander M, Moltchanova E, et al. Incidence of childhood type 1 diabetes worldwide. Diabetes Mondiale (DiaMond) Project Group. Diabetes Care. 2000; 23(10):1516-1526.

Kuhtreiber W M, Washer S L, Hsu E, et al. Low levels of C-peptide have clinical significance for established Type 1 diabetes. Diabet Med. 2015 October; 32(10): 1346-53.

Lachin J M, McGee P, Palmer J P; DCCT/EDIC Research Group. Impact of C-peptide preservation on metabolic and clinical outcomes in the Diabetes Control and Complications Trial. Diabetes. 2014; 63(2):739-748.

Laitinen O H, Honkanen H, Pakkanen O, et al. Coxsackievirus B1 is associated with induction of β-cell autoimmunity that portends type 1 diabetes. Diabetes. 2014; 63(2):446-455.

Lebastchi J, Deng S, Lebastchi A H, et al. Immune therapy and β-cell death in type 1 diabetes. Diabetes. 2013; 62(5):1676-1680.

Lin A, Northam E A, Werther G A, Cameron F J. Risk factors for decline in IQ in youth with type 1 diabetes over the 12 years from diagnosis/illness onset. Diabetes Care. 2015; 38:236-242.

Lind M, Svensson A M, Kosiborod M, et al. Glycemic control and excess mortality in type 1 diabetes. N Engl J Med. 2014; 371:1972-1982.

Long S A, Thorpe J, DeBerg H A, et al. Partial exhaustion of CD8 T cells and clinical response to teplizumab in new-onset type 1 diabetes. Sci. Immunol. 2016; 1(5): 1-23.

Long S A, Thorpe J, Herold K C, et al. Remodeling T cell compartments during anti-CD3 immunotherapy of type 1 diabetes. Cell Immunol. 2017 September; 319:3-9.

Ludvigsson J, Carlsson A, Deli A, et al. Decline of C-peptide during the first year after diagnosis of Type 1 diabetes in children and adolescents. Diabetes Res Clin Pract. 2013; 100(2):203-209.

Masharani U B, Becker J. Teplizumab therapy for type 1 diabetes. Expert Opin Biol Ther. 2010; 10(3):459-465.

Matveyneko A V and Butler P C. Relationship between β cell mass and diabetes onset. Diabetes Obes Metab. 2008; 10:23-31.

Mittermayer F, Caveney E, De Oliveira C, et al. Addressing Unmet Medical Needs in Type 1 Diabetes: A Review of Drugs Under Development. Curr Diabetes Rev. 2017; 13(3):300-314.

Monaghan M, Helgeson V, Wiebe D. Type 1 diabetes in young adulthood. Curr Diabetes Rev. 2015; 11(4):239-250.

Mortensen H B, Hougaard P, Swift P, et al. New definition for the partial remission period in children and adolescents with type 1 diabetes. Diabetes Care. 2009; 32:1384-1390.

National Cancer Institute. Common Terminology Criteria for Adverse Events (CTCAE). https://ctep.cancer.gov/protocolDevelopment/electronic_applications/ctc.htm. Updated Mar. 1, 2018. Accessed Sep. 27, 2018.

Orban T, Bundy B, Becker D J, et al. Co-stimulation modulation with abatacept in patients with recent-onset type 1 diabetes: a randomised, double-blind, placebo-controlled trial. Lancet 2011; 378(9789):412-419.

Palmer J P, Fleming G A, Greenbaum C J, et al. C-peptide is the appropriate outcome measure for type 1 diabetes clinical trials to preserve beta-cell function: report of an ADA workshop, 21-22 Oct. 2001. Diabetes. 2004; 53(1):250-264.

Palmer J P. C-peptide in the natural history of type 1 diabetes. Diabetes Metab Res Rev. 2009; 25(4):325-328.

Rawshani A, Rawshani A, Franzén S, et al. Mortality and Cardiovascular Disease in Type 1 and Type 2 Diabetes. N Engl J Med. 2017; 376(15):1407-1418.

Rawshani A, Sattar N, Franzén S, et al. Excess mortality and cardiovascular disease in young adults with type 1 diabetes in relation to age at onset: a nationwide, register-based cohort study. Lancet. 2018; 392(10146): 477-486.

Rigby M R, DiMeglio L A, Rendell M S, et al. Targeting of memory T cells with alefacept in new-onset type 1diabetes (T1DAL study): 12-month results of a randomised, double-blind, placebo-controlled phase 2 trial. Lancet Diabetes Endocrinol. 2013; 1(4):284-294.

Rigby M R, Ehlers M R. Targeted Immune Interventions for Type 1 Diabetes: Not as Easy as it Looks! Curr Opin Endocrinol Diabetes Obes. 2014; 21(4):271-278.

Rigby M R, Harris K M, Pinckney A, et al. Alefacept provides sustained clinical and immunological effects in new-onset type 1 diabetes patients. J Clin Invest. 2015; 125(8):3285-3296.

Roark C L, Anderson K M, Simon L J, et al. Multiple HLA epitopes contribute to type 1 diabetes susceptibility. Diabetes. 2014; 63(1):323-331.

Rosenzweig M, Rosenthal C A, Torres V M, Vaickus L. Development of a quantitative assay to measure EBV viral load in patients with autoimmune type 1 diabetes and healthy subjects. J Virol Methods. 2010; 164(1-2): 111-115.

Seaquist E R, Anderson J, Childs B, et al. Hypoglycemia and diabetes: a report of a workgroup of the American Diabetes Association and the Endocrine Society. Diabetes Care. 2013; 36(5):1384-1395.

Secrest A M, Becker D J, Kelsey S F, LaPorte R E, and Orchard T J. Characterising sudden death and dead-in-bed syndrome in Type 1 diabetes: analysis from 2 childhood-onset Type 1 diabetes registries. Diabet Med. 2011; 28(3):293-300.

Sherry N, Hagopian W, Ludvigsson J, et al., Protégé Trial Investigators. Teplizumab for treatment of type 1 diabetes (Protégé study): 1-year results from a randomised, placebo-controlled trial. Lancet. 2011; 378 (9790):487-97.

Sorensen J S, Johannesen J, Pociot F, et al. Residual B-cell function 3-6 years after onset of type 1 diabetes reduces risk of severe hypoglycemia in children and adolescents. Diabetes Care. 2013; 36:3454-3459.

Sosenko J M, Skyler J S, Herold K C, et al. The metabolic progression to type 1 diabetes as indicated by serial oral glucose tolerance testing in the Diabetes Prevention Trial-type 1. Diabetes. 2012; 61(6):1331-7.

Steck A K, Dong F, Taki I, et al. Early hyperglycemia detected by continuous glucose monitoring in children at risk for type 1 diabetes. Diabetes Care. 2014; 37:2031-2033.

Steffes M W, Sibley S, Jackson M, Thomas W. Beta-cell function and the development of diabetes-related complications in diabetes control and complications trial. Diabetes Care. 2003; 26:832-836.

Streisand R. Young children with type 1 diabetes: challenges, research, and future directions. Curr Diab Rep. 2014; 14(9):520. pp1-16.

Trancone A, Bonfanti R, Iafusco D, et al. Evaluating the experience of children with type 1 diabetes and their parents taking part in an artificial pancreas clinical trial over multiple days in a diabetes camp setting. Diabetes Care. 2016; 39:2158-2164.

Varni J W, Delamater A M, Hood K K, et al. PedsQL 3.2 Diabetes Module for children, adolescents, and young adults: reliability and validity in type 1 diabetes. Diabetes Care. 2018; dc172707.

Verkruyse L A, Storch G A, Devine S M, et al. Once daily ganciclovir as initial pre-emptive therapy delayed until threshold CMV load > or =10000 copies/ml: a safe and effective strategy for allogeneic stem cell transplant patients. Bone Marrow Transplant. 2006; 37(1):51-6.

Waldron-Lynch F, Henegariu O, Deng S, et al. Teplizumab induces human gut-tropic regulatory cells in humanized mice and patients. Sci Transl Med. 2012; 4(118):118ra12.

Wherrett D K, Chiang J L, Delamater A M, et al. Defining pathways for development of disease-modifying therapies in children with type 1 diabetes: a consensus report. Diabetes Care. 2015; 38(10):1975-85.

Ziegler A G and Nepom G T. Prediction and pathogenesis in type 1 diabetes. Immunity. 2010; 32:468-478.

---

What is claimed is:

1. A method of delaying progression of Stage 3 type 1 diabetes (T1D) in a patient diagnosed with Stage 3 T1D, comprising administering to the patient two 12-day courses of teplizumab, wherein each 12-day course comprises a first dose of 106 μg/m² teplizumab on day 1, a second dose of 425 μg/m² teplizumab on day 2, and one dose of 850 μg/m² teplizumab on each of days 3-12.

2. The method of claim 1, wherein the two courses of teplizumab are administered at an interval of about 6 months to about 12 months.

3. The method of claim 2, further comprising administering to the patient one or more additional 12-day courses of teplizumab.

4. The method of claim 3, wherein each of the one or more additional 12-day courses of teplizumab comprises a first dose of 106 μg/m² teplizumab on day 1, a second dose of 425 μg/m² teplizumab on day 2, and one dose of 850 μg/m² teplizumab on each of days 3-12.

5. The method of claim 3, wherein each of the additional 12-day courses of teplizumab is administered at about 6 months to about 24 months after the preceding course.

6. The method of claim 2, wherein the second of said two courses of teplizumab is administered to the patient 6-12 months after the first of said two courses of teplizumab.

7. The method of claim 1, comprising
determining, before and after administration of each 12-day course, a baseline of a level of TIGIT+KLRG1+ CD8+ T-cells with respect to all CD3+ T-cells,
monitoring the level of the TIGIT+KLRG1+CD8+ T-cells in all CD3+ T-cells, and
administering an additional 12-day course when the level of the TIGIT+KLRG1+CD8+ T-cells in all CD3+ T-cells returns to the baseline level.

8. The method of claim 7, wherein the level of TIGIT+ KLRG1+CD8+ T-cells in all CD3+ T-cells is measured by flow cytometry.

9. The method of claim 7, comprising determining the level of TIGIT+KLRG1+CD8+ T-cells in all CD3+ T-cells about 1-6 months, 2-5 months, or 3 months after the administration of each 12-day course.

10. The method of claim 7, wherein if the patient has more than 10% TIGIT+KLRG1+CD8+ T-cells in all CD3+ T-cells, subsequent monitoring is annual.

11. The method of claim 7, wherein if the patient has less than 10% TIGIT+KLRG1+CD8+ T-cells in all CD3+ T-cells, subsequent monitoring is about every 3-6 months.

12. The method of claim 1, wherein the patient has been diagnosed with Stage 3 T1D within 6 weeks prior to the administering step.

13. The method of claim 12, wherein the patient in need thereof is 8 years of age or older.

14. The method of claim 1, wherein the administering step results in reduction of insulin use, HbA1c levels, hypoglycemic episodes, or combinations thereof by at least 10% as compared to pre-treatment levels.

15. The method of claim 1, wherein each dose is administered parenterally.

16. The method of claim 1, wherein each dose is administered by intravenous infusion.

17. The method of claim 16, wherein each dose of teplizumab is administered by intravenous infusion over a period of at least 30 minutes.

18. The method of claim 1, wherein the patient in need thereof is 8 years of age or older.

19. The method of claim 1, wherein the patient in need thereof has a peak C-peptide level of ≥0.2 pmol/mL during a mixed meal tolerance test (MMTT).

20. The method of claim 1, wherein the patient receiving teplizumab has a higher mean C-peptide value compared with a control receiving placebo.

21. The method of claim 1, comprising assessing the area under the time-concentration curve (AUC) of C-peptide following a mixed meal tolerance test (MMTT) at 78 weeks.

22. The method of claim 1, wherein the patient has at least 20% of beta-cell function prior to the administering step.

23. The method of claim 1, wherein the patient in need thereof is or has tested positive for at least one T1D-related autoantibody selected from glutamic acid decarboxylase 65 autoantibodies, islet antigen 2 autoantibodies, zinc transporter 8 autoantibodies, islet cell cytoplasmic autoantibodies, and insulin autoantibodies.

24. The method of claim 23, wherein the patient in need thereof has or has tested positive for hyperglycemia or overt hyperglycemia.

25. The method of claim 24, wherein the patient in need thereof has or has tested positive for at least one of the following:
(i) a fasting plasma glucose level of ≥126 mg/dL (7.0 mmol/L);
(ii) a 2-hour plasma glucose level of ≥200 mg/dL (11.1 mmol/L) during an oral glucose tolerance test (OGTT);
(iii) a hemoglobin A1C (HbA1c) level of ≥6.5% (48 mmol/mol); and
(iv) a random plasma glucose level of ≥200 mg/dL (11.1 mmol/L).

26. The method of claim 1, wherein the patient in need thereof has or has tested positive for hyperglycemia or overt hyperglycemia.

27. The method of claim 26, wherein the patient in need thereof has or has tested positive for at least one of the following:
(i) a fasting plasma glucose level of ≥126 mg/dl (7.0 mmol/L);
(ii) a 2-hour plasma glucose level of ≥200 mg/dL (11.1 mmol/L) during an oral glucose tolerance test (OGTT);
(iii) a hemoglobin A1C (HbA1c) level of ≥6.5% (48 mmol/mol); and
(iv) a random plasma glucose level of ≥200 mg/dL (11.1 mmol/L).

28. The method of claim 1, wherein the patient has been diagnosed with Stage 3 T1D within 12 weeks prior to the administering step.

29. The method of claim 1, wherein the two courses of teplizumab are administered at an interval of 6 months.

30. The method of claim 1, wherein the patient has been diagnosed with Stage 3 T1D within 4 months prior to the administering step.

31. The method of claim 1, wherein the patient has been diagnosed with Stage 3 T1D within 12 months prior to the administering step.

32. The method of claim 31, wherein the patient has a non-fasting C-peptide level of ≥0.2 pmol/mL.

33. A method of delaying progression of Stage 3 type 1 diabetes (T1D) in a patient in need thereof, comprising parenterally administering to the patient in need thereof two 12-day courses of teplizumab at an interval of about 6 months to about 12 months, wherein each 12-day course comprises a first dose of 106 µg/m² teplizumab on day 1, a second dose of 425 µg/m² teplizumab on day 2, and one dose of 850 µg/m² teplizumab on each of days 3-12, wherein the patient has been diagnosed with Stage 3 T1D within 12 weeks prior to the administering step.

34. The method of claim 33, further comprising administering to the patient one or more additional 12-day courses of teplizumab.

35. The method of claim 34, wherein each of the additional 12-day courses comprises a first dose of 106 µg/m² teplizumab on day 1, a second dose of 425 µg/m² teplizumab on day 2, and one dose of 850 µg/m² teplizumab on each of days 3-12.

36. The method of claim 35, wherein each of the additional 12-day courses is administered at about 6 months to about 24 months after the preceding course.

37. The method of claim 33, wherein the patient in need thereof is 8 years of age or older.

38. The method of claim 33, wherein each dose is administered by intravenous infusion.

39. The method of claim 38, wherein each dose of teplizumab is administered by intravenous infusion over a period of at least 30 minutes.

40. The method of claim 33, wherein the patient has been diagnosed with Stage 3 T1D within 6 weeks prior to the administering step.

41. The method of claim 33, wherein the second of said two courses of teplizumab is administered to the patient 6-12 months after the first of said two courses of teplizumab.

42. The method of claim 33, wherein the patient in need thereof is or has tested positive for at least one T1D-related autoantibody selected from glutamic acid decarboxylase 65 autoantibodies, islet antigen 2 autoantibodies, zinc transporter 8 autoantibodies, islet cell cytoplasmic autoantibodies, and insulin autoantibodies.

43. The method of claim 42, wherein the patient in need thereof has or has tested positive for hyperglycemia or overt hyperglycemia.

44. The method of claim 43, wherein the patient in need thereof is 8 years of age or older.

45. The method of claim 44, wherein each dose of teplizumab is administered by intravenous infusion over a period of at least 30 minutes.

46. The method of claim 43, wherein the patient in need thereof has or has tested positive for at least one of the following:

(i) a fasting plasma glucose level of ≥126 mg/dl (7.0 mmol/L);

(ii) a 2-hour plasma glucose level of ≥200 mg/dL (11.1 mmol/L) during an OGTT;

(iii) an HbA1c level of ≥6.5% (48 mmol/mol); and (iv) a random plasma glucose level of ≥200 mg/dL (11.1 mmol/L).

47. The method of claim 33, wherein the patient in need thereof has or has tested positive for hyperglycemia or overt hyperglycemia.

48. The method of claim 47, wherein the patient in need thereof has or has tested positive for at least one of the following:

(i) a fasting plasma glucose level of ≥126 mg/dl (7.0 mmol/L);

(ii) a 2-hour plasma glucose level of ≥200 mg/dL (11.1 mmol/L) during an OGTT;

(iii) an HbA1c level of ≥6.5% (48 mmol/mol); and (iv) a random plasma glucose level of ≥200 mg/dL (11.1 mmol/L).

49. The method of claim 33, wherein the two courses of teplizumab are administered at an interval of 6 months.

50. The method of claim 33, wherein the patient in need thereof has a peak C-peptide level of ≥0.2 pmol/mL during a mixed meal tolerance test (MMTT).

51. A method of delaying progression of Stage 3 type 1 diabetes (T1D) in a patient in need thereof, comprising administering, by intravenous infusion, to the patient in need thereof, two 12-day courses of teplizumab at an interval of 6 months to 12 months, wherein each 12-day course comprises a first dose of 106 µg/m² teplizumab on day 1, a second dose of 425 µg/m² teplizumab on day 2, and one dose of 850 µg/m² teplizumab on each of days 3-12, wherein the patient has been diagnosed with Stage 3 T1D within 8 weeks prior to the administering step.

52. The method of claim 51, wherein the patient in need thereof is 8 years of age or older.

53. The method of claim 51, wherein the patient in need thereof is or has tested positive for at least one T1D-related autoantibody selected from glutamic acid decarboxylase 65 autoantibodies, islet antigen 2 autoantibodies, zinc transporter 8 autoantibodies, islet cell cytoplasmic autoantibodies, and insulin autoantibodies.

54. The method of claim 53, wherein the patient in need thereof has or has tested positive for hyperglycemia or overt hyperglycemia.

55. The method of claim 54, wherein the patient in need thereof has or has tested positive for at least one of the following:

(i) a fasting plasma glucose level of ≥126 mg/dl (7.0 mmol/L);

(ii) a 2-hour plasma glucose level of ≥200 mg/dL (11.1 mmol/L) during an OGTT;

(iii) an HbA1c level of ≥6.5% (48 mmol/mol); and (iv) a random plasma glucose level of ≥200 mg/dL (11.1 mmol/L).

56. The method of claim 51, wherein the patient in need thereof has or has tested positive for hyperglycemia or overt hyperglycemia.

57. The method of claim 56, wherein the patient in need thereof has or has tested positive for at least one of the following:

(i) a fasting plasma glucose level of ≥126 mg/dL (7.0 mmol/L);

(ii) a 2-hour plasma glucose level of ≥200 mg/dL (11.1 mmol/L) during an OGTT;

(iii) an HbA1c level of ≥6.5% (48 mmol/mol); and (iv) a random plasma glucose level of ≥200 mg/dL (11.1 mmol/L).

58. The method of claim 51, wherein each dose of teplizumab is administered by intravenous infusion over a period of at least 30 minutes.

59. The method of claim 51, wherein the patient has been diagnosed with Stage 3 T1D within 6 weeks prior to the administering step.

60. The method of claim 51, wherein the two courses of teplizumab are administered at an interval of 6 months.

61. The method of claim 51, wherein the patient in need thereof has a peak C-peptide level of ≥0.2 pmol/mL during a mixed meal tolerance test (MMTT).

62. A method of delaying progression of Stage 3 type 1 diabetes (T1D) in a patient in need thereof, comprising administering, by intravenous infusion, to the patient in need thereof, two 12-day courses of teplizumab at an interval of 6 months, wherein each 12-day course comprises a first dose of 106 $\mu g/m^2$ teplizumab on day 1, a second dose of 425 $\mu g/m^2$ teplizumab on day 2, and one dose of 850 $\mu g/m^2$ teplizumab on each of days 3-12, wherein the patient in need thereof has been diagnosed with Stage 3 T1D within 12 weeks prior to the administering step, wherein the patient in need thereof is or has tested positive for at least one T1D-related autoantibody selected from glutamic acid decarboxylase 65 autoantibodies, islet antigen 2 autoantibodies, zinc transporter 8 autoantibodies, islet cell cytoplasmic autoantibodies, and insulin autoantibodies, and wherein the patient in need thereof has or has tested positive for hyperglycemia or overt hyperglycemia.

63. The method of claim 62, wherein the patient in need thereof is 8 years of age or older.

64. The method of claim 62, wherein the patient has been diagnosed with Stage 3 T1D within 6 weeks prior to the administering step.

65. The method of claim 64, wherein the patient in need thereof is 8 years of age or older.

66. The method of claim 62, wherein the patient in need thereof has or has tested positive for at least one of the following:

(i) a fasting plasma glucose level of ≥126 mg/dL (7.0 mmol/L);

(ii) a 2-hour plasma glucose level of ≥200 mg/dL (11.1 mmol/L) during an OGTT;

(iii) an HbA1c level of ≥6.5% (48 mmol/mol); and (iv) a random plasma glucose level of ≥200 mg/dL (11.1 mmol/L).

\* \* \* \* \*